(12) United States Patent
Schaffer et al.

(10) Patent No.: US 10,745,721 B2
(45) Date of Patent: *Aug. 18, 2020

(54) PROCESS FOR REACTING A CARBOXYLIC ACID ESTER

(71) Applicant: Evonik Operations GmbH, Essen (DE)

(72) Inventors: Steffen Schaffer, Herten (DE); Heiko Andrea, Marl (DE); Mirja Wessel, Bochum (DE); Hans-Georg Hennemann, Marl (DE); Harald Haeger, Luedinghausen (DE)

(73) Assignee: Evonik Operations GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/077,750

(22) Filed: Nov. 12, 2013

(65) Prior Publication Data
US 2014/0141478 A1 May 22, 2014

(30) Foreign Application Priority Data

Nov. 12, 2012 (EP) .................................... 12007663

(51) Int. Cl.
*C12N 9/18* (2006.01)
*C12N 9/10* (2006.01)
*C07K 14/21* (2006.01)
*C12N 1/21* (2006.01)
*C12P 7/64* (2006.01)
*C12P 13/02* (2006.01)
*C12P 7/62* (2006.01)
*C12P 13/00* (2006.01)

(52) U.S. Cl.
CPC ............ *C12P 7/62* (2013.01); *C07K 14/21* (2013.01); *C12N 9/1096* (2013.01); *C12N 9/18* (2013.01); *C12P 7/6436* (2013.01); *C12P 13/001* (2013.01); *C12Y 301/01085* (2013.01); *Y02P 20/582* (2015.11)

(58) Field of Classification Search
None
See application file for complete search history.

(56) References Cited

U.S. PATENT DOCUMENTS

| | | |
|---|---|---|
| 6,620,970 B2 | 9/2003 | Schiffer et al. |
| 6,639,108 B2 | 10/2003 | Schiffer et al. |
| 6,861,540 B2 | 3/2005 | Herwig et al. |
| 6,878,836 B2 | 4/2005 | Haas et al. |
| 7,030,052 B2 | 4/2006 | Stochniol et al. |
| 7,049,450 B2 | 5/2006 | Hofen et al. |
| 7,091,384 B2 | 8/2006 | Jaeger et al. |
| 7,507,862 B2 | 3/2009 | Stochniol et al. |
| 7,608,738 B2 | 10/2009 | Herwig et al. |
| 7,879,938 B2 | 2/2011 | Häger et al. |
| 8,022,201 B2 | 9/2011 | Roos et al. |
| 8,168,841 B2 | 5/2012 | Herwig et al. |
| 8,232,333 B2 | 7/2012 | Haeger et al. |
| 8,378,127 B2 | 2/2013 | Dingerdissen et al. |
| 8,399,658 B2 | 3/2013 | Hengstermann et al. |
| 8,445,720 B2 | 5/2013 | Hannen et al. |
| 8,703,451 B2 | 4/2014 | Haas et al. |
| 8,703,993 B2 | 4/2014 | Hannen et al. |
| 8,809,576 B2 | 8/2014 | Schraven et al. |
| 8,871,862 B2 | 10/2014 | Pawlik et al. |
| 9,000,223 B2 | 4/2015 | Micoine et al. |
| 2002/0087036 A1 | 7/2002 | Haas et al. |
| 2010/0266518 A1 | 10/2010 | Springer et al. |
| 2010/0274033 A1* | 10/2010 | Sanchez-Riera et al. ........ 554/1 |
| 2010/0291644 A1 | 11/2010 | Marx et al. |
| 2010/0324257 A1 | 12/2010 | Karau et al. |
| 2011/0118433 A1 | 5/2011 | Poetter et al. |
| 2011/0171702 A1 | 7/2011 | Reinecke et al. |

(Continued)

FOREIGN PATENT DOCUMENTS

| | | |
|---|---|---|
| CN | 101490271 A | 7/2009 |
| EP | 1 829 965 A1 | 9/2007 |

(Continued)

OTHER PUBLICATIONS

Xie et al., Improving simvastatin bioconversion in *Escherichia coli* by deletion of bioH, Metabolic Eng., 2007, 9, 379-86.*
Sanishvili et al., Integrating structure, bioinformatics, and enzymology to discover function, J. Biol. Chem., 2003, 278, 26039-45.*
Uniprot, Accession No. P13001, 2011, www.uniprot.org.*
Julsing et al., Outer membrane protein AlkL boosts biocatalytic oxyfunctionalization of hydrophobic substrates in *Escherichia coli*, Appl. Environ. Microbiol., Jun. 2012, 78, 5724-33.*
GenBank, Accession No. YP_492020.1, May 2012, www.ncbi.nlm.nih.gov.*

(Continued)

*Primary Examiner* — Robert B Mondesi
*Assistant Examiner* — Todd M Epstein
(74) *Attorney, Agent, or Firm* — Oblon, McClelland, Maier & Neustadt, L.L.P.

(57) ABSTRACT

The invention provides a process for reacting a carboxylic acid ester of the formula (I)

$$R^1\text{-A-COOR}^2 \qquad (I),$$

wherein $R^1$ is hydrogen, $-CH_2OH$, $-CHO$, $-COOR^3$, $-CH_2SH$, $-CH_2OR^3$ or $-CH_2NH_2$, $R^2$ is an alkyl group, $R^3$ is hydrogen or an alkyl group, and A is a substituted, unsubstituted, linear, branched and/or cyclic alkylene, alkenylene, arylene or aralkylene radical having at least 4 carbons, in the presence of a cell. The process comprises a) contacting the cell with said carboxylic acid ester in an aqueous solution, wherein the cell is a recombinant cell which has reduced activity of a polypeptide comprising SEQ ID NO: 2 or a variant thereof over the wild-type cell.

20 Claims, 1 Drawing Sheet
Specification includes a Sequence Listing.

(56) References Cited

U.S. PATENT DOCUMENTS

| | | |
|---|---|---|
| 2011/0251399 A1 | 10/2011 | Dingerdissen et al. |
| 2012/0034665 A1 | 2/2012 | Haas et al. |
| 2012/0264877 A1 | 10/2012 | Häger et al. |
| 2012/0315366 A1 | 12/2012 | Zehnacker et al. |
| 2012/0329111 A1* | 12/2012 | Burgard .................... C12P 7/26 435/148 |
| 2013/0052700 A1 | 2/2013 | Poetter et al. |
| 2013/0092232 A1 | 4/2013 | Pawlik et al. |
| 2013/0092233 A1 | 4/2013 | Pawlik et al. |
| 2013/0164797 A1 | 6/2013 | Gielen et al. |
| 2013/0165685 A1 | 6/2013 | Hannen et al. |
| 2013/0171388 A1 | 7/2013 | Pawlik et al. |
| 2013/0183725 A1 | 7/2013 | Poetter et al. |
| 2013/0207050 A1 | 8/2013 | Hermasch et al. |
| 2013/0240799 A1 | 9/2013 | Haeger et al. |
| 2013/0299750 A1 | 11/2013 | Hermasch et al. |
| 2014/0039210 A1 | 2/2014 | Erhardt et al. |
| 2014/0054224 A1 | 2/2014 | Erhardt et al. |
| 2014/0178948 A1 | 6/2014 | Schaffer et al. |
| 2014/0186905 A1 | 7/2014 | Schaffer et al. |
| 2014/0242646 A1 | 8/2014 | Pötter et al. |
| 2014/0308717 A1 | 10/2014 | Haas et al. |
| 2015/0010968 A1 | 1/2015 | Engel et al. |
| 2015/0044744 A1 | 2/2015 | Pfeffer et al. |

FOREIGN PATENT DOCUMENTS

| | | |
|---|---|---|
| WO | WO 2007/139871 A2 | 12/2007 |
| WO | WO 2012110124 A1 * | 8/2012 |
| WO | WO 2013/024114 A2 | 2/2013 |
| WO | WO 2013/135650 A1 | 9/2013 |
| WO | WO 2013/149864 A1 | 10/2013 |

OTHER PUBLICATIONS

GenBank, Accession No. CAB69081, 2008, www.ncbi.nlm.nih.gov.*
U.S. Appl. No. 14/077,750, filed Nov. 12, 2013, Schaffer, et al.
U.S. Appl. No. 14/238,591, filed Feb. 12, 2014, Schaffer, et al.
U.S. Appl. No. 09/985,179, filed Nov. 1, 2001, US2002/0087036 A1, Haas, et al.
U.S. Appl. No. 12/602,593, filed Mar. 19, 2010, US2010/0291644 A1, Marx, et al.
U.S. Appl. No. 13/140,921, filed Jun. 20, 2011, US2011/0251399 A1, Dingerdissen, et al.
U.S. Appl. No. 13/511,540, filed May 23, 2012, US2012/0315366 A1, Zehnacker, et al.
U.S. Appl. No. 12/759,787, filed Apr. 14, 2010, US2010/0266518 A1, Springer, et al.
U.S. Appl. No. 13/806,555, filed Mar. 11, 2013, US2013/0165685 A1, Hannen, et al.
U.S. Appl. No. 14/000,067, filed Oct. 24, 2013, US2014/0039210 A1, Erhardt, et al.
U.S. Appl. No. 14/000,028, filed Oct. 28, 2013, US2014/0054224 A1, Erhardt, et al.
U.S. Appl. No. 14/233,505, filed Jan. 17, 2014, US2014/0242646 A1, Pötter, et al.
U.S. Appl. No. 14/237,121, filed Feb. 20, 2014, US2014/0308717 A1, Haas, et al.
U.S. Appl. No. 13/721,481, filed Dec. 20, 2012, US2013/0164797 A1, Gielen, et al.
U.S. Appl. No. 14/380,483, filed Aug. 22, 2014, Schiemann, et al.
U.S. Appl. No. 14/363,165, filed Jun. 5, 2014, US2015/0044744 A1, Pfeffer, et al.
U.S. Appl. No. 14/367,610, filed Jun. 20, 2014, Haas, et al.
U.S. Appl. No. 14/373,089, filed Jul. 18, 2014, US2015/0010968 A1, Engel, et al.
U.S. Appl. No. 14/435,339, filed Apr. 13, 2015, Engel, et al.
U.S. Appl. No. 14/132,473, filed Dec. 18, 2013, US2014/0178948 A1, Schaffer, et al.
U.S. Appl. No. 14/419,580, filed Feb. 4, 2015, Erhardt, et al.
U.S. Appl. No. 12/742,318, filed May 11, 2010, US2010/0324257 A1, Kaarau, et al.
U.S. Appl. No. 13/263,761, filed Oct. 10, 2011, US2012/0034665 A1, Haas, et al.
U.S. Appl. No. 12/943,145, filed Nov. 10, 2010, US2011/0118433 A1, Pötter, et al.
U.S. Appl. No. 13/764,996, filed Feb. 12, 2013, US2013/0183725 A1, Poetter, et al.
U.S. Appl. No. 13/642,412, filed Jan. 2, 2013, US2013/0052700 A1, Poetter, et al.
U.S. Appl. No. 14/077,750, filed Nov. 12, 2013, US2014/0141478, Schaffer, et al.
U.S. Appl. No. 14/390,133, filed Oct. 2, 2014, Hennemann, et al.
U.S. Appl. No. 14/384,301, filed Sep. 10, 2014, Schaffer, et al.
U.S. Appl. No. 13/494,082, filed Jun. 12, 2012, US2012/0264877 A1, Häger et al.
U.S. Appl. No. 13/001,204, filed Dec. 23, 2010, US2011/0171702 A1, Reinecke et al
U.S. Appl. No. 13/882,689, filed Jul. 15, 2013, US2013/0299750 A1, Hermasch et al.
U.S. Appl. No. 13/882,799, filed May 1, 2013, US2013/020750 A1, Hermasch et al.
U.S. Appl. No. 13/729,280, filed Dec. 28, 2012, US2013/0171388 A1, Pawlik et al.
U.S. Appl. No. 14/238,576, filed Feb. 12, 2014, US2014/0186905 A1, Schaffer et al.
U.S. Appl. No. 13/804,328, filed Mar. 14, 2013, US2013/0240799 A1, Haeger et al.
U.S. Appl. No. 13/649,616, filed Oct. 11, 2012, US2013/0092233 A1, Pawlik et al.
U.S. Appl. No. 13/649,379, filed Oct. 11, 2012, US2013/0092232 A1, Pawlik et al.
U.S. Appl. No. 14/077,750, filed Nov. 12, 2013, US2014/0141478 A1, Schaffer et al.
U.S. Appl. No. 14/649,414, filed Jun. 3, 2015, Schaffer et al.
Wang, B. et al, *Escherichia coli* BioH: a highly enantioselective and organic solvent tolerant esterase for kinetic resolution of sec-alcohols, Tetrahedron Letters 51 (2010) 6360-6364, 5 pages.

* cited by examiner

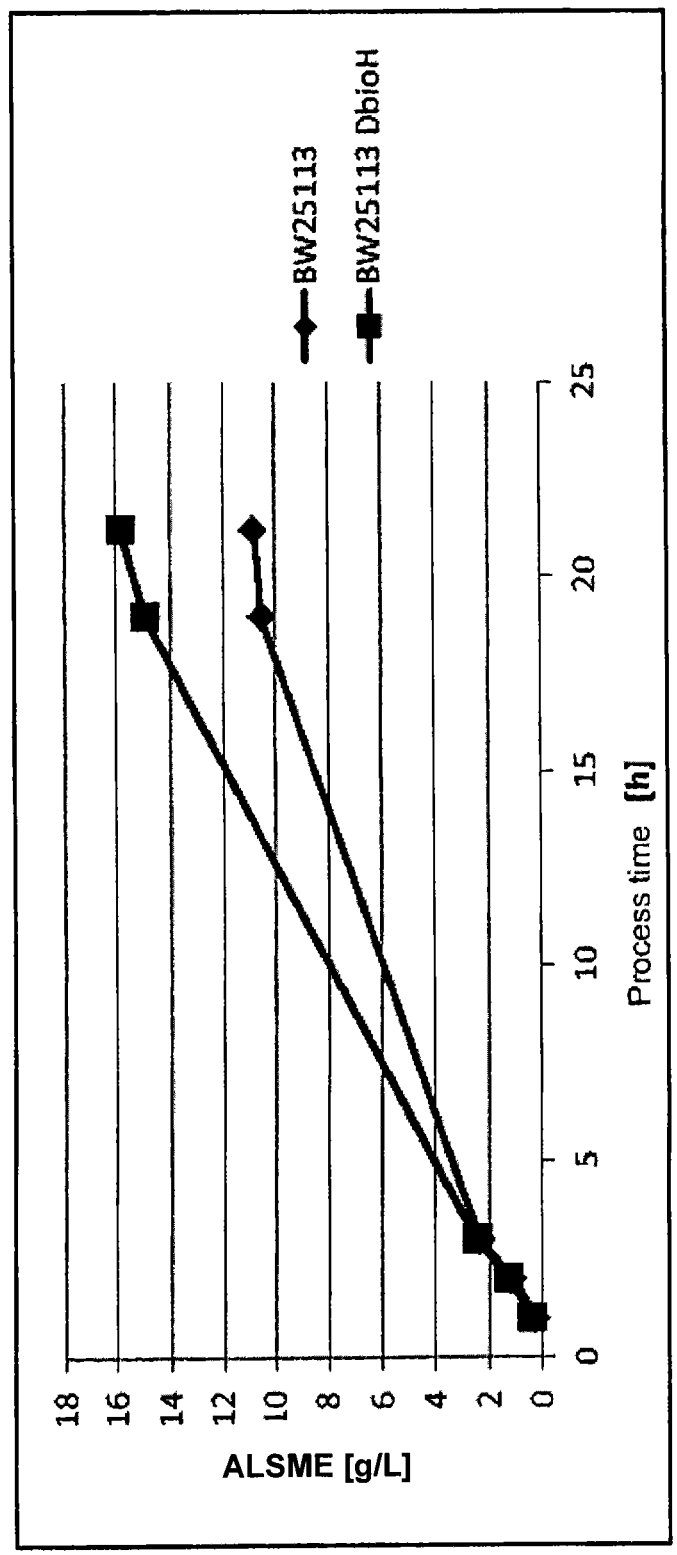

PROCESS FOR REACTING A CARBOXYLIC ACID ESTER

CROSS REFERENCE TO RELATED APPLICATIONS

This application claims priority to European Application No. EP 12007663, filed Nov. 12, 2012, the disclosure of which is incorporated herein by reference in its entirety.

BACKGROUND OF THE INVENTION

The invention relates to a process for reacting a carboxylic acid ester of the formula (I)

$$R^1\text{-A-COOR}^2 \qquad (I),$$

wherein $R^1$ is selected from the group comprising hydrogen, —$CH_2OH$, —CHO, —$COOR^3$, —$CH_2SH$, —$CH_2OR^3$ and —$CH_2NH_2$, wherein $R^2$ is selected from the group comprising hydrogen and alkyl, preferably methyl, ethyl and propyl, wherein $R^3$ is selected from the group comprising hydrogen and alkyl, preferably methyl, ethyl and propyl, and wherein A is a substituted, unsubstituted, linear, branched and/or cyclic alkylene, alkenylene, arylene or aralkylene radical having at least 4, more preferably 6, even more preferably 8, carbons, by means of a cell, comprising the step of a) contacting the cell with said carboxylic acid ester in an aqueous solution, wherein the cell is a recombinant cell which has reduced activity of a polypeptide having SEQ ID NO: 2 or a variant thereof over the wild-type cell, and to a cell suitable therefor, and to uses thereof.

Biotechnology is concerned with producing inter alia fine chemicals, employing various organisms that possess interesting synthesizing capabilities. Biotechnological processes have a number of advantages over conventional chemical processes. Firstly, they usually dispense entirely with harmful substances such as heavy metal-based catalysts and reaction conditions involving extreme pH, pressure and temperature values. Furthermore, the infrastructure required for the biotechnological process can often be set up with lower costs and safety measures. Selectivity and specificity of biotechnologically relevant enzymes often exceed those of chemical catalysts considerably, and formation of undesired secondary products which frequently are difficult to remove from the product and which would necessarily be produced in a synthesis using organic synthesis processes can thus be reduced. Finally, biotechnologically relevant organisms in many cases accept as reactants compounds like complex carbohydrates which may be derived from renewable raw materials. As a result, a producing enterprise may reduce its dependence on fossil raw materials such as petroleum and natural gas.

Establishing biotechnological processes, however, entails considerable difficulties which result in only very few substances being biotechnologically produced on an industrial scale these days, the main problem being that a cell with a desired synthesizing activity has not only the one enzyme responsible for said synthesizing activity but rather thousands of enzymes which co-exist in the same cell and compete with one another for substrates or even catalyse completely opposing reactions. Thus in the genome of Escherichia coli alone, approx. 80 polypeptides are encoded which have been identified by bioinformatics methods as hydrolases, i.e. enzymes which cleave particular bonds with consumption of a water molecule. Indeed, the conditions under which an enzyme is produced by the cell and the reactions catalysed by said enzyme and the substrates involved in said reactions have been elucidated exhaustively only in a few cases. It is therefore in many cases not possible to specifically select an enzyme for catalysing a particular reaction.

Accordingly, when employing cells as biocatalysts rather than chemical or isolated biological catalysts, there is also always the risk of a product or intermediate produced by an enzyme equipped with a desired activity or even the original reactant being converted by another enzyme into an unwanted secondary product. Whether this will happen and which of the numerous enzymes will have said unwanted activity in this case is impossible to predict in spite of technical advances in the field of bioinformatics.

It is not unlikely, especially with chemically reactive substances desired in the industry as reactive reactants for producing more complex products, that said substances react inside the cell with essential components of the organism and thus have a toxic action. If this is the case, the ability of the organism to grow and synthesize will be impaired, and ultimately the cell will die, without the developer being able to immediately recognize said toxicity. Likewise, the organism that will tolerate a chemically reactive substance as well as the tolerated concentration of the latter cannot be predicted.

In processes involving a plurality of reactions catalysed in each case by an enzyme, the complexity of the system makes the search for factors limiting yield or purity more difficult. If the product yield is too low, the reason for this may be the concentration of one of the enzymes present being too low, although that enzyme would not be known from among possible enzymes, that is to say owing to insufficient synthesizing capacity, the reactant is not reacted within the intended time frame or prior to degradation by competing enzymes. Alternatively, it is quite possible that an enzyme, although detectably present as a polypeptide in the cell, does not have the folding essential to the activity in that particular cell or that a hitherto unknown cofactor which is, however, essential to the activity is missing. Equally, as mentioned previously, the metabolic product may be toxic to the cell or broken down.

A person skilled in the art who would like to establish or improve a biotechnological process is thus confronted with numerous possible starting points, but in most cases is not provided by the prior art with any specific and executable instruction as to which of these starting points he needs to start from in order to achieve the objective.

Carboxylic acid esters constitute a group of compounds that are in high demand in the industry and that, either themselves or by way of processed products, are used as pharmaceuticals, cosmetics, plastics and the like.

Processing, however, frequently requires not only an ester function, which has to be introduced into a precursor first, but also further derivatization being carried out on the ester without hydrolysing the ester function in the process or subsequently. The latter is not a trivial accomplishment to be achieved, since many carboxylic acid esters tend to hydrolyse even in the absence of enzymes catalysing such reactions, in particular in aqueous solutions and at pH values greatly deviating from the neutral point.

An important possibility of further derivatizing carboxylic acid esters is oxidization of alkyl chains present therein. This first produces an alcohol which either is used as such or may be further oxidized to the aldehyde or ketone. The aldehyde or ketone may be either reductively aminated or further oxidized to the carboxylic acid which in turn may be esterified again, if required.

This multiplicity of possible reactions, many of which are catalysed by endogenous enzymes, i.e. enzymes that are naturally present in an organism, indicates that the problem of uncontrolled secondary product formation or metabolizing is particularly serious for reacting carboxylic acid esters by means of biotechnological processes.

An example of a carboxylic acid ester that is in high demand in the industry and that is customarily prepared starting from hydrocarbons present in petroleum is methyl 12-amino-dodecanoate(ALSME)[12-Aminolauric acid methylester]. ALSME is an important starting material in the preparation of polymers, for example for producing nylon-based line systems. ALSME has previously been produced in a low-yield process, starting from fossil raw materials.

A promising new way of biotechnologically producing ALS or ALSME is described in WO 2009/077461. This involves methyl dodecanoate being oxidized by a monooxygenase in a first step, and reacting the resultant aldehyde by means of a transaminase to give ALSME. A disadvantage of this process is the production of secondary products, for example the dicarboxylic acid, which can be removed from the desired product, ALSME, only with difficulties. This reduces the yield and makes recycling of hydrophobic solvents and hydrophobic cation exchangers, which may be used according to PCT/EP2011/071491 for removing the product from the aqueous reaction mixture, more difficult, at the expense of efficient resource usage.

Against this background, it is an object of the invention to provide a biotechnological process for reacting carboxylic acid esters which is as efficient as possible with regard to yield, carbon balance and/or nitrogen balance and/or purity.

Another object of the invention is to provide a biotechnological process for reacting carboxylic acid esters to give aminated carboxylic acid esters, which is as efficient as possible with regard to yield, carbon balance and/or nitrogen balance, re-usability of agents used and/or purity of the product. In this connection, an efficient carbon balance and/or nitrogen balance preferably means that the proportion of the carbon and/or nitrogen fed in the form of suitable substrates to a cell for reacting a carboxylic acid ester is as high as possible in the desired final product, instead of being reacted to give products other than the desired ones, for example.

Another object of the invention is to improve the ability of a multi-phase reaction mixture to be worked up from the reaction of a carboxylic acid ester, particularly with regard to re-usability of hydrophobic solvents and liquid cation exchangers used for work-up, and with regard to phase formation and separation in a biphasic system comprising an aqueous phase in which reaction of the carboxylic acid ester takes place and an organic phase with organic solvents and/or liquid cation exchangers.

SUMMARY OF THE INVENTION

These and further objects are achieved by the subject matter of the present application and in particular also by the subject matter of the enclosed independent claims, with the dependent claims giving rise to embodiments.

In a first aspect, the problem addressed by the invention is solved by a process for reacting a carboxylic acid ester of the formula (I)

$$R^1\text{-A-COOR}^2 \qquad (I),$$

wherein $R^1$ is selected from the group comprising hydrogen, —$CH_2OH$, —CHO, —$COOR^3$, —$CH_2SH$, —$CH_2OR^3$ and —$CH_2NH_2$, wherein $R^2$ is selected from the group comprising hydrogen and alkyl, preferably methyl, ethyl and propyl, wherein $R^3$ is selected from the group comprising hydrogen and alkyl, preferably methyl, ethyl and propyl, and wherein A is a substituted, unsubstituted, linear, branched and/or cyclic alkylene, alkenylene, arylene or aralkylene radical having at least 4, more preferably 6, even more preferably 8, carbons.

The process comprises:
a) contacting a cell with said carboxylic acid ester in an aqueous solution,
wherein the cell is a recombinant cell which has reduced activity of a polypeptide comprising SEQ ID NO: 2 or a variant thereof over the wild-type cell.

In a first embodiment of the first aspect, the problem is solved by a process further comprising:
b) contacting the aqueous solution with a hydrophobic organic solution comprising a cation exchanger.

In a second aspect, the problem addressed by the invention is solved by use of a knockout of a gene coding for a polypeptide comprising SEQ ID NO: 2 or a variant thereof as part of the genetic make-up of a recombinant cell for increasing production over the corresponding wild-type cell of a carboxylic acid ester of the formula (I)

$$R^1\text{-A-COOR}^2 \qquad (I),$$

wherein $R^1$ is selected from the group comprising hydrogen, —$CH_2OH$, —CHO, —$COOR^3$, —$CH_2SH$, —$CH_2OR^3$ and —$CH_2NH_2$, wherein $R^2$ is selected from the group comprising alkyl, preferably methyl, ethyl and propyl, wherein $R^3$ is selected from the group comprising hydrogen and alkyl, preferably methyl, ethyl and propyl, and wherein A is a substituted, unsubstituted, linear, branched and/or cyclic alkylene, alkenylene, arylene or aralkylene radical having at least 4, more preferably 6, even more preferably 8, carbons, in particular an alkylene radical having at least four, more preferably 6, even more preferably 8, carbons.

In a third aspect, the problem addressed by the invention is solved by using a recombinant cell which has reduced activity of a polypeptide having SEQ ID NO 2 or a variant thereof over the wild-type cell for reacting a carboxylic acid ester of the formula (I)

$$R^1\text{-A-COOR}^2 \qquad (I),$$

wherein $R^1$ is selected from the group comprising hydrogen, —$CH_2OH$, —CHO, —$COOR^3$, —$CH_2SH$, —$CH_2OR^3$ and —$CH_2NH_2$, wherein $R^2$ is selected from the group comprising hydrogen and alkyl, preferably methyl, ethyl and propyl, wherein $R^3$ is selected from the group comprising hydrogen and alkyl, preferably methyl, ethyl and propyl, and wherein A is a substituted, unsubstituted, linear, branched and/or cyclic alkylene, alkenylene, arylene or aralkylene radical having at least 4, more preferably 6, even more preferably 8, carbons, preferably an alkylene radical having at least eight carbons.

In another embodiment of the first, second or third aspect, the problem is solved by a process or a use, wherein A is a saturated alkylene radical, preferably an alkylene radical of the formula —$(CH_2)_n$—, where n is at least 4.

In another embodiment of the first aspect, the problem is solved by a process, wherein $R^1$ is selected from the group comprising hydrogen, —$CH_2OH$, —CHO and —$CH_2NH_2$.

In a fourth aspect, the problem addressed by the invention is solved by a cell expressing a recombinant alkane hydroxylase, wherein the activity of a polypeptide comprising SEQ ID NO 2 or a variant thereof is reduced over the wild-type cell.

In a preferred embodiment of the fourth aspect, the problem is solved by a cell, wherein the alkane hydroxylase is an alkane hydroxylase from the group comprising AlkB monooxygenases and a cytochrome P450 monooxygenase of the CYP153 family.

In a fifth aspect, the problem addressed by the invention is solved by a reaction mixture comprising the cell according to the fourth aspect or any of its embodiments in aqueous solution and a carboxylic acid ester of the formula (I)

wherein $R^1$ is selected from the group comprising hydrogen, —$CH_2OH$, —CHO, —$COOR^3$, —$CH_2SH$, —$CH_2OR^3$ and —$CH_2NH_2$, wherein $R^2$ is selected from the group comprising alkyl, preferably methyl, ethyl and propyl, wherein $R^3$ is selected from the group comprising hydrogen and alkyl, preferably methyl, ethyl and propyl, wherein A is a substituted, unsubstituted, linear, branched and/or cyclic alkylene, alkenylene, arylene or aralkylene radical having at least 4, more preferably 6, even more preferably 8, carbons.

In a further embodiment of the fifth aspect, the problem is solved by the reaction mixture, wherein A is an alkylene radical having at least four carbons, in particular a saturated alkylene radical, preferably an alkylene radical of the formula —$(CH_2)_n$—, where n is at least 4, wherein $R^1$ is preferably selected from the group comprising hydrogen, —$CH_2OH$, —CHO and —$CH_2NH_2$.

In one embodiment of the fifth aspect, the problem is solved by a reaction mixture further comprising a hydrophobic organic solution containing a cation exchanger.

In a preferred embodiment of the first to fifth aspects, the problem is solved by a process, a cell or a use, wherein the cell furthermore expresses a transaminase.

In a preferred embodiment of the first to fifth aspects, the problem is solved by a process, a cell or a use, wherein the cell furthermore expresses an alanine dehydrogenase.

In a preferred embodiment of the first to fifth aspects, the problem is solved by a process, a cell or a use, wherein the cell furthermore has a protein of the AlkL family.

In a preferred embodiment of the first to fifth aspects, the problem is solved by a process, a cell or a use, wherein the cell has an activity, which is reduced over its wild type, of at least one enzyme catalysing any of the reactions of fatty acid β-oxidation, wherein the enzyme is preferably one from the group comprising fatty acid-CoA ligase, acyl-CoA dehydrogenase, 2,4-dienoyl-CoA reductase, enoyl-CoA hydratase and 3-ketoacyl-CoA thiolase, a fatty acid importer or variants thereof, particularly preferably FadL or a variant thereof.

In a preferred embodiment of the first to fifth aspects, the problem is solved by a process, a cell or a use, wherein the cell has and/or overexpresses at least one enzyme from the group comprising alkane hydroxylase, alcohol dehydrogenase, transaminase, alanine dehydrogenase and protein of the AlkL family in recombinant form.

In a preferred embodiment of the first to fifth aspects, the problem is solved by a process, a cell or a use, wherein the activity of a polypeptide comprising SEQ ID NO: 2 or a variant thereof is reduced over the wild-type cell due to knockout of a gene coding for a polypeptide comprising SEQ ID NO: 2 or a variant thereof.

BRIEF DESCRIPTION OF THE DRAWINGS

FIG. 1 shows the concentration increase for ALSME with time according to two embodiments of the invention.

DESCRIPTION OF THE PREFERRED EMBODIMENTS OF THE INVENTION

Throughout this description all ranges described include all values and sub-ranges therein, unless otherwise specified.

Additionally, the indefinite article "a" or "an" carries the meaning of "one or more" throughout the description, unless otherwise specified.

The invention is based on the inventors surprisingly finding that a recombinant cell which has reduced activity of a polypeptide comprising SEQ ID NO: 2 in particular or a variant thereof over the wild-type cell is suitable for reacting carboxylic acid esters in that yield, carbon balance and/or nitrogen balance and purity of the products produced therefrom are surprisingly higher than with a cell that has the same activity as the wild-type cell with regard to the polypeptide comprising SEQ ID NO: 2. This is true, for example, for reactions in which the carboxylic acid ester is oxidized by using at least one alkane hydroxylase and optionally further enzymes.

The invention is based on the inventors furthermore surprisingly finding that a recombinant cell which has reduced activity of a polypeptide comprising SEQ ID NO: 2 or a variant thereof over the wild-type cell is suitable for reacting carboxylic acid esters particularly in that organic solvents and liquid cation exchangers used for working up the reaction product from the reaction of the carboxylic acid ester may be recovered particularly efficiently and/or frequently by recycling to be used again, and in that removal of the aqueous reaction mixture from a hydrophobic solution comprising organic solvent and/or liquid cation exchanger is improved.

The invention relates to a process for reacting a carboxylic acid ester in the presence of a cell, wherein the reaction may be any chemical reaction which utilizes the carboxylic acid ester of interest as reactant and in which hydrolysis or preliminary hydrolysis of the carboxylic acid ester or of a compound derived therefrom could impair the yield, carbon balance and/or nitrogen balance and/or purity of the product to be produced therefrom. The cell of the invention and the process of the invention are particularly suitable for reactions in which a different chemical function than the carboxylate group is reacted, for example a terminal alkyl group, and in which the aim is to retain the carboxylate group. According to the invention, however, it may also be possible to carry out according to the invention reactions such as transesterifications of the carboxylate group, in which the aim is to avoid a preliminary and unspecific reaction of the carboxylate group. The teaching according to the invention may also be suitable for reactions in which a compound containing the carboxylate group is not itself the reactant to be reacted but which require only said compound to be present and stable over a relatively long period, for example if said compound is an inducer or activator of an enzyme having an activity which is essential to the process.

To carry out the invention, it is essential for the cell according to the invention or cell used in a process according to the invention to be a recombinant cell that has reduced activity of a polypeptide comprising SEQ ID NO: 2 or a variant thereof over the wild-type cell. Said sequence codes for BioH, an enzyme known for its ability to convert, as part of the biosynthesis of biotin together with another enzyme, BioC, alanine and/or acetate into pimeloyl-CoA (Barker, D. F., and Campbell, A. M. (1980) *J. Bacteriol.* 143, 789-800). In *Escherichia coli*, BioH is encoded by a nucleotide sequence comprising SEQ ID NO: 1. In a preferred embodiment, the activity of the polypeptide comprising SEQ ID NO: 2 is reduced due to knockout, for example partial deletion, or other measures of reducing expression of a nucleotide sequence comprising SEQ ID NO: 1 or a variant thereof.

With the development of modern genetic, microbiological and molecular-biological methods, the skilled worker has numerous tools at his disposal which he may use to routinely measure and influence the activity of polypeptides present in living cells. The activity of an enzyme which is in the form of a suspension, a pellet, or may have been taken in processed form from a cell culture may be determined by using and analyzing enzymatic standard assays, as described in textbooks, for example Cornish-Bowden, 1995. An assay for determining the activity of the polypeptide comprising SEQ ID NO: 1 or a variant thereof is described in X. Xie et al. (2007) Metabolic Engineering 9; 379-386.

Routinely applicable processes for reducing the activity of an enzyme in a cell, for example by random mutagenesis of cells by exposure to radioactive radiation followed by concentrating or screening the mutants, by site-directed introduction of point mutations or by interruption of the reading frame or deletion of a part of the reading frame of a gene chromosomally integrated into a cell, which gene codes for an active enzyme, have also been described in the prior art, for example in Maniatis et al (1989) or in Fuchs & Schlegl (2007), and may routinely be performed by a person skilled in the art. It may also be possible to reduce activity on the basis of RNA interference (Tuschl, 2001) or using specific inhibitors. In a preferred embodiment, the wording "wherein the cell" has, "over its wild type, reduced activity" of a polypeptide, as used herein, means that the activity of the polypeptide in the modified cell is reduced compared to the activity of the same enzyme in a wild-type cell. In a preferred embodiment, the relative reduction is, in the order of increasing preference, 5, 10, 20, 40, 50, 75, 90, 95, 99 or more, percent of the activity. In a particularly preferred embodiment, activity of the enzyme is not detectable anymore over the background.

Particular preference is given to reducing the activity of the polypeptide comprising SEQ ID NO: 2 or a variant thereof by a knockout. In a preferred embodiment, the term "knockout", as used herein, means any measure that reduces the activity of the polypeptide comprising SEQ ID NO: 2 or a variant thereof permanently and irreversibly, in particular also in progeny of corresponding cells, preferably by interrupting the reading frame of the sequence coding for SEQ ID NO: 2 or a variant thereof, by deleting at least part of the sequence coding for SEQ ID NO: 2 or a variant thereof, which causes a loss of the enzyme activity of the encoded polypeptide but does not interrupt the reading frame, or by mutating a nucleotide sequence essential to expression, for example a promoter, a ribosome binding site or the like. Measures of preparing cells having reduced activities of specific polypeptides are routine procedures available to a person skilled in the art and are sufficiently well described in references, known to the artisan, for example in Kamionka et al. (2005) Appl Environ Microbiol. 2005 February; 71(2): 728-733, Geng et al. (2009), Journal of Biomedicine and Biotechnology Volume 2009, Article ID 646380, doi: 10.1155/2009/646380, and Murphy (2009) Methods Mol Biol. 2011; 765:27-42. Also suitable are commercially available kits, for example the TargeTron™ Gene Knockout System from Sigma Aldrich.

The invention provides a method of reacting a carboxylic acid ester of the formula (I)

R$^1$-A-COOR$^2$         (I), wherein R$^1$ is selected from the group comprising hydrogen, —CH$_2$OH, —CHO, —COOR$^3$, —CH$_2$SH, —CH$_2$OR$^3$ and —CH$_2$NH$_2$, wherein R$^2$ is selected from the group comprising alkyl, preferably methyl, ethyl and propyl, wherein R$^3$ is selected from the group comprising hydrogen and alkyl, preferably methyl, ethyl and propyl, and wherein A is a substituted, unsubstituted, linear, branched and/or cyclic alkylene, alkenylene, arylene or aralkylene radical having at least 4, more preferably 6, even more preferably 8, carbons. The alkylene radical A may be any, in particular linear, branched or cyclic, alkylene radical, provided that it comprises at least four carbons. In a particularly preferred embodiment, A is an alkylene chain of the formula —(CH$_2$)$_n$—, where n may be 4, 5, 6, 7, 8, 9, 10, 11, 12, 13, 14, 15, 16, 17, 18, 19, 20, 21, 22, 23, 24, 25, 26, 27, 28, 29 or 30. In a most preferred embodiment, A represents an alkylene radical of the formula —(CH$_2$)$_n$—, where n is from 4 to 24, more preferably 4 to 22, and most preferably 4 to 10, R$_1$ is hydrogen, —CH$_2$OH, —CHO, or —COOH, most preferably hydrogen, and R$^2$ is methyl or ethyl.

In connection with reactants of the carboxylic acid esters reacted according to the invention and all other compounds described herein, a compound described by structural features, for example a chemical formula, as a rule equally denotes protonated and deprotonated or other dissociated compounds. For example, the term "acetate" is understood as meaning equally the protonated form, i. e. acetic acid, and the dissociated form, i. e. CH$_3$—COO$^-$.

The cell to be employed according to the invention is preferably a whole cell catalyst in the form of a metabolically active cell which has an enzymatic activity required for reacting the carboxylic acid ester, particularly preferably by expressing a recombinant enzyme. In a further preferred embodiment, the cell is a lysate, an extract or another preparation of the cell, which has at least one enzymatic activity.

With regard to the choice of organism, the cell utilizable according to the invention is not subject to any restrictions, as long as it is cultivable, stable and accessible to processes for attenuating enzyme activities, for example knockouts. Thus it may equally be a prokaryotic or eukaryotic cell. In the case of a eukaryotic cell, particular preference may be given to unicellular eukaryotes, particularly yeasts such as *Saccharomyces cerevisiae, Candida tropicalis, Candida albicans* and *Pichia pastoris*. In the case of prokaryotic cells, it may be, for example, a bacterium selected from the group comprising *Magnetococcus, Mariprofundus, Acetobacter, Acetobacterium, Acidiphilium, Afipia, Ahrensia, Asticcacaulis, Aurantimonas, Azorhizobium, Azospirillum, Bacillus, Bartonella, tribocorum, Beijerinckia, Bradyrhizobium, Brevundimonas, subvibrioides, Brucella, Caulobacter, Chelativorans, Citreicella, Citromicrobium, Clostridium, Corynebacterium, Dinoroseobacter, Erythrobacter, Fulvimarina, Gluconacetobacter, Granulibacter, Hirschia, Hoeflea, Hyphomicrobium, Hyphomonas, Ketogulonicigenium, Labrenzia, Loktanella, Magnetospirillum, Maricaulis, Maritimibacter, Mesorhizobium, Methylobacte-* rium, *Methylocystis, Methylosinus, Nitrobacter, Novosphingobium, Oceanibulbus, Oceanicaulis, Oceanicola, Ochrobactrum, Octadecabacter, Oligotropha, Paracoccus, Parvibaculum, Parvularcula, Pelagibaca, Phaeobacter, Phenylobacterium, Polymorphum, Pseudovibrio, Rhodobacter, Rhodomicrobium, Rhodopseudomonas, Rhodospirillum, Roseibium, Roseobacter, Roseomonas, Roseovarius, Ruegeria, Sagittula, Silicibacter, Sphingobium, Sphingomonas, Sphingopyxis, Starkeya, Sulfitobacter, Thalassiobium, Xanthobacter, Zymomonas, Agrobacterium, Rhizobium, Sinorhizobium, Anaplasma, Ehrlichia, Neorickettsia, Orientia, Rickettsia, Wolbachia, Bordetella, Burkholderia, Cupriavidus, Taiwanensis, Lautropia, Limnobacter, Polynucleobacter, Ralstonia, Chromobacterium, Eikenella, corrodens, Basfia, Kingella, Laribacter, Lutiella, Neisseria, Simonsiella, Achromobacter, Acidovorax, Alicycliphilus, Aromatoleum, Azoarcus, Comamonas, Dechloromonas, Delftia, Gallionella, Herbaspirillum, Herminiimonas, Hylemonella, Janthinobacterium, Leptothrix, Methylibium, Methylobacillus, Methylophilales, Methyloversatilis, Methylovorus, Nitrosomonas, Nitrosospira, Oxalobacter, Parasutterella, Polaromonas, Polaromonas, Pusillimonas, Rhodoferax, Rubrivivax, Sideroxydans, Sutterella, wadsworthensis, Taylorella, Thauera, Thiobacillus, Thiomonas, Variovorax, Verminephrobacter, Anaeromyxobacter, Bdellovibrio, bacteriovorus, Bilophila, Desulfarculus, Desulfatibacillum, Desulfobacca, Desulfobacterium, Desulfobulbus, Desulfococcus, Desulfohalobium, Desulfitobacterium, Desulfomicrobium, Desulfonatronospira, Desulfotalea, Desulfovibrio, Desulfuromonas, Geobacter, Haliangium, Hippea, Lawsonia, Myxococcus, Pelobacter, Plesiocystis, Sorangium, Stigmatella, Syntrophobacter, Syntrophus, Arcobacter, Caminibacter, Campylobacter, Helicobacter, Nitratifractor, Nitratiruptor, Sulfuricurvum, Sulfurimonas, Sulfurospirillum, Sulfurovum, Wolinella, Buchnera, Blochmannia, Hamiltonella, Regiella, Riesia, Citrobacter, Cronobacter, Dickeya, Edwardsiella, Enterobacter, Erwinia, Escherichia, Klebsiella, Pantoea, Pectobacterium, Proteus, Providencia, Rahnella, Salmonella, Serratia, Shigella, Sodalis, Wigglesworthia, Glossina, Xenorhabdus, Yersinia, Acidithiobacillus, Acinetobacter, Aeromonas, Alcanivorax, Alkalilimnicola, Allochromatium, Alteromonadales, Alteromonas, Baumannia, Beggiatoa, Bermanella, Carsonella, Ruthia, Vesicomyosocius, Cardiobacterium, Chromohalobacter, Colwellia, Congregibacter, Coxiella, Dichelobacter, Endoriftia, Enhydrobacter, Ferrimonas, Francisella, Glaciecola, Hahella, Halomonas, Halorhodospira, Halothiobacillus, Idiomarina, Kangiella, Legionella, Marinobacter, Marinomonas, Methylobacter, Methylococcus, Methylomicrobium, Methylophaga, Moraxella, Moritella, Neptuniibacter, Nitrococcus, Pseudoalteromonas, Psychrobacter, Psychromonas, Reinekea, Rickettsiella, Saccharophagus, Shewanella, Succinatimonas, Teredinibacter, Thioalkalimicrobium, Thioalkalivibrio, Thiomicrospira, Tolumonas, Vibrionales, Actinobacillus, Aggregatibacter, Gallibacterium, Haemophilus, Histophilus, Mannheimia, Pasteurella, Azotobacter, Cellvibrio, Pseudomonas, Aliivibrio, Grimontia, Photobacterium, Photobacterium, Vibrio, Pseudoxanthomonas, Stenotrophomonas, Xanthomonas, Xylella, Borrelia, Brachyspira, Leptospira, Spirochaeta, Treponema, Hodgkinia, Puniceispirillum, Liberibacter, Pelagibacter, Odyssella, Accumulibacter*, in particular *B. subtilis, B. megaterium, C. glutamicum, E. coli, Pseudomonas* sp., *Pseudomonas fluorescens, Pseudomonas putida, Pseudomonas stutzeri, Acinetobacter* sp., *Burkholderia* sp., *Burkholderia thailandensis*, cyanobacteria, *Klebsiella* sp., *Klebsiella oxytoca, Salmonella* sp., *Rhizobium* sp. and *Rhizobium meliloti*. In a particularly preferred embodiment, it is an enterobacterium, most preferably *Escherichia coli*.

The process of the invention requires contacting the cell with the carboxylic acid ester in an aqueous solution. In a preferred embodiment, the term "contacting", as used herein, means that the cell according to the invention comes into direct contact with the particular agent, for example the carboxylic acid ester or a liquid cation exchanger, in particular without any physical barriers such as porous membranes or the like in between. In the simplest case, contacting comprises adding the agent, for example the carboxylic acid ester or the liquid cation exchanger, to an aqueous solution containing the cell.

Aqueous solutions that may be used are any water-based solutions suitable for maintaining or culturing the cell and/or its activity that is required for reacting the carboxylic acid ester. These include equally culture media for microorganisms, including complete media such as LB media, minimal media such as M9 media, and selective media, for example those containing a high salt concentration and therefore enable only halophilic or at least halotolerant organisms to grow. A particularly preferred medium is a minimal medium that contains very few components which can readily be removed from the product of the reaction of the carboxylic acid ester, in order to facilitate work-up of said product.

If the product of the intended reaction is sufficiently hydrophobic and has an appropriate charge, it is possible to extract it in a step b) by contacting the aqueous solution with a hydrophobic organic solution comprising a cation exchanger. Appropriate procedures are described in the international application PCT/EP2011/071491 or in the European application EP12181153.3. Briefly, the aqueous solution may be contacted with a hydrophobic solution comprising a fatty acid ester as solvent and a fatty acid, preferably an unsaturated fatty acid, during or after the reaction.

The requirements of the cell, the reaction and necessary enzymes must be taken into account when setting the temperature and conditions in step a). The temperature requirements of various biotechnologically important cells can be found in textbooks of microbiology and molecular biology, for example Fuchs/Schlegl, Allgemeine Mikrobiologie [General Microbiology], 2008, or may be determined by culturing experiments within routine procedures. In a preferred embodiment, the pH of the aqueous culture medium at the time of contacting is between 4 and 9, more preferably between 4.5 and 8.5, most preferably between 6.5 and 7.5. In another preferred embodiment, the temperature is between 0 and 45° C., more preferably between 15 and 40° C., most preferably between 20 and 37° C.

Preference may be given to using for the process of the invention a cell expressing a recombinant alkane hydroxylase, wherein the activity of a polypeptide comprising SEQ ID NO: 2 or a variant thereof is reduced over the wild-type cell. In a preferred embodiment, the alkane hydroxylase may be a cytochrome P450 monooxygenase of the CYP153 family. In a preferred embodiment, the term "cytochrome P450 monooxygenase of the CYP153 family" means a cytosolic oxidase which is part of a 3-component system comprising furthermore a ferredoxin and a ferredoxin reductase, with an alkane-binding site and the ability to hydroxylate alkanes. In a particularly preferred embodiment, the enzyme may have at least 80, preferably 90, most preferably 95 or 99, percent sequence identity with cytochrome P450 monooxygenase of the CYP153 family from *Alcanivorax borkumensis* SK2 (database code YP_691921), or the enzyme may have a polypeptide sequence which has at least 80, preferably 90, most preferably 95 or 99, percent sequence identity with cytochrome P450 monooxygenase of the CYP153 family from *Alcanivorax borkumensis* SK2 (database code YP_691921), and additionally has alkane hydroxylase activity. The database codes stated here, as throughout the application, refer to the NCB (National Center for Biotechnology Information, Bethesda, USA)I databases, more precisely the version available online on 8 Nov. 2012. In a preferred embodiment, the term "alkane hydroxylase activity", as used herein, means the ability to catalyse the hydroxylation of alkanes or unsubstituted linear alkyl radicals comprising at least six, preferably twelve, carbon radicals. In another preferred embodiment, the term "cytochrome P450 monooxygenase of the CYP153 family" means a non-membrane-bound oxidase which comprises a binding site for alkanes, unsubstituted linear alkyl radicals comprising at least five, preferably twelve, carbon radicals or monohydroxylated alkanes, and the polypeptide chain of which comprises the motif LL(I/L)(V/I)GGNDTTRN. In a preferred embodiment, a "cytochrome P450 monooxygenase of the CYP153 family", as used herein, is a cytochrome P450 monooxygenase of the CYP153 family from *Alcanivorax borkumensis* SK2 (database code YP_691921) or a variant which preferably has alkane hydroxylase activity.

The enzymes used according to the invention may preferably be recombinant enzymes. In a preferred embodiment, the term "recombinant", as used herein, means that the corresponding nucleic acid molecule may not be present in the natural cell and/or was produced using genetic engineering methods. In a preferred embodiment, a protein is said to be recombinant if the corresponding polypeptide is encoded by a recombinant nucleic acid. In a preferred embodiment, a recombinant cell, as used herein, means a cell which has at least one recombinant nucleic acid or one recombinant polypeptide. A person skilled in the art is familiar with processes suitable for producing recombinant molecules or cells, for example those described in Sambrook/Fritsch/Maniatis (1989): Molecular Cloning: A Laboratory Manual, Cold Spring Harbor Laboratory Press, $2^{nd}$ edition. Recombinant enzymes are preferably overexpressed, for example by using pET- or pGEX-vector systems which are known to a person skilled in the art.

To supply cytochrome P450 monooxygenase of the CYP153 family with electrons from the reducing agent, preferably NADH, in an optimal way, preference may be given to the cell expressing said monooxygenase together with ferredoxin reductase and ferredoxin, both of which interact functionally with said monooxygenase. The polypeptides may be isolated or, when using a whole cell catalyst, co-expressed polypeptides or polypeptides fused N- or C-terminally to the cytochrome P450 monooxygenase of the CYP153 family. A person skilled in the art can readily determine whether a ferredoxin reductase or a ferredoxin interacts functionally with a given cytochrome P450 monooxygenase of the CYP153 family by whether the reducing agent is oxidized in the presence of an alkane substrate and the three polypeptides. Alternatively, the enzyme assay described by Scheps, D., Malca, H., Hoffmann, B., Nestl, B. M, and Hauer, B. (2011) *Org. Biomol. Chem.*, 9, 6727, may be used, which shows a distinct increase in the reaction rate in the case of functionally interacting polypeptides. In a particularly preferred embodiment, cytochrome P450 monooxygenase of the CYP153 family, ferredoxin and ferredoxin reductase are from the same organism. In a particularly preferred embodiment, ferredoxin reductase may be that from *Alcanivorax borkumensis* SK2 (database code YP_691923) or may be a variant thereof, ferredoxin is that from *Alcanivorax borkumensis* SK2 (database code YP_691920) or is a variant thereof, and cytochrome P450 monooxygenase of the CYP153 family is that from *Alcanivorax borkumensis* SK2 (database code YP_691921) or is a variant thereof.

In another preferred embodiment, the alkane hydroxylase may be an AlkB monooxygenase. AlkB is an oxidoreductase first known from the *Pseudomonas putida* Gpo1 AlkBGT system, which is dependent on another two polypeptides, AlkG and AlkT. AlkT is characterized as FAD-dependent rubredoxin reductase that passes on electrons from NADH to AlkG. AlkG is a rubredoxin, an iron-containing redox protein that acts as a direct electron donor for AlkB. In a preferred embodiment, the term "AlkB monooxygenase" means a polypeptide with a sequence homology of at least, in the order of increasing preference, 75, 80, 85, 90, 92, 94, 96, 98 or 99% to the sequence of *Pseudomonas putida* Gpo1 AlkB (database code: CAB54050.1; this database code, like all the others used in the application, is from the NCBI database, more precisely the release available online on 15 Oct. 2012), which polypeptide is capable of oxidizing alkanes. In a particularly preferred embodiment, the AlkB monooxygenase may be an alkane-oxidizing oxidoreductase which functionally acts together with the *Pseudomonas putida* Gpo1 AlkG (CAB54052.1) and AlkT (CAB54063.1) polypeptides. For optimal supply of AlkB alkane hydroxylase with electrons, preference may be given to the cell expressing the monooxygenase together with auxiliary proteins that functionally interact with it, preferably AlkG and/or AlkT or respective variants thereof, which, in a particularly preferred embodiment, are again *Pseudomonas putida* Gpo1 AlkG (CAB54052.1) and AlkT (CAB54063.1) polypeptides.

The ability of the cell of the invention or the cell used in the process of the invention to oxidize substrates may be enhanced by said cell expressing an alcohol dehydrogenase as an alternative to or additionally to the alkane hydroxylase. In a preferred embodiment, the term "alcohol dehydrogenase", as used herein, means an enzyme that oxidizes an aldehyde or ketone to the corresponding primary or secondary alcohol. Examples include the alcohol dehydrogenases of *Ralstonia eutropha* (ACB78191.1), *Lactobacillus brevis* (YP_795183.1), *Lactobacillus kefiri* (ACF95832.1), from horse liver, of *Paracoccus pantotrophus* (ACB78182.1) and *Sphingobium yanoikuyae* (EU427523.1), and also the respective variants thereof.

The use of a whole cell catalyst may give rise to the problem of a substrate having to be contacted with an enzyme located intracellularly for the desired reaction to occur. In the case of long-chain alkanes and derivatives thereof, preference may be given to the whole cell catalyst having a polypeptide of the AlkL family. In a preferred embodiment, a "polypeptide of the AlkL family", as used herein, may be a polypeptide which, over a length of 230 consecutive amino acids, has at least 80, preferably 90, even more preferably 90% sequence identity to *Pseudomonas putida* AlkL (database code CAB69081, incorporated herein by reference; SEQ ID NO: 15) or a variant of *Pseudomonas putida* AlkL and preferably the ability to support importing long-chain alkanes into the interior of a cell. In another embodiment, a "polypeptide of the AlkL family", as used herein, is a polypeptide located in the outer membrane of a Gram-negative bacterium, which has the sequence motif DXWAPAXQ(V/A)GXR, where X is a proteinogenic amino acid, and preferably additionally is *Pseudomonas putida*

AlkL (database code CAB69081, incorporated herein by reference) or a variant thereof. Exemplary members of the AlkL family include AlkL from *Pseudomonas putida* (database code CAB69081, incorporated herein by reference), *Marinobacter aquaeolei* VT8 (database code YP_957722), *Oceanicaulis alexandrii* HTCC2633 (database code ZP_00953584), *Marinobacter manganoxydans* Mnl7-9 (database code ZP_09158756), *Caulobacter* sp. K31 (database code YP_001672217), *Pseudomonas oleovorans* (database code Q00595), and variants thereof.

The present invention may be performed not only by using macromolecules with the exact amino acid or nucleic acid sequence to which reference is made herein, or not only by using a cell having an activity of a polypeptide with the exact amino acid sequence to which reference is made herein, which activity is reduced relatively to the particular wild type, but also by using a variant of such macromolecules or a cell having an activity of a variant of said polypeptide, which may be obtained by deletion, addition or substitution of one or more than one amino acid or nucleic acid, which activity is reduced relatively to the particular wild type of the particular cell. In a preferred embodiment, the term "variant" of a nucleic acid sequence or an amino acid sequence, used synonymously and interchangeably with the term "homologue" hereinbelow, means, as used herein, a different nucleic acid or amino acid sequence which has a homology, used synonymously with identity herein, of 70, 75, 80, 85, 90, 92, 94, 96, 98, 99 or more, percent with regard to the corresponding original wild-type nucleic acid or amino acid sequence, wherein preferably amino acids other than those forming the catalytically active site or those essential to structure or folding have been deleted or substituted, or else merely conservative substitutions have taken place, for example glutamate for aspartate or leucine for valine. Algorithms which may be used for calculating the degree of homology of two sequences are conventionally known, for example Arthur Lesk (2008), Introduction to bioinformatics, 3$^{rd}$ edition. In another more preferred embodiment of the present invention, the variant of an amino acid sequence or nucleic acid sequence may have, preferably in addition to the sequence homology mentioned above, essentially the same enzymatic activity of the wild-type molecule or the original molecule. For example, a variant of a polypeptide which has protease enzymatic activity may have the same or essentially the same proteolytic activity as the polypeptide enzyme, i.e. the ability to catalyse hydrolysis of a peptide bond. In a particular embodiment, the term "essentially the same enzymatic activity" means an activity with regard to the substrates of the wild-type polypeptide that is markedly above background activity or/and differs by less than 3, more preferably 2, even more preferably an order of magnitude from the $K_M$ and/or $k_{cat}$ values of the wild-type polypeptide with regard to the same substrates. In another preferred embodiment, the term "variant" of a nucleic acid or amino acid sequence comprises at least one active part/or fragment of said nucleic acid or amino acid sequence. In another preferred embodiment, the term "active part", as used herein, means an amino acid sequence or a nucleic acid sequence, which is shorter than the full-length amino acid sequence or which codes for a shorter than the full-length amino acid sequence, with the amino acid sequence or the encoded amino acid sequence with a shorter length than the wild-type amino acid sequence having essentially the same enzymatic activity as the wild-type polypeptide or a variant thereof, for example as protease. In a particular embodiment, the term "variant" of a nucleic acid comprises a nucleic acid, the complementary strand of which binds to the wild-type nucleic acid, preferably under stringent conditions. The stringency of the hybridization reaction can readily be determined by a person skilled in the art and generally depends on the length of the probe, the temperatures during washing and the salt concentration. Generally, longer probes require higher temperatures for hybridizing, whereas low temperatures are adequate for shorter probes. Whether hybridization takes place generally depends on the ability of the denatured DNA to anneal to complementary strands in its surroundings, specifically below the melting temperature. The stringency of hybridization reactions and corresponding conditions are described in more detail in F. M. Ausubel (1995), Current Protocols in Molecular Biology. John Wiley & Sons, Inc. Instructions for the identification of DNA sequences by means of hybridization are found by the person skilled in the art, inter alia, in the handbook "The DIG System Users Guide for Filter Hybridization" of Boehringer Mannheim GmbH (Mannheim, Germany, 1993) and in Liebl et al. (International Journal of Systematic Bacteriology 41: 255-260 (1991)). In a preferred embodiment, hybridization may take place under stringent conditions, that is to say only hybrids are formed in which probe and target sequence, i.e. the polynucleotides treated with the probe, are at least 70% identical. It is known that the stringency of the hybridization including the washing steps is influenced or determined by varying the buffer composition, the temperature and the salt concentration. The hybridization reaction is in general carried out with a relatively low stringency in comparison to the washing steps (Hybaid Hybridisation Guide, Hybaid Limited, Teddington, UK, 1996). For the hybridization reaction, it is possible, for example, to employ a buffer corresponding to 5×SSC buffer at a temperature of about 50° C.-68° C. Here, probes can also hybridize with polynucleotides that have less than 70% identity to the sequence of the probe. Such hybrids are less stable and are removed by washing under stringent conditions. This can be achieved, for example, by lowering the salt concentration to 2×SSC and optionally subsequently 0.5×SSC (The DIG System User's Guide for Filter Hybridisation, Boehringer Mannheim, Mannheim, Germany, 1995), where a temperature of, in the order of increasing preference, about 50° C.-68° C., about 52° C.-68° C., about 54° C.-68° C., about 56° C.-68° C., about 58° C.-68° C., about 60° C.-68° C., about 62° C.-68° C., about 64° C.-68° C., about 66° C.-68° C. is adjusted. Temperature ranges of about 64° C.-68° C. or about 66° C.-68° C. are preferred. It is optionally possible to lower the salt concentration to a concentration corresponding to 0.2×SSC or 0.1×SSC. By increasing the hybridization temperature stepwise in steps of about 1-2° C. from 50° C. to 68° C. polynucleotide fragments may be isolated that have, for example, in the order of increasing preference, at least 70% or at least 80% or at least 90%, at least 91%, at least 92%, at least 93%, at least 94%, at least 95%, at least 96%, at least 97%, at least 98% or at least 99% identity to the sequence of the nucleic acid molecule employed. Further instructions for hybridization are obtainable on the market in the form of "kits" (e.g. DIG Easy Hyb from Roche Diagnostics GmbH, Mannheim, Germany, catalogue no. 1603558). In a preferred embodiment, the term "variant" of a nucleic acid, as used herein, comprises any nucleic acid sequence which codes for the same amino acid sequence as the original nucleic acid or a variant of this amino acid sequence within the bounds of the degeneracy of the genetic code.

In a preferred embodiment, the cell used according to the invention may have a reduced activity, over its wild type, of at least one enzyme catalysing any of the reactions of fatty acid β-oxidation, which enzyme may preferably be from the group comprising fatty acid-CoA ligase, acyl-CoA dehydrogenase, 2,4-dienoyl-CoA reductase, enoyl-CoA hydratase and 3-ketoacyl-CoA thiolase, a fatty acid importer, or variants thereof, and particularly preferably is FadL or a variant thereof. β-Oxidation of fatty acids is a widespread metabolic pathway which allows prokaryotic and equally eukaryotic organisms to oxidize fatty acids and to render the chemical energy stored therein metabolically available. It starts in a wider sense with a fatty acid being taken up into the cell, in the case of E. coli through the transporter FadL which passes it through the outer and inner membranes of the Gram-negative bacterial cell, and the FadD gene product which releases the fatty acid by way of the CoA ester into the cytosol. There, if required by the conditions, the fatty acid is first oxidized at the β-position of the fatty acid-CoA ester by an acyl-CoA dehydrogenase, FadE in the case of E. coli. Alternatively, a similar molecule may also be formed from a diunsaturated fatty acid by reduction by means of a 2,4-dienoyl-CoA reductase, FadH in E. coli. A multifunctional enzyme, enoyl-CoA hydratase/β-hydroxyacyl-CoA dehydrogenase, FadB in E. coli, then catalyses hydratization with the formation of the secondary alcohol which is subsequently oxidized to the ketone. In the last step, a 3-ketoacyl-CoA thiolase, FadA in the case of E. coli, catalyses cleavage of ketoacyl-CoA, resulting in acetyl-CoA and a fatty acid-CoA ester that is shorter by two carbons compared to the starting molecule being released. If the latter is not acetyl-CoA as well, it may be fed again into the β-oxidation cycle and shortened with oxidation. FadR, a regulator of the Fad operon comprising the genes required for the breakdown of fatty acids, is also involved in regulating fatty acid β-oxidation, but would not catalyse a β-oxidation reaction. In a preferred embodiment, the term "enzyme catalysing any of the reactions of fatty acid β-oxidation" means any enzyme which interacts directly with the fatty acid substrate or a molecule produced therefrom on the pathway to acetyl-CoA, preferably recognizing it as substrate, and catalyses its conversion to a metabolite that is closer to acetyl-CoA on this catabolic pathway, preferably including the fatty acid importer which takes up the fatty acid into the cell. According to the definition above, these enzymes include, for example, acyl-CoA dehydrogenase, since it interacts with the fatty acid-CoA ester and catalyses its conversion to enoyl-CoA which is closer to acetyl-CoA than the fatty acid-CoA ester on the β-oxidation metabolic pathway. In a particularly preferred embodiment, the term "enzyme catalysing any of the reactions of fatty acid β-oxidation", as used herein, means any enzyme from the group comprising the gene products FadA, FadB, FadD, FadL and FadE from E. coli and/or their variants or homologues from other organisms. The gene products FadA, FadB, FadD, FadL and FadE from E. coli and also variants and homologues from numerous other biotechnologically utilizable organisms and their nucleic acid and polypeptide sequences are known, for example FadA under accession number AP009048.1, FadB under accession number BAE77457.1, FadD under accession number BAA15609.1, FadE under accession number BAA77891.2 and FadL under accession number BAA16205.1.

In another preferred embodiment, the cell of the invention or cell used in the process of the invention may expresse a transaminase. In a preferred embodiment, the term "transaminase", as used herein, means an enzyme catalysing the transfer of α-amino groups from a donor molecule, preferably an amino acid, to an acceptor molecule, preferably an α-ketocarboxylic acid. For example, use may be made of a transaminase from the group comprising 3HMU_A, AAD41041.1, AAK15486.1, ABE03917.1, ADR60699.1, ADR61066.1, ADR62525.1, AEL07495.1, CAZ86955.1, EFW82310.1, EFW87681.1, EGC99983.1, EGD03176.1, EGE58369.1, EGH06681.1, EGH08331.1, EGH24301.1, EGH32343.1, EGH46412.1, EGH55033.1, EGH62152.1, EGH67339.1, EGH70821.1, EGH71404.1, EGH78772.1, EGH85312.1, EGH97105.1, EGP57596.1, NP_102850.1, NP_106560.1, NP_248912.1, NP_248990.1, NP_354026.2, NP_421926.1, NP_637699.1, NP_642792.1, NP_744329.1, NP_744732.1, NP_747283.1, NP_795039.1, NP_901695.1 (XP_002943905.1, YP_001021095.1, YP_001059677.1, YP_001061726.1, YP_001066961.1, YP_001074671.1, YP_001120907.1, YP_001140117.1, YP_001170616.1, YP_001185848.1, YP_001188121.1, YP_001233688.1, YP_001268866.1, YP_001270391.1, YP_001345703.1, YP_001412573.1, YP_001417624.1, YP_001526058.1, YP_001579295.1, YP_001581170.1, YP_001668026.1, YP_001669478.1, YP_001671460.1, YP_001685569.1, YP_001747156.1, YP_001749732.1, YP_001765463.1, YP_001766294.1, YP_001790770.1, YP_001808775.1, YP_001809596.1, YP_001859758.1, YP_001888405.1, YP_001903233.1, YP_001977571.1, YP_002229759.1, YP_002231363.1, YP_002280472.1, YP_002297678.1, YP_002543874.1, YP_002549011.1, YP_002796201.1, YP_002801960.1, YP_002875335.1, YP_002897523.1, YP_002912290.1, YP_002974935.1, YP_003060891.1, YP_003264235.1, YP_003552364.1, YP_003578319.1, YP_003591946.1, YP_003607814.1, YP_003641922.1, YP_003674025.1, YP_003692877.1, YP_003755112.1, YP_003896973.1, YP_003907026.1, YP_003912421.1, YP_004086766.1, YP_004142571.1, YP_004147141.1, YP_004228105.1, YP_004278247.1, YP_004305252.1, YP_004356916.1, YP_004361407.1, YP_004378186.1, YP_004379856.1, YP_004390782.1, YP_004472442.1, YP_004590892.1, YP_004612414.1, YP_004676537.1, YP_004693233.1, YP_004701580.1, YP_004701637.1, YP_004704442.1, YP_108931.1, YP_110490.1, YP_168667.1, YP_237931.1, YP_260624.1, YP_262985.1, YP_271307.1, YP_276987.1, YP_334171.1, YP_337172.1, YP_350660.1, YP_351134.1, YP_364386.1, YP_366340.1, YP_369710.1, YP_370582.1, YP_426342.1, YP_440141.1, YP_442361.1, YP_468848.1, YP_521636.1, YP_554363.1, YP_608454.1, YP_610700.1, YP_614980.1, YP_622254.1, YP_625753.1, YP_680590.1, YP_751687.1, YP_767071.1, YP_774090.1, YP_774932.1, YP_788372.1, YP_858562.1, YP_928515.1, YP_983084.1, YP_995622.1, ZP_00948889.1, ZP_00954344.1, ZP_00959736.1, ZP_00998881.1, ZP_01011725.1, ZP_01037109.1, ZP_01058030.1, ZP_01076707.1, ZP_01103959.1, ZP_01167926.1, ZP_01224713.1, ZP_01442907.1, ZP_01446892.1, ZP_01550953.1, ZP_01625518.1, ZP_01745731.1, ZP_01750280.1, ZP_01754305.1, ZP_01763880.1, ZP_01769626.1, ZP_01865961.1, ZP_01881393.1, ZP_01901558.1, ZP_02145337.1, ZP_02151268.1, ZP_02152332.1, ZP_02167267.1, ZP_02190082.1, ZP_02242934.1, ZP_02360937.1, ZP_02367056.1, ZP_02385477.1, ZP_02456487.1, ZP_02883670.1, ZP_03263915.1, ZP_03263990.1, ZP_03400081.1, ZP_03452573.1, ZP_03456092.1, ZP_03517291.1, ZP_03529055.1, ZP_03571515.1, ZP_03572809.1, ZP_03587785.1, ZP_03588560.1, ZP_03697266.1, ZP_03697962.1, ZP_04521092.1, ZP_04590693.1, ZP_04890914.1, ZP_04891982.1, ZP_04893793.1, ZP_04902131.1, ZP_04905327.1, ZP_04941068.1, ZP_04944536.1, ZP_04945255.1, ZP_04959332.1, ZP_04964181.1, ZP_05053721.1, ZP_05063588.1, ZP_05073059.1, ZP_05077806.1, ZP_05082750.1, ZP_05091128.1, ZP_05095488.1, ZP_05101701.1, ZP_05116783.1, ZP_05121836.1, ZP_05127756.1, ZP_05637806.1, ZP_05742087.1, ZP_05783548.1, ZP_05786246.1, ZP_05843149.1, ZP_05945960.1, ZP_06459045.1, ZP_06487195.1, ZP_06492453.1, ZP_06493162.1, ZP_06703644.1, ZP_06731146.1, ZP_06839371.1, ZP_07007312.1, ZP_07266194.1, ZP_07374050.1, ZP_07662787.1, ZP_07778196.1, ZP_07797983.1, ZP_08099459.1, ZP_08138203.1, ZP_08141719.1, ZP_08142973.1, ZP_08177102.1, ZP_08185821.1, ZP_08186468.1, ZP_08208888.1, ZP_08266590.1, ZP_08402041.1, ZP_08406891.1, ZP_08522175.1, ZP_08527488.1, ZP_08631252.1, ZP_08636687.).

In another preferred embodiment, the cell of the invention or used in the process of the invention may expresse an alanine dehydrogenase. In a preferred embodiment, the term "alanine dehydrogenase", as used herein, means an enzyme catalysing the conversion of L-alanine, with consumption of water and $NAD^+$, to pyruvate, ammonia and NADH. For example, use may be made of the alanine dehydrogenases from the group comprising alanine dehydrogenase of *Bacillus subtilis* (database code L20916), *Rhizobium leguminosarum* (database code CP001622), *Vibrio proteolyticus* (database code AF070716), *Mycobacterium tuberculosis* (database code X63069), *Enterobacter aerogenes* (database code AB013821), EGR93259.1, YP_003654745.1, YP_003651439.1, YP_003637111.1, YP_003631815.1, YP_001327051.1, YP_001262560.1, YP_886996.1, YP_882850.1, YP_704410.1, YP_703508.1, ZP_08624689.1, YP_001230376.1, P17557.1, P17556.1, CCB94892.1, CCB73698.1, YP_001168635.1, YP_004668736.1, YP_004569425.1, YP_003513168.1, YP_004561169.1, ZP_08554945.1, YP_400777.1, ZP_08311476.1, ZP_08310170.1, ZP_08267322.1, ZP_08263846.1, ZP_07898723.1, YP_149301.1, YP_148605.1, YP_004340432.1, EFT09946.1, EFS80513.1, EFS51332.1, EFS42459.1, YP_003060895.1, YP_003059033.1, ZP_03305373.1, YP_847214.1, YP_004095847.1, YP_003338282.1, YP_003337256.1, YP_355846.1, YP_253131.1, ZP_08197563.1, ZP_08196283.1, ADW06447.1, YP_734091.1, NP_372233.1, NP_102173.1, ZP_08170259.1, EGD36706.1, EGD32748.1, ZP_08155540.1, YP_004142849.1, YP_002417649.1, YP_001301040.1, YP_002992892.1, YP_081348.1, YP_080482.1, YP_002476349.1, ZP_08115025.1, ZP_08114403.1, YP_003552869.1, YP_002358112.1, YP_575010.1, YP_477594.1, YP_474564.1, YP_130399.1, YP_129373.1, YP_123314.1, NP_810467.1, NP_646469.1, NP_626044.1, NP_391071.1, ZP_08086822.1, ZP_08084776.1, ZP_08083119.1, ZP_08020768.1, ZP_08013590.1, ZP_08011832.1, YP_003783744.1, YP_002781576.1, YP_002780533.1, ZP_02195873.1, NP_797482.1, ZP_07645051.1, ZP_07643260.1, ZP_06611917.1, AAT40119.1, ZP_07864946.1, YP_004068409.1, YP_002796203.1, YP_002774420.1, YP_003600348.1, YP_003599946.1, YP_003565624.1, YP_003565223.1, YP_335198.1, YP_423850.1, YP_155059.1, ZP_07843538.1, ZP_07841226.1, ZP_06928932.1, ZP_05692073.1, ZP_05687006.1, YP_04867480.1, YP_775531.1, CBE70214.1, YP_07721182.1, ZP_04302850.1, ZP_04298961.1, ZP_04287684.1, ZP_04277177.1, ZP_04248389.1, ZP_04235899.1, ZP_02159718.1, ZP_02152178.1, YP_003974610.1, YP_003546595.1, YP_002317127.1, ZP_07313778.1, ZP_07302778.1, ZP_07298850.1, CBK69442.1, YP_003413835.1, YP_003595089.1, ZP_06807811.1, YP_003582455.1, YP_003464731.1, YP_003496397.1, YP_003421918.1, CBL07274.1, CBK64956.1, YP_003508515.1, AAL87460.1, AAC23579.1, AAC23578.1, AAC23577.1, ACU78652.1, YP_003471439.1, YP_003452777.1, ZP_06384971.1, ACY25368.1, ABC26869.1, AAP44334.1, EEZ80018.1, ZP_05110458.1, 1PJB_A, ZP_04717201.1, ZP_04689103.1, CAO90307.1, CAM75354.1, CAA44791.1, BAA77513.1, EGR96638.1, EGL90046.1, YP_004510847.1, ZP_08450330.1, YP_003387804.1, YP_003058152.1, EFS74272.1, EFS67128.1, ZP_06844564.1, YP_826658.1, YP_001195249.1, YP_003095978.1, YP_469292.1, YP_004442054.1, YP_004461174.1, YP_004055616.1, YP_003576656.1, YP_003094537.1, YP_001295973.1, AEE71143.1, YP_004447480.1, YP_003761844.1, YP_040853.1, YP_003154888.1, YP_003142045.1, YP_002280953.1, NP_371963.1, NP_422368.1, EGC98966.1, EGC76398.1, YP_004263661.1, YP_004252039.1, YP_679036.1, YP_499973.1, ZP_08054972.1, ZP_08053009.1, ZP_04067276.1, ZP_03968868.1, ZP_03963857.1, ZP_03933079.1, ZP_03497046.1, ZP_06668924.1, ZP_06667106.1, ZP_06324464.1, ZP_06196777.1, ZP_05114159.1, ZP_05083968.1, ZP_05070370.1, ZP_05030022.1, ZP_04673064.1, ZP_03517011.1, ZP_03505783.1, XP_001310698.1, ABK27691.1 or CAB59281.2.

It may be advantageous in the case of the cell expressing an alanine dehydrogenase to add a sufficient amount of an inorganic nitrogen source, preferably an ammonium salt such as ammonium chloride or ammonium sulphate, to the aqueous solution. A method of increasing the concentration of alanine is described in EP12162846.5.

One aspect of the present invention provides for the use of a knockout of a gene coding for a polypeptide comprising SEQ ID NO: 2 or a variant thereof as part of the genetic make-up of a recombinant cell for increasing production of a carboxylic acid ester of the formula (I). This means that the knockout of a gene coding for a polypeptide comprising SEQ ID NO: 2 or a variant thereof as a feature of the cell was carried out for the purpose of increasing the yield, carbon and/or nitrogen balance and/or purity of the product of reacting the carboxylic acid ester of the formula (I).

In a most preferred embodiment, the invention provides for a cell which may be an *E. coli* cell having a knockout of the polypeptide comprising SEQ ID NO: 2 or a variant thereof and of the polypeptide FadL in the cell's genome, with said cell furthermore expressing an alkane hydroxylase, preferably *Pseudomonas putida* AlkB, a transaminase, preferably the transaminase of *Chromobacterium violaceum* ATCC 12472, an alanine dehydrogenase, preferably *Bacillus subtilis* alanine dehydrogenase, and *Pseudomonas putida* AlkL. In another most preferred embodiment, said cell may be contacted with a fatty acid ester, preferably methyl dodecanoate, in an aqueous solution.

Having generally described this invention, a further understanding can be obtained by reference to certain specific examples which are provided herein for purposes of illustration only and are not intended to be limiting unless otherwise specified.

FIGURES

FIG. 1 depicts the omega-amino-dodecanoic acid productivity of various strains.

Example 1

Inactivation of bioH in *E. coli* W3110 and BW25113

A new plasmid was needed to specifically knock out the bioH gene (b3412, SEQ ID NO:1) using the basis vector pKO3_E933. This was based on the pKO3_E933 vector (SEQ ID NO: 14), with 500 bp being inserted upstream (SEQ ID NO: 3) and 500 bp being inserted downstream of the bioH gene (SEQ ID NO: 4), separated by a PspXI cleavage site (CCTCGAGG). The finished plasmid was internally referred to as AHp-LL-42 (SEQ ID NO: 5). To finish, the following oligonucleotides were used:

```
o-LL-314,
                                          SEQ ID NO: 6
5'-CCGGGGATCGCGGCCCGGCTTCGCTATCCCATTGGCAGT-3' o-LL-315,
                                          SEQ ID NO: 7
5'-CCTCTGCTTCAACGCCCTCGAGGCATCCGCTATTGTTCTCTT

TTGACTTACAAGGATG-3' o-LL-316,
                                          SEQ ID NO: 8
5'-GCGTTGAAGCAGAGGGTGTAGGTG-3' o-LL-317,
                                          SEQ ID NO: 9
5'-TAGAGGATCGCGGCCCAAACTGGCAAGGCAGCTTTATGC-3'
```

The 500 bp regions were provided using the above primers from available chromosomal DNA of *E. coli* W3110 by means of polymerase chain reaction (PCR), with o-LL-314+o-LL-315 were used for the upstream region (SEQ ID 3) and o-LL-316+o-LL-317 were used for the downstream region (SEQ ID 4). The following parameters were applied to the PCR:

Initial denaturation: 98° C., 10 s
30× Denaturation: 98° C., 10 s
30× Annealing: 57.9/58.8/59.7/60.6/61.4/62.3/63.2/64.1° C. (temperature gradient)
30× Elongation: 72° C., 20 s
Final elongation: 72° C., 4 min For multiplication, the 2× Phusion HF Master Mix from New England Biolabs (NEB, M0531S) was used according to the manufacturer's information. Depending on the degree of purity, the PCR products were directly column-purified (*QiaQuick PCR Purification Kit*, Qiagen, Hilden) or purified via an agarose gel and extracted (*QiaQuick Gel Extraction Kit*, Qiagen, Hilden, Germany). PCR, agarose gel electrophoresis, ethidium bromide staining of the DNA and determination of PCR fragment sizes were carried out in the manner known to the skilled worker. It was possible in both cases to provide PCR fragments of the expected size.

The purified PCR products were cloned into the NotI-cut pKO3_E933 vector (SEQ ID 14) by means of recombination using the In-Fusion HD Cloning Kit according to the manufacturer's instruction (Clontech Laboratories Inc., Mountain View, Calif., USA). Chemically competent *E. coli* DH10β (New England Biolabs, Frankfurt, Germany) were transformed in the manner known to the skilled worker. Correct insertion of the target sequences was checked by restriction analysis, and authenticity of the introduced sequences was confirmed by DNA sequencing. The resulting vector was referred to as AHp-LL-42 (SEQ ID NO: 5).

The strain *E. coli* W3110 ΔbioH was constructed with the aid of the vector AHp-LL-42 (SEQ ID 5) by methods known to the skilled worker (see Link A J, Phillips D, Church G M. J. Bacteriol. 1997. 179(20).). The strains used in the experiments, BW25113 and BW25113 ΔbioH (JW3375), were purchased commercially as part of the Keio collection (see Construction of *Escherichia coli* K-12 in-frame, single-gene knockout mutants: the Keio collection, Tomoya Baba, Takeshi Ara, Miki Hasegawa, Yuki Takai, Yoshiko Okumura, Miki Baba, Kirill A Datsenko, Masaru Tomita, Barry L Wanner and Hirotada Mori, Molecular Systems Biology (2006), 2006 EMBO and Nature Publishing Group). The strain constructed was subsequently referred to as:

| Strain | Description |
| --- | --- |
| AHs-LL-56 | *E. coli* W3110 ΔbioH, clone 1.1 |

The DNA sequence of bioH after deletion in W3110 is indicated in SEQ ID 10.

Example 2

Production of methyl amino-dodecanoate by *E. coli* W3110 Containing a Deletion in the bioH Gene by Employing Expression Vectors for the Genes *Bacillus subtilis* ald and *Chromobacterium violaceum* Cv_2025 in Combination with an Expression Vector for the alkB, alkG, alkT and alkL Genes of the *Pseudomonas putida* alk Operon.

The *E. coli* strains containing expression vectors for the genes *Bacillus subtilis* ald (coding for an alanine dehydrogenase, codon-optimized for *E. coli*), *Chromobacterium violaceum* Cv_2025 (coding for a transaminase, codon-optimized for *E. coli*) in combination with an expression vector for the alkB, alkG, alkT (coding for an alkane monooxygenase, a rubredoxin and a rubredoxin reductase) and alkL (coding for a membrane/transport protein) genes of the *Pseudomonas putida* alk operon were generated by preparing electro-competent *E. coli* W3110 ΔbioH cells and the corresponding *E. coli* W3110 control strain. This was carried out in a manner known to the skilled worker. The strains were prepared as described in Example 1. They were transformed with plasmids pBT10_alkL (SEQ ID NO: 11 or WO/2011/131420 and Seq ID NO: 8 listed there) and pJ294[alaDH_Bs(co)TA_Cv(co)] (SEQ ID 12 or Example 1 of WO/2013/024114 and SEQ ID NO: 17 listed there) and plated on LB-agar plates containing kanamycin (50 µg/ml) and ampicillin (100 µg/ml). Transformants were checked with regard to the presence of the correct plasmids by plasmid preparation and analytical restriction analysis. In this way, the following strains were constructed:

| Strain background | Plasmids present |
| --- | --- |
| W3110 | pBT10_alkL |
|  | pJ294[alaDH_Bs(co)TA_Cv(co)] |
| W3110 ΔbioH | pBT10_alkL |
|  | pJ294[alaDH_Bs(co)TA_Cv(co)] |

The strains were subjected to fed-batch fermentation, in order to analyze the capacity for producing methyl hydroxy-dodecanoate, methyl oxo-dodecanoate, methyl carboxy-dodecanoate and methyl amino-dodecanoate from methyl dodecanoate. This was carried out using an 8-fold parallel fermentation system from DASGIP.

The fermentation was carried out using 11-reactors. The pH probes were calibrated by means of a two-point calibration using standard solutions of pH 4.0 and pH 7.0. The reactors were charged with 300 ml of tap water and autoclaved at 121° C. for 20 min in order to ensure sterility. The pO2 probes were then polarized on the DASGIP system overnight (at least for 6 h). The next morning, the water was removed at the clean bench and replaced with 300 ml of high cell-density medium containing 100 mg/l ampicillin, 50 mg/l kanamycin and 5 mg/l tetracycline. This was followed by calibrating the pO2 probes using a one-point calibration (stirrer: 400 rpm/gassing: 10 sL/h air) and cleaning the feed, correcting agent and inducer lines by means of Clean-in-Place. For this purpose, the tubings were rinsed with 70% ethanol, followed by 1 M NaOH, then with sterile deionized water and finally filled with the respective media.

The ALS- and ALSME-producing *E. coli* strains were first grown from the respective frozen stocks in LB medium (25 ml in a 100 ml baffled flask) containing 100 mg/l ampicillin at 37° C. and 200 rpm overnight for approx. 18 h. In each case 2 ml of the cultures were then transferred to high cell-density medium (glucose 15 g/l (30 ml/l of a separately autoclaved 500 g/l stock solution containing 1% $MgSO_4*7H_2O$ and 2.2% $NH_4Cl$), $(NH_4)_2SO_4$ 1.76 g/l, $K_2HPO_4$ 19.08 g/l, $KH_2PO_4$ 12.5 g/l, yeast extract 6.66 g/l, trisodium citrate dihydrate 2.24 g/l, ammonium iron citrate solution 17 ml/l of a separately autoclaved 1% strength stock solution, trace element solution 5 ml/l separately autoclaved stock solution (HCl (37%) 36.50 g/l, $MnCl_2*4H_2O$ 1.91 g/l, $ZnSO_4*7H_2O$ 1.87 g/l, ethylenediaminetetraacetic acid dihydrate 0.84 g/l, $H_3BO_3$ 0.30 g/l, $Na_2MoO_4*2H_2O$ 0.25 g/l, $CaCl_2*2H_2O$ 4.70 g/l, $FeSO_4*7H_2O$ 17.80 g/l, $CuCl_2*2H_2O$ 0.15 g/l)) (per strain 25 ml in a 100 ml baffled flask) containing 100 mg/l ampicillin, 50 mg/l kanamycin and 5 mg/l tetracycline and incubated at 37° C./200 rpm for another 5.5 h.

The reactors were inoculated with an optical density of 0.1 by drawing a corresponding volume of the pre-culture into a 5 ml syringe (under sterile conditions) and inoculating the reactors by means of a cannula via a septum overlaid with 70% ethanol.

The following standard program was used:

The experiment carried out was divided into two phases, growth, during which the cells ought to reach a particular optical density, and subsequent biotransformation, during which, after addition of the substrate methyl dodecanoate, a reaction by enzymes formed during expression to give amino-dodecanoate ought to take place. The pH values were adjusted one-sidedly with ammonia (12.5%) to pH 6.8. During growth and biotransformation, dissolved oxygen (DO) in the culture was controlled via stirrer revolution and gassing rate to be at 30%. Fermentation was carried out by way of fed batch, with feed start, 5 g/lh glucose feed (500 g/l glucose containing 1% $MgSO_4*7H_2O$ and 2.2% $NH_4Cl$), being triggered via a DO peak. Also, with feed start, the temperature was lowered from 37° C. before to 30° C. Expression of transaminase, alanine dehydrogenase and fatty acid reductase was induced by automated addition of IPTG (1 mM) 2 h after feed start. The alk genes were induced by manually adding DCPK (0.025 Vol.-%) 10 h after feed start. The optical density of the culture broths was determined before the start of biotransformation.

The biotransformation phase was started 14 h after feed start. For this purpose, 150 ml of a mixture of methyl dodecanoate and the ion exchanger oleic acid (technical grade, 90%) were added as batch to the fermentation broth. In order to provide an amino group donor for the transaminase, 5 ml of a 3 M ammonium sulphate solution were added to the fermentation broth half an hour before the start of biotransformation. Samples were taken by removing 2 ml of fermentation broth from the tank and diluting a portion thereof 1/20 in an acetone/HCl mixture (c(HCl)=0.1 mol/l) and extracting it. Samples were taken from all reactors 1 h, 2 h, 3 h, 4 h, 5 h, 7.5 h, 10.5 h, 19.5 h and 21 h after the start of biotransformation. The transfer rates for oxygen (OTR=oxygen transfer rate) and carbon (CTR=carbon transfer rate) were determined by off-gas analysis on the DASGIP systems during fermentation. Fermentation was stopped 21 h after the start of biotransformation. Stirrer, gassing, and temperature and pH controls were switched off and the tanks were left standing still for 5-10 minutes.

To quantify DDS (C12-di-carboxylic acid), DDSME (C12-di-carboxylic acid methyl ester), LS (dodecanoic acid [Laurinsäure]), LSME (methyl dodecanoate [Laurinsäure-Methylester]), HLS (omega-hydroxy-dodecanoic acid [omega-Hydroxy-Laurinsäure]), HLSME (methyl omega-

| | DO Control | | pH Control | |
|---|---|---|---|---|
| Preset | 0% | Preset | | 0 ml/h |
| P | 0.1 | P | | 5 |
| Ti | 300 s | Ti | | 200 s |
| min | 0% | min | | 0 ml/h |
| max | 100% | max | | 40 ml/h |

| N (rotation) | from | to | XO2 (gas mixture) | from | to | F (gas flow) | from | to |
|---|---|---|---|---|---|---|---|---|
| Growth and biotransformation | 0% | 30% | Growth and biotransformation | 0% | 100% | Growth and biotransformation | 15% | 80% |
| | 400 rpm | 1500 rpm | formation | 21% | 21% | formation | 6 sL/h | 72 sL/h |

| Script | |
|---|---|
| Trigger set | 31% DO (1/60 h) |
| Induction IPTG | 2 h after feed start |
| Feed trigger | 50% DO |
| Feed rate | 3 [ml/h] | hydroxy-dodecanoate [omega-Hydroxy-Laurinsäure-Methylester]), OLS (omega-oxo-dodecanoic acid [omega-Oxo-Laurinsäure]), OLSME OLS (methyl omega-oxo-dodecanoate [omega-Oxo-Laurinsäure-Methylester]), ALS (omega-amino-dodecanoic acid [omega-Amino-Laurinsäure]) and ALSME (methyl omega-amino-dodecanoate [omega-Amino-Laurinsäure-Methylester]) in fermentation samples, samples were removed during culturing. These samples were prepared for analysis. (see LC-ESI/MS$^2$-based quantification of products).

LC-ESI/MS$^2$-Based Quantification of Products

Quantification of ALS, ALSME, DDS, DDSME, LS, LSME, HLS, HLSME, OLS and OLSME in fermentation samples was carried out by means of LC-ESI/MS$^2$ on the basis of an external calibration for all analytes (0.1-50 mg/L) and by using the internal standards amino-undecanoic acid (AUD, for HLS, DDS, OLS, HLSME, OLSME), d4-ALSME (for ALSME), $^{13}$C-DDSME (for DDSME), d3-LS (for LS) and d3-LSME (for LSME).

The following instruments are used:
HPLC system 1260 (Agilent; Böblingen, Germany) with autosampler (G1367E), binary pump (G1312B) and thermo-statted column (G1316A)
Mass spectrometer TripelQuad 6410 (Agilent; Böblingen, Germany) with ESI source
HPLC column: Kinetex C18, 100×2.1 mm, particle size: 2.6 μm, pore size 100 Å (Phenomenex; Aschaffenburg, Germany)
Pre-column: KrudKatcher Ultra HPLC In-Line Filter; 0.5 μm filter depth and 0.004 mm inner diameter (Phenomenex; Aschaffenburg, Germany)

The samples were prepared by pipetting 1900 μl of solvent (80% (v/v) ACN, 20% double-distilled H$_2$O (v/v), +0.1% formic acid) and 100 μl of sample into a 2 ml reaction vessel. The mixture was vortexed for approx. 10 seconds and then centrifuged at approx. 13 000 rpm for 5 min. The clear supernatant was removed using a pipette and analysed after appropriate dilution with a diluent (80% (v/v) ACN, 20% double-distilled H$_2$O (v/v), +0.1% formic acid). In each case, 100 μl of ISTD were added to 900 μl of sample (10 μl with a sample volume of 90 μl).

HPLC separation was carried out using the above-mentioned column and pre-column. The injection volume is 0.7 the column temperature is 50° C., the flow rate is 0.6 ml/min. The mobile phase consists of eluent A (0.1% strength (v/v) aqueous formic acid) and eluent B (acetonitrile with 0.1% (v/v) formic acid). The following gradient profile was utilized:

| Time [min] | Eluent A [%] | Eluent B [%] |
|---|---|---|
| 0 | 77 | 23 |
| 0.3 | 77 | 23 |
| 0.4 | 40 | 60 |
| 2.5 | 40 | 60 |
| 2.6 | 2 | 98 |
| 5.5 | 2 | 98 |
| 5.6 | 77 | 23 |
| 9 | 77 | 23 |

ESI-MS$^2$ analysis was carried out in positive mode with the following parameters of the ESI source:
Gas temperature 280° C.
Gas flow 11 l/min
Nebulizer pressure 50 psi
Capillary voltage 4000 V Detection and quantification of the compounds ALS, ALSME, DDS, DDSME, HLS, HLSME, OLS, OLSME were carried out with the following MRM parameters, with in each case one product ion being utilized as qualifier and one being utilized as quantifier:

| Analyte | Precursor ion [m/z] | Product ion [m/z] | Dwell time [ms] | Collision energy [eV] |
|---|---|---|---|---|
| DDSME | 245.2 | 167.1 | 25 | 6 |
| DDSME | 245.2 | 149.1 | 50 | 8 |
| HLSME | 231.3 | 181.2 | 15 | 2 |
| HLSME | 231.3 | 163.2 | 25 | 5 |
| DDS | 231.2 | 213.2 | 50 | 0 |
| DDS | 231.2 | 149.1 | 25 | 9 |
| ALSME | 230.3 | 198.1 | 25 | 10 |
| ALSME | 230.3 | 163.2 | 15 | 10 |
| OLSME | 229.2 | 197.2 | 50 | 0 |
| OLSME | 229.2 | 161.1 | 25 | 5 |
| HLS | 217.2 | 181.2 | 35 | 0 |
| HLS | 217.2 | 163.1 | 20 | 4 |
| OLS | 215.2 | 161.2 | 25 | 0 |
| OLS | 215.2 | 95.2 | 60 | 13 |

The analytes LS and LSME were detected in SIM mode (m/z 201 and 215).

Results

Reduced Formation of the Free Acids amino-dodecanoic Acid, dodecanedioic Acid and dodecanoic Acid After Knockout of bioH in E. coli W3110

The strain with bioH knockout exhibited markedly reduced formation of the free acids amino-dodecanoic acid, dodecanedioic acid and dodecanoic acid compared to the control strain with intact bioH. The ratios of the absolute end titres of dodecanedioic acid (DDS) and dodecanedioic acid methyl ester (DDSME), amino-dodecanoic acid (ALS) and methyl amino-dodecanoate (ALSME), and dodecanoic acid (LS) and methyl dodecanoate (LSME) were calculated and are expressed in percent.

| | End titre in g/l | | | | | |
|---|---|---|---|---|---|---|
| | ALS | ALSME | DDS | DDSME | LS | LSME |
| W3110 | 0.12 | 11.77 | 5.02 | 7.27 | 0.03 | 1.91 |
| W3110 ΔbioH | 0.01 | 11.82 | 0.23 | 2.35 | 0.03 | 12.92 |

| | Free acid/methyl ester ratio in percent | | |
|---|---|---|---|
| | ALS/ALSME | DDS/DDSME | LS/LSME |
| W3110 | 0.98 | 69.12 | 1.79 |
| W3110 ΔbioH | 0.10 | 9.74 | 0.24 |

| | Free acid/methyl ester ratio in percent | | |
|---|---|---|---|
| | ALS/ALSME | DDS/DDSME | LS/LSME |
| W3110 to W3110 ΔbioH | 9.75 | 7.10 | 7.57 |

The effect of the bioH knockout on the formation of free acids became clearly visible and was between a reduction by around a factor of 7.10 (DDS/DDSME) up to a factor of 9.75 (ALS/ALSME).

Improved Product/Secondary Product Ratio After Knockout of bioH in E. coli W3110

The absolute titres attained after a fixed time (=end of biotransformation) were evaluated. The strain background W3110 ΔbioH exhibited a markedly improved ratio of products (ALS and ALSME) to major secondary products (DDS and DDSME), with the final product titre remaining the same. The ratio increased from 49.17% ALS(ME) to 82.10% ALS(ME).

|  | Concentration in g/l | | Ratio of ALS(ME) to |
| --- | --- | --- | --- |
|  | ALS + ALSME | DDS + DDSME | ALS(ME) + DDS(ME) in percent |
| W3110 | 11.89 | 12.29 | 49.17 |
| W3110 ΔbioH | 11.83 | 2.58 | 82.10 |

Example 3

Production of methyl amino-dodecanoate by an *E. coli* Strain Having a Deletion in the bioH Gene by Employing an Expression Vector for the Genes *Bacillus subtilis* ald and *Chromobacterium violaceum* Cv_2025 and the alkB, alkG, alkT and alkL Genes of the *Pseudomonas putida* alk Operon The *E. coli* strains containing an expression vector for the genes *Bacillus subtilis* ald (coding for an alanine dehydrogenase, codon-optimized for *E. coli*), *Chromobacterium violaceum* Cv_2025 (coding for a transaminase, codon-optimized for *C. tropicalis*), alkB, alkG, alkT (coding for an alkane monooxygenase, a rubredoxin and a rubredoxin reductase) and alkL (coding for a membrane/transport protein) of the *Pseudomonas putida* alk operon were generated by preparing electro-competent *E. coli* BW25113 ΔbioH cells and the corresponding *E. coli* BW25113 control strain. This took place in a manner known to the skilled worker. The strains are from the commercially available Keio collection. They were transformed with plasmid pACYC184{MCS2.0}[alkST_BFGL][alaDH_Bs(co){PspXI} TAcv(ct)] (SEQ ID NO: 13 and Example 1 of WO/2013/024114 and SEQ ID NO: 17 listed there) and plated on LB-agar plates containing chloramphenicol (50 µg/ml). Transformants were checked with regard to the presence of the correct plasmids by plasmid preparation and analytical restriction analysis. In this way, the following strains were constructed:

| Strain background | Plasmids present |
| --- | --- |
| BW25113 | pACYC184{MCS2.0}[alkST_BFGL][alaDH_Bs(co){PspXI} TAcv(ct)] |
| BW25113 ΔbioH | pACYC184{MCS2.0}[alkST_BFGL][alaDH_Bs(co){PspXI} TAcv(ct)] |

The strains were subjected to fed-batch fermentation, in order to analyze the capacity for producing methyl hydroxy-dodecanoate, methyl oxo-dodecanoate, methyl carboxy-dodecanoate and methyl amino-dodecanoate from methyl dodecanoate. This was carried out using an 8-fold parallel fermentation system from DASGIP. Further experimental procedures were exactly as described in Example 2.

Results

Reduced Formation of the Free Acids amino-dodecanoic Acid, dodecanedioic Acid, dodecanoic Acid and hydroxy-dodecanoic Acid After Knockout of bioH in *E. coli* BW25113

The strain with bioH knockout exhibited markedly reduced formation of the free acids amino-dodecanoic acid, dodecanedioic acid, dodecanoic acid and hydroxy-dodecanoic acid compared to the control strain with intact bioH, in part below the detection limit. The ratios of the absolute end titres of dodecanedioic acid (DDS) and dodecanedioic acid methyl ester (DDSME), amino-dodecanoic acid (ALS) and methyl amino-dodecanoate (ALSME), hydroxy-dodecanoic acid (HLS) and methyl hydroxy-dodecanoate (HLSME), and dodecanoic acid (LS) and methyl dodecanoate (LSME) were calculated and are expressed in percent.

|  | Titre in g/l | | | | | | | |
| --- | --- | --- | --- | --- | --- | --- | --- | --- |
|  | ALS | ALSME | DDS | DDSME | HLS | HLSME | LS | LSME |
| BW25113 | 0.16 | 10.80 | 2.75 | 1.40 | 0.72 | 15.01 | 0.48 | 40.77 |
| BW25113 ΔbioH | n.d. | 15.86 | 0.23 | 3.95 | n.d. | 12.32 | n.d. | 28.49 |

The DDS/DDSME ratio is the only one that can be presented mathematically:

|  | DDS/DDSME in percent |
| --- | --- |
| BW25113 | 196.94 |
| BW25113 ΔbioH | 5.87 |

The bioH knockout reduced DDS formation by a factor of 33.5, with all other free acids being below the lower detection limit.

Extended Oxidation Phase After Knockout of bioH in *E. coli* BW25113

It turned out that, compared to the control strain, the initial oxidation performance did not decline in the bioH-knockout strain but remained nearly constant with respect to ALSME formation throughout the process.

|  | Process time [h] | ALSME [g/l] |
| --- | --- | --- |
| BW25113 | 1 | 0.26 |
|  | 2 | 1.16 |
|  | 3 | 2.35 |
|  | 19 | 10.51 |
|  | 21.25 | 10.80 |
| BW25113 ΔbioH | 1 | 0.38 |
|  | 2 | 1.27 |
|  | 3 | 2.48 |
|  | 19 | 14.94 |
|  | 21.25 | 15.86 |

FIG. 1 shows: The bioH knockout effected an increase in productivity by 47% based on the end titre under the same conditions.

Increased Rate of Formation of methyl amino-dodecanoate After Knockout of bioH in *E. coli* BW25113

The absolute titres attained after a fixed time (=end of biotransformation) were evaluated. Here, the knockout strain displayed a distinctly higher rate of product formation of 0.75 g of ALSME per litre and hour over 0.51 g of ALSME per litre and hour in the wild-type strain.

| | Process time [h] | ALSME [g/l] |
|---|---|---|
| BW25113 | 21.25 | 10.80 |
| BW25113 ΔbioH | 21.25 | 15.86 |

Improved Product/Secondary Product Ratio After Knockout of bioH in *E. coli* BW25113

The absolute titres attained after a fixed time (=end of biotransformation) were evaluated. Here, the knockout strain background displayed a markedly improved ratio of product (ALS and ALSME) to major secondary product (DDS and DDSME).

| | Titre in g/l | | | |
|---|---|---|---|---|
| | ALS | ALSME | DDS | DDSME |
| BW25113 | 0.16 | 10.80 | 2.75 | 1.40 |
| BW25113 ΔbioH | 0.00 | 15.86 | 0.23 | 3.95 |

| | ALS + ALSME [g/l] | DDS + DDSME [g/l] |
|---|---|---|
| BW25113 | 10.96 | 4.15 |
| BW25113 ΔbioH | 15.86 | 4.18 |

| | ALS(ME)/DDS(ME) |
|---|---|
| BW25113 | 2.64 |
| BW25113 ΔbioH | 3.80 |

The ratio increased by 43.9% due to bioH knockout. The product titre increased by 43.9%, with the secondary-product titre remaining the same.

Increased Glucose Yield Coefficient ($Y_{P/S}$) for Production of amino-dodecanoic Acid and methyl amino-dodecanoate After Knockout of bioH in *E. coli* BW25113

The final cumulated absolute titres of amino-dodecanoic acid and methyl amino-dodecanoate were evaluated in comparison to the amount of glucose used.

| | ALS + ALSME [g/l] | Glucose consumption [g] | g/l ALS(ME) per g of glucose |
|---|---|---|---|
| BW25113 | 10.96 | 52.95 | 0.21 |
| BW25113 ΔbioH | 15.86 | 52.55 | 0.30 |

The glucose yield coefficient increased from 0.21 g/l ALS(ME) per gram of glucose by 46% to 0.30 g/l ALS(ME) per gram of glucose as a result of the bioH knockout.

Numerous modifications and variations on the present invention are possible in light of the above description and examples. It is therefore to be understood that within the scope of the following Claims, the invention may be practiced otherwise than as specifically described herein. Any such embodiments are intended to be within the scope of the present invention.

The invention claimed is:

1. A process for transforming a carboxylic acid ester of the formula (I) into a second carboxylic acid ester:

$$R^1\text{-A-COOR}^2 \qquad (I),$$

where
R$^1$ is hydrogen, —CH$_2$OH, —CHO, —COORS, —CH$_2$SH, —CH$_2$OR$^3$ or —CH$_2$NH$_2$,
R$^2$ is an alkyl group,
R$^3$ is hydrogen or an alkyl group, and
A is an unsubstituted, a linear, or an unsubstituted and linear alkylene radical having at least 10 carbons,
the process comprising:
contacting a recombinant cell with the carboxylic acid ester of the formula (I) in an aqueous solution to convert the carboxylic acid ester of the formula (I) to the second carboxylic acid ester, wherein the recombinant cell has a reduced activity of a polypeptide comprising SEQ ID NO: 2 or a polypeptide having at least 70% homology to SEQ ID NO:2 and having essentially the same enzymatic activity as the polypeptide comprising SEQ ID NO:2 compared to an activity in a corresponding wild-type cell due to knock-out of a gene encoding the polypeptide comprising SEQ ID NO:2 or the polypeptide having at least 70% homology to SEQ ID NO:2 and having essentially the same enzymatic activity as the polypeptide comprising SEQ ID NO:2, the recombinant cell comprises a polypeptide having at least 80% sequence identity to consecutive 230 amino acids of SEQ ID NO: 15 and having essentially the same enzymatic activity as *Pseudomonas putida* AlkL, where the polypeptide is optionally overexpressed, the recombinant cell has been transformed to express a transaminase, *Pseudomonas putida* AlkBGT, and an alanine dehydrogenase, the recombinant cell has a reduced activity of at least one enzyme catalyzing any of reactions of fatty acid β-oxidation compared to an activity in the wild-type cell due to knockout, and the at least one enzyme catalyzing any of reactions of fatty acid β-oxidation is selected from the group consisting of fatty acid-CoA ligase, acyl-CoA dehydrogenase, 2,4-dienoyl-CoA reductase, enoyl-CoA hydratase, 3-ketoacyl-CoA thiolase, and a fatty acid importer.

2. The process according to claim 1, further comprising: contacting the aqueous solution with a hydrophobic organic solution comprising a cation exchanger.

3. The process of claim 1, wherein
$R^2$ is methyl, ethyl or propyl,
$R^3$ is methyl, ethyl or propyl, and
A is an unsubstituted, a linear, or an unsubstituted and linear alkylene radical having 11 carbons.

4. The process according to claim 1, wherein A is an unsubstituted and linear alkylene radical.

5. The process according to claim 1, wherein $R^1$ is hydrogen, —CH$_2$OH, —CHO or —CH$_2$NH$_2$.

6. The process according to claim 1, wherein A is an alkylene radical of formula —(CH$_2$)$_n$—, where n is at least 10.

7. The process according to claim 1, wherein the second carboxylic acid ester has the formula (I'):

$$R^1\text{-A-COOR}^2 \qquad (I'),$$

where
$R^1$ is hydrogen, —CH$_2$OH, —CHO, —COORS, —CH$_2$SH, —CH$_2$OR$^3$ or —CH$_2$NH$_2$,
$R^2$ is an alkyl group,
$R^3$ is hydrogen or an alkyl group, and
A is an unsubstituted, a linear, or an unsubstituted and linear alkylene radical having at least 10 carbons.

8. The process according to claim 1, wherein the carboxylic acid ester of the formula (I) is methyl dodecanoate.

9. The process according to claim 1, wherein the second carboxylic acid ester comprises methyl 12-amino-dodecanoate.

10. The process according to claim 1, wherein the at least one enzyme catalyzing any of reactions of fatty acid β-oxidation comprises at least one of FadA, FadB, FadD, FadL, and FadE from *Escherichia coli*.

11. The process according to claim 1,
wherein $R^1$ is hydrogen, —CH$_2$OH, —CHO or —CH$_2$NH$_2$,
$R^2$ is methyl, ethyl or propyl, and
A is an alkylene radical of formula —(CH$_2$)$_n$—, where n is at least 10.

12. The process according to claim 1,
wherein the cell has a reduced activity of a polypeptide comprising SEQ ID NO: 2 or a polypeptide having at least 90% homology to SEQ ID NO:2 and having essentially the same enzymatic activity as the polypeptide comprising SEQ ID NO:2 compared to an activity in a corresponding wild-type cell due to knockout of a gene encoding the polypeptide comprising SEQ ID NO:2 or the polypeptide having at least 90% homology to SEQ ID NO:2 and having essentially the same enzymatic activity as the polypeptide comprising SEQ ID NO:2, and the recombinant cell comprises a polypeptide having at least 90% sequence identity to consecutive 230 amino acids of SEQ ID NO: 15 and having essentially the same enzymatic activity as *Pseudomonas putida* AlkL.

13. The process according to claim 1,
wherein the cell has a reduced activity of a polypeptide comprising SEQ ID NO: 2 or a polypeptide having at least 96% homology to SEQ ID NO:2 and having essentially the same enzymatic activity as the polypeptide comprising SEQ ID NO:2 compared to an activity in a corresponding wild-type cell due to knockout of a gene encoding the polypeptide comprising SEQ ID NO:2 or the polypeptide having at least 96% homology to SEQ ID NO:2 and having essentially the same enzymatic activity as the polypeptide comprising SEQ ID NO:2, and the recombinant cell comprises a polypeptide having at least 90% sequence identity to consecutive 230 amino acids of SEQ ID NO: 15 and having essentially the same enzymatic activity as *Pseudomonas putida* AlkL.

14. The process according to claim 1,
wherein the carboxylic acid ester of the formula (I) is methyl dodecanoate, and
the second carboxylic acid ester comprises methyl 12-amino-dodecanoate.

15. The process according to claim 14, wherein the recombinant cell is *Escherichia coli*, the transaminase is *Chromobacterium violaceum* Cv_2025, and the alanine dehydrogenase is *Bacillus subtilis* ald.

16. The process according to claim 15, further comprising:
after the contacting, extracting the second carboxylic acid ester from the aqueous solution by contacting the aqueous solution with a hydrophobic organic solution comprising a cation exchanger.

17. The process according to claim 16, wherein the recombinant cell comprises a polypeptide having the consecutive 230 amino acids of SEQ ID NO: 15.

18. A method for producing a carboxylic acid ester of the formula (I') from a substrate carboxylic acid ester:

$$R^1\text{-A-COOR}^2 \qquad (I'),$$

where
$R^1$ is hydrogen, —CH$_2$OH, —CHO, —COORS, —CH$_2$SH, —CH$_2$OR$^3$ or —CH$_2$NH$_2$,
$R^2$ is an alkyl group,
$R^3$ is hydrogen or an alkyl group, and
A is an unsubstituted, a linear, or an unsubstituted and linear alkylene radical having at least 10 carbons,
the method comprising:
contacting a recombinant cell with the substrate carboxylic acid ester in an aqueous solution to convert the substrate carboxylic acid ester to the carboxylic acid ester of the formula (I'),
wherein the recombinant cell comprises a knockout of a gene encoding a polypeptide comprising SEQ ID NO: 2 or a polypeptide having at least 70% homology to SEQ ID NO:2 and having essentially the same enzymatic activity as the polypeptide comprising SEQ ID NO:2,
the recombinant cell comprises a polypeptide having at least 80% sequence identity to consecutive 230 amino acids of SEQ ID NO: 15 and having essentially the same enzymatic activity as *Pseudomonas putida* AlkL, where the polypeptide is optionally overexpressed,
the recombinant cell has been transformed to express a transaminase, *Pseudomonas putida* AlkBGT, and an alanine dehydrogenase, the production of the carboxylic acid ester of the formula (I') is increased over a corresponding wild-type cell of the recombinant cell, the recombinant cell has a reduced activity of at least one enzyme catalyzing any of reactions of fatty acid β-oxidation compared to an activity in the wild-type cell due to knockout, and the at least one enzyme catalyzing any of reactions of fatty acid β-oxidation is selected from the group consisting of fatty acid-CoA ligase, acyl-CoA dehydrogenase, 2,4-dienoyl-CoA reductase, enoyl-CoA hydratase, 3-ketoacyl-CoA thiolase, and a fatty acid importer.

19. The method according to claim 18, wherein the recombinant cell comprises a knockout of a gene encoding a polypeptide comprising SEQ ID NO: 2 or a polypeptide having at least 90% homology to SEQ ID NO:2 and having essentially the same enzymatic activity as the polypeptide comprising SEQ ID NO:2, and the recombinant cell comprises a polypeptide having at least 90% sequence identity to consecutive 230 amino acids of SEQ ID NO: 15 and having essentially the same enzymatic activity as *Pseudomonas putida* AlkL.

20. The method according to claim 18, wherein the recombinant cell comprises a knockout of a gene encoding a polypeptide comprising SEQ ID NO: 2 or a polypeptide having at least 96% homology to SEQ ID NO:2 and having essentially the same enzymatic activity as the polypeptide comprising SEQ ID NO:2, and the recombinant cell comprises a polypeptide having at least 90% sequence identity to consecutive 230 amino acids of SEQ ID NO: 15 and having essentially the same enzymatic activity as *Pseudomonas putida* AlkL.

* * * * *

SEQUENCE LISTING

<160> NUMBER OF SEQ ID NOS: 15

<210> SEQ ID NO 1
<211> LENGTH: 771
<212> TYPE: DNA
<213> ORGANISM: Escherichia coli
<220> FEATURE:
<221> NAME/KEY: CDS
<222> LOCATION: (1)..(771)

<400> SEQUENCE: 1

```
atg aat aac atc tgg tgg cag acc aaa ggt cag ggg aat gtt cat ctt      48
Met Asn Asn Ile Trp Trp Gln Thr Lys Gly Gln Gly Asn Val His Leu
1               5                   10                  15 gtg ctg ctg cac gga tgg gga ctg aat gcc gaa gtg tgg cgt tgc att       96
Val Leu Leu His Gly Trp Gly Leu Asn Ala Glu Val Trp Arg Cys Ile
            20                  25                  30 gac gag gaa ctt agc tcg cat ttt acg ctg cac ctt gtt gac ctg ccc      144
Asp Glu Glu Leu Ser Ser His Phe Thr Leu His Leu Val Asp Leu Pro
        35                  40                  45 ggc ttc ggg cgt agc cgg gga ttt ggt gcg ctg tca ctt gct gat atg      192
Gly Phe Gly Arg Ser Arg Gly Phe Gly Ala Leu Ser Leu Ala Asp Met
    50                  55                  60 gcc gaa gcc gtg ctg caa cag gca cct gat aaa gcc att tgg tta ggc      240
Ala Glu Ala Val Leu Gln Gln Ala Pro Asp Lys Ala Ile Trp Leu Gly
65                  70                  75                  80 tgg agt ctg ggc ggg ctg gtg gca agc cag att gcg tta acc cat ccc      288
Trp Ser Leu Gly Gly Leu Val Ala Ser Gln Ile Ala Leu Thr His Pro
                85                  90                  95 gag cgt gtt cag gcg ctg gtc acc gtg gcg tcg tca cct tgt ttt agt      336
Glu Arg Val Gln Ala Leu Val Thr Val Ala Ser Ser Pro Cys Phe Ser
            100                 105                 110
```

| | | | | | | | | | | | | | | | | |
|---|---|---|---|---|---|---|---|---|---|---|---|---|---|---|---|---|
| gct | cgt | gac | gag | tgg | ccg | ggg | ata | aaa | ccg | gac | gtg | ctg | gcg | gga | ttt | 384 |
| Ala | Arg | Asp | Glu | Trp | Pro | Gly | Ile | Lys | Pro | Asp | Val | Leu | Ala | Gly | Phe | |
| | | 115 | | | | | 120 | | | | | 125 | | | | |
| cag | cag | caa | ctc | agt | gat | gat | ttt | cag | cgt | aca | gtg | gag | cgg | ttc | ctg | 432 |
| Gln | Gln | Gln | Leu | Ser | Asp | Asp | Phe | Gln | Arg | Thr | Val | Glu | Arg | Phe | Leu | |
| 130 | | | | | 135 | | | | | 140 | | | | | | |
| gcg | tta | caa | acc | atg | ggg | act | gaa | acg | gcg | cgc | cag | gat | gcg | cgg | gcg | 480 |
| Ala | Leu | Gln | Thr | Met | Gly | Thr | Glu | Thr | Ala | Arg | Gln | Asp | Ala | Arg | Ala | |
| 145 | | | | | 150 | | | | | 155 | | | | | 160 | |
| ttg | aag | aaa | acc | gtt | ctg | gcg | tta | ccg | atg | ccg | gag | gtt | gac | gtg | ctt | 528 |
| Leu | Lys | Lys | Thr | Val | Leu | Ala | Leu | Pro | Met | Pro | Glu | Val | Asp | Val | Leu | |
| | | | | 165 | | | | | 170 | | | | | 175 | | |
| aat | ggc | ggg | ctg | gaa | atc | ctg | aaa | acg | gtc | gat | ctc | cgt | cag | ccg | ctg | 576 |
| Asn | Gly | Gly | Leu | Glu | Ile | Leu | Lys | Thr | Val | Asp | Leu | Arg | Gln | Pro | Leu | |
| | | | 180 | | | | | 185 | | | | | 190 | | | |
| caa | aac | gtg | tcc | atg | ccg | ttt | ttg | cga | ttg | tat | ggc | tat | ctc | gac | ggt | 624 |
| Gln | Asn | Val | Ser | Met | Pro | Phe | Leu | Arg | Leu | Tyr | Gly | Tyr | Leu | Asp | Gly | |
| | | 195 | | | | | 200 | | | | | 205 | | | | |
| ctg | gtg | ccg | cgc | aaa | gtg | gtg | ccg | atg | ctg | gat | aaa | ctt | tgg | cct | cac | 672 |
| Leu | Val | Pro | Arg | Lys | Val | Val | Pro | Met | Leu | Asp | Lys | Leu | Trp | Pro | His | |
| 210 | | | | | 215 | | | | | 220 | | | | | | |
| agc | gaa | tca | tat | atc | ttc | gcc | aaa | gcg | gcc | cat | gcg | cca | ttt | att | tcg | 720 |
| Ser | Glu | Ser | Tyr | Ile | Phe | Ala | Lys | Ala | Ala | His | Ala | Pro | Phe | Ile | Ser | |
| 225 | | | | | 230 | | | | | 235 | | | | | 240 | |
| cat | ccg | gcc | gag | ttt | tgt | cac | ctg | ctg | gtg | gcg | ttg | aag | cag | agg | gtg | 768 |
| His | Pro | Ala | Glu | Phe | Cys | His | Leu | Leu | Val | Ala | Leu | Lys | Gln | Arg | Val | |
| | | | | 245 | | | | | 250 | | | | | 255 | | |
| tag | | | | | | | | | | | | | | | | 771 |

<210> SEQ ID NO 2
<211> LENGTH: 256
<212> TYPE: PRT
<213> ORGANISM: Escherichia coli

<400> SEQUENCE: 2

Met Asn Asn Ile Trp Trp Gln Thr Lys Gly Gln Gly Asn Val His Leu
1               5                   10                  15

Val Leu Leu His Gly Trp Gly Leu Asn Ala Glu Val Trp Arg Cys Ile
                20                  25                  30

Asp Glu Glu Leu Ser Ser His Phe Thr Leu His Leu Val Asp Leu Pro
            35                  40                  45

Gly Phe Gly Arg Ser Arg Gly Phe Gly Ala Leu Ser Leu Ala Asp Met
        50                  55                  60

Ala Glu Ala Val Leu Gln Gln Ala Pro Asp Lys Ala Ile Trp Leu Gly
65                  70                  75                  80

Trp Ser Leu Gly Gly Leu Val Ala Ser Gln Ile Ala Leu Thr His Pro
                85                  90                  95

Glu Arg Val Gln Ala Leu Val Thr Val Ala Ser Ser Pro Cys Phe Ser
                100                 105                 110

Ala Arg Asp Glu Trp Pro Gly Ile Lys Pro Asp Val Leu Ala Gly Phe
            115                 120                 125

Gln Gln Gln Leu Ser Asp Asp Phe Gln Arg Thr Val Glu Arg Phe Leu
        130                 135                 140

Ala Leu Gln Thr Met Gly Thr Glu Thr Ala Arg Gln Asp Ala Arg Ala
145                 150                 155                 160

Leu Lys Lys Thr Val Leu Ala Leu Pro Met Pro Glu Val Asp Val Leu
                165                 170                 175

```
Asn Gly Gly Leu Glu Ile Leu Lys Thr Val Asp Leu Arg Gln Pro Leu
            180                 185                 190

Gln Asn Val Ser Met Pro Phe Leu Arg Leu Tyr Gly Tyr Leu Asp Gly
            195                 200                 205

Leu Val Pro Arg Lys Val Val Pro Met Leu Asp Lys Leu Trp Pro His
    210                 215                 220

Ser Glu Ser Tyr Ile Phe Ala Lys Ala Ala His Ala Pro Phe Ile Ser
225                 230                 235                 240

His Pro Ala Glu Phe Cys His Leu Leu Val Ala Leu Lys Gln Arg Val
                245                 250                 255

<210> SEQ ID NO 3
<211> LENGTH: 500
<212> TYPE: DNA
<213> ORGANISM: Escherichia coli

<400> SEQUENCE: 3
cggcttcgct atcccattgg cagtgcaacc agcgtgataa cggctgacac agcaaatcgc      60
tctgattaaa tccccgacgc cagtgacgcc gctgccataa cggaacgctg acgatgcgat     120
ccggcaattg caacccggtg gtgcgacgag cgtgtaagac ttccaatagt aacagacgtg     180
acagggcgct ggcgatttca ctgcgccggg aaaatttaag ctggtggata gcggactta     240 acggcggcgc atagtcggca accgtgacca gtctttgcca gggcggcggt ttttgcaggc     300
agcgaccgca gggaagatgg gagtgtgtgg cgggtaatcc acattgtggg cataacgttt     360
tatctgtgcg ggtggcgcgt gaacagaccg aacaaatccc ccaatgacct aacgccagtg     420
gcattcggca tagccagcat aatcccggta ctgttagcat atgttcatcc ttgtaagtca     480
aaagagaaca atagcggatg                                                500

<210> SEQ ID NO 4
<211> LENGTH: 500
<212> TYPE: DNA
<213> ORGANISM: Escherichia coli

<400> SEQUENCE: 4
gcgttgaagc agagggtgta ggtggctttt gaaatggcga gacagaactt tactgactcg      60
ccgcagccaa ctcttcttct gacagcccgg taaagcgcat gatgtctgca agaggaactc     120
cggattcaag cattattttg gctatatgca gggctttgga ttgttccccc tcctgccgca     180
atctttccgc aatagtcatt aaactctcct tgtgtttcgg tgaacgttcg gcaacgccgt     240
cgataaaatc gttaaaacgt acagcgtcgc cagtttgcag tatgtaatta acagcccctt     300
tgatttgtct gtcattagcg tatccactac ttaataagca ggccatttgc tctaccagcc     360
ccatcaggtc gcgttgacga atatgttttt gaattaactc cagcagcgcc atacgtcggt     420
gctgcatgat ttcatcatca ggcatgacgg tgacatcaat cagcggaaat gcggaggcat     480
aaagctgcct tgccagtttg                                                500

<210> SEQ ID NO 5
<211> LENGTH: 6654
<212> TYPE: DNA
<213> ORGANISM: Artificial Sequence
<220> FEATURE:
<223> OTHER INFORMATION: vector

<400> SEQUENCE: 5
gagtcgaccg gtggcgaatg ggacgcgccc tgtagcggcg cattaagcgc ggcgggtgtg      60
```

-continued

```
gtggttacgc gcagcgtgac cgctacactt gccagcgccc tagcgcccgc tcctttcgct    120
ttcttccctt cctttctcgc cacgttcgcc ggctttcccc gtcaagctct aaatcggggg    180
ctcccttag ggttccgatt tagtgcttta cggcacctcg accccaaaaa acttgattag    240
ggtgatggtt cacgtagtgg gccatcgccc tgatagacgg ttttttcgccc tttgacgttg    300
gagtccacgt tctttaatag tggactcttg ttccaaactg gaacaacact caaccctatc    360
tcggtctatt cttttgattt ataagggatt ttgccgattt cggcctattg gttaaaaaat    420
gagctgattt aacaaaaatt taacgcgaat tttaacaaaa tattaacgct tacaatttag    480
gtggcactt tcggggaaat gtgcgcggaa cccctatttg tttatttttc taaatacatt    540
caaatatgta tccgctcacc gcgatccttt ttaacccatc acatatacct gccgttcact    600
attatttagt gaaatgagat attatgatat tttctgaatt gtgattaaaa aggcaacttt    660
atgcccatgc aacagaaact ataaaaaata cagagaatga aaagaaacag atagattttt    720
tagttcttta ggcccgtagt ctgcaaatcc ttttatgatt ttctatcaaa caaaagagga    780
aaatagacca gttgcaatcc aaacgagagt ctaatagaat gaggtcgaaa agtaaatcgc    840
gcgggtttgt tactgataaa gcaggcaaga cctaaaatgt gtaaagggca aagtgtatac    900
tttggcgtca ccccttacat attttaggtc ttttttttatt gtgcgtaact aacttgccat    960
cttcaaacag gagggctgga agaagcagac cgctaacaca gtacataaaa aaggagacat   1020
gaacgatgaa catcaaaaag tttgcaaaac aagcaacagt attaaccttt actaccgcac   1080
tgctggcagg aggcgcaact caagcgtttg cgaagaaac gaaccaaaag ccatataagg   1140
aaacatacgg catttcccat attacacgcc atgatatgct gcaaatccct gaacagcaaa   1200
aaaatgaaaa atatcaagtt cctgagttcg attcgtccac aattaaaaat atctcttctg   1260
caaaaggcct ggacgtttgg gacagctggc cattacaaaa cgctgacggc actgtcgcaa   1320
actatcacgg ctaccacatc gtcttgcat tagccggaga tcctaaaaat gcggatgaca   1380
catcgattta catgttctat caaaaagtcg gcgaaacttc tattgacagc tggaaaaacg   1440
ctggccgcgt cttaaagac agcgacaaat tcgatgcaaa tgattctatc ctaaaagacc   1500
aaacacaaga atggtcaggt tcagccacat ttacatctga cggaaaaatc cgtttattct   1560
acactgattt ctccggtaaa cattacggca aacaaacact gacaactgca caagttaacg   1620
tatcagcatc agacagctct ttgaacatca acggtgtaga ggattataaa tcaatctttg   1680
acggtgacgg aaaaacgtat caaaatgtac agcagttcat cgatgaaggc aactacagct   1740
caggcgacaa ccatacgctg agagatcctc actacgtaga agataaaggc cacaaatact   1800
tagtatttga agcaaacact ggaactgaag atggctacca aggcgaagaa tctttattta   1860
acaaagcata ctatgcaaa agcacatcat tcttccgtca agaaagtcaa aaacttctgc   1920
aaagcgataa aaaacgcacg gctgagttag caaacggcgc tctcggtatg attgagctaa   1980
acgatgatta cacactgaaa aaagtgatga accgctgat tgcatctaac acagtaacag   2040
atgaaattga acgcgcgaac gtctttaaaa tgaacggcaa atggtacctg ttcactgact   2100
cccgcggatc aaaaatgacg attgacggca ttacgtctaa cgatatttac atgcttggtt   2160
atgtttctaa ttcttaaact ggcccataca agccgctgaa caaaactggc cttgtgttaa   2220
aaatggatct tgatcctaac gatgtaacct ttacttactc acacttcgct gtacctcaag   2280
cgaaaggaaa caatgtcgtg attacaagct atatgacaaa cagaggattc tacgcagaca   2340
aacaatcaac gtttgcgcca agcttcctgc tgaacatcaa aggcaagaaa acatctgttg   2400
tcaaagacag catccttgaa caaggacaat taacagttaa caaataaaaaa cgcaaagaa   2460
```

```
aatgccgata ttgactaccg gaagcagtgt gaccgtgtgc ttctcaaatg cctgattcag    2520
gctgtctatg tgtgactgtt gagctgtaac aagttgtctc aggtgttcaa tttcatgttc    2580
tagttgcttt gttttactgg ttttcacctgt tctattaggt gttacatgct gttcatctgt    2640
tacattgtcg atctgttcat ggtgaacagc tttaaatgca ccaaaaactc gtaaaagctc    2700
tgatgtatct atcttttta caccgttttc atctgtgcat atggacagtt ttcccttga     2760 tatgtaacgg tgaacagttg ttctactttt gtttgttagt cttgatgctt cactgataga    2820
tacaagagcc ataagaacct cagatccttc cgtatttagc cagtatgttc tctagtgtgg    2880
ttcgttgttt ttgcgtgagc catgagaacg aaccattgag atcatactta ctttgcatgt    2940
cactcaaaaa ttttgcctca aaactggtga gctgaatttt tgcagttaaa gcatcgtgta    3000 gtgttttct tagtccgtta tgtaggtagg aatctgatgt aatggttgtt ggtattttgt     3060
caccattcat ttttatctgg ttgttctcaa gttcggttac gagatccatt tgtctatcta    3120
gttcaacttg gaaaatcaac gtatcagtcg ggcggcctcg cttatcaacc accaatttca    3180
tattgctgta agtgtttaaa tctttactta ttggtttcaa aacccattgg ttaagccttt    3240
taaactcatg gtagttattt tcaagcatta acatgaactt aaattcatca aggctaatct    3300
ctatatttgc cttgtgagtt ttcttttgtg ttagttcttt taataaccac tcataaatcc    3360
tcatagagta tttgttttca aaagacttaa catgttccag attatatttt atgaattttt    3420
ttaactggaa aagataaggc aatatctctt cactaaaaac taattctaat ttttcgcttg    3480
agaacttggc atagtttgtc cactggaaaa tctcaaagcc tttaaccaaa ggattcctga    3540
tttccacagt tctcgtcatc agctctctgg ttgctttagc taatacacca taagcatttt    3600
ccctactgat gttcatcatc tgaacgtatt ggttataagt gaacgatacc gtccgttctt    3660
tccttgtagg gttttcaatc gtgggttga gtagtgccac acagcataaa attagcttgg     3720
tttcatgctc cgttaagtca tagcgactaa tcgctagttc atttgctttg aaaacaacta    3780
attcagacat acatctcaat tggtctaggt gattttaatc actataccaa ttgagatggg    3840
ctagtcaatg ataattacta gtccttttcc tttgagttgt gggtatctgt aaattctgct    3900
agacctttgc tggaaaactt gtaaattctg ctagaccctc tgtaaattcc gctagacctt    3960
tgtgtgtttt ttttgtttat attcaagtgg ttataattta tagaataaag aaagaataaa    4020 aaagataaa aagaatagat cccagccctg tgtataactc actactttag tcagttccgc     4080
agtattacaa aaggatgtcg caaacgctgt ttgctcctct acaaaacaga ccttaaaacc    4140
ctaaaggctt aagtagcacc ctcgcaagct cgggcaaatc gctgaatatt cctttgtct    4200 ccgaccatca ggcacctgag tcgctgtctt tttcgtgaca ttcagttcgc tgcgctcacg    4260
gctctggcag tgaatggggg taaatggcac tacaggcgcc ttttatggat tcatgcaagg    4320
aaactaccca taatacaaga aaagcccgtc acgggcttct cagggcgttt tatggcgggt    4380
ctgctatgtg gtgctatctg acttttgct gttcagcagt tcctgccctc tgattttcca    4440
gtctgaccac ttcggattat cccgtgacag gtcattcaga ctggctaatg cacccagtaa    4500
ggcagcggta tcatcaacag gcttacccgt cttactgtcg gggatcgacg ctctcccta    4560 tgcgactcct gcacctttcg tcttcgaata aatacctgtg acggaagatc acttcgcaga    4620
ataaataaat cctggtgtcc ctgttgatac cgggaagccc tgggccaact tttggcgaaa    4680
atgagacgtt gatcggcacg taagaggttc aactttcac cataatgaaa taagatcact     4740
accgggcgta ttttttgagt tatcgagatt ttcaggagct aaggaagcta aaatggagaa    4800
```

```
aaaaatcact ggatatacca ccgttgatat atcccaatgg catcgtaaag aacatttga      4860
ggcatttcag tcagttgctc aatgtaccta taaccagacc gttcagctgg atattacggc    4920
cttttaaag accgtaaaga aaaataagca caagttttat ccggccttta ttcacattct    4980
tgcccgcctg atgaatgctc atccggaatt ccgtatggca atgaaagacg gtgagctggt    5040
gatatgggat agtgttcacc cttgttacac cgttttccat gagcaaactg aaacgttttc    5100
atcgctctgg agtgaatacc acgacgattt ccggcagttt ctacacatat attcgcaaga    5160
tgtggcgtgt tacggtgaaa acctggccta tttccctaaa gggtttattg agaatatgtt    5220
tttcgtctca gccaatccct gggtgagttt caccagtttt gatttaaacg tggccaatat    5280
ggacaacttc ttcgcccccg ttttcaccat gggcaaatat tatacgcaag cgacaaggt    5340
gctgatgccg ctggcgattc aggttcatca tgccgtttgt gatggcttcc atgtcggcag    5400
aatgcttaat gaattacaac agtactgcga tgagtggcag ggcggggcgt aattttttta    5460
aggcagttat tggtgccctt aaacgcctgg ttgctacgcc tgaataagtg ataataagcg    5520
gatgaatggc agaaattcga agcaaattc gacccggtcg tcggttcagg gcagggtcgt    5580
taaatagccg cttatgtcta ttgctggtct cggtacccgg ggatcgcggc ccggcttcgc    5640
tatcccattg gcagtgcaac cagcgtgata acggctgaca cagcaaatcg ctctgattaa    5700
atccccgacg ccagtgacgc cgctgccata acggaacgct gacgatgcga tccggcaatt    5760
gcaacccggt ggtgcgacga gcgtgtaaga cttccaatag taacagacgt gacagggcgc    5820
tggcgatttc actgcgccgg gaaaatttaa gctggtggat aagcggactt aacggcggcg    5880
catagtcgga aaccgtgacc agtctttgcc agggcggcgg ttttttgcagg cagcgaccgc    5940
agggaagatg ggagtgtgtg gcgggtaatc cacattgtgg gcataacgtt ttatctgtgc    6000
gggtggcgcg tgaacagacc gaacaaatcc cccaatgacc taacgccagt ggcattcggc    6060
atagccagca taatcccggt actgttagca tatgttcatc cttgtaagtc aaaagagaac    6120
aatagcggat gcctcgaggg cgttgaagca gagggtgtag gtggcttttg aaatggcgag    6180
acagaacttt actgactcgc cgcagccaac tcttcttctg acagcccggt aaagcgcatg    6240
atgtctgcaa gaggaactcc ggattcaagc attattttgg ctatatgcag ggctttggat    6300
tgttcccct cctgccgcaa tctttccgca atagtcatta aactctcctt gtgtttcggt    6360
gaacgttcgg caacgccgtc gataaaatcg ttaaaacgta cagcgtcgcc agtttgcagt    6420
atgtaattaa acagcccttt gatttgtctg tcattagcgt atccactact taataagcag    6480
gccatttgct ctaccagccc catcaggtcg cgttgacgaa tatgttttg aattaactcc    6540
agcagcgcca tacgtcggtg ctgcatgatt tcatcatcag gcatgacggt gacatcaatc    6600
agcggaaatg cggaggcata aagctgcctt gccagtttgg gccgcgatcc tcta           6654
```

<210> SEQ ID NO 6
<211> LENGTH: 39
<212> TYPE: DNA
<213> ORGANISM: Artificial Sequence
<220> FEATURE:
<223> OTHER INFORMATION: primer

<400> SEQUENCE: 6
ccggggatcg cggcccggct tcgctatccc attggcagt                             39

<210> SEQ ID NO 7
<211> LENGTH: 58
<212> TYPE: DNA
<213> ORGANISM: Artificial Sequence
<210> SEQ ID NO 7
<211> LENGTH: 58
<212> TYPE: DNA
<213> ORGANISM: Artificial Sequence
<220> FEATURE:
<223> OTHER INFORMATION: primer

<400> SEQUENCE: 7
cctctgcttc aacgccctcg aggcatccgc tattgttctc ttttgactta caaggatg      58

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
gcgttgaagc agagggtgta ggtg                                            24

<210> SEQ ID NO 9
<211> LENGTH: 39
<212> TYPE: DNA
<213> ORGANISM: Artificial Sequence
<220> FEATURE:
<223> OTHER INFORMATION: primer

<400> SEQUENCE: 9
tagaggatcg cggcccaaac tggcaaggca gctttatgc                            39

<210> SEQ ID NO 10
<211> LENGTH: 1008
<212> TYPE: DNA
<213> ORGANISM: Artificial Sequence
<220> FEATURE:
<223> OTHER INFORMATION: resulting k/o gene

<400> SEQUENCE: 10
cggcttcgct atcccattgg cagtgcaacc agcgtgataa cggctgacac agcaaatcgc      60
tctgattaaa tccccgacgc cagtgacgcc gctgccataa cggaacgctg acgatgcgat     120
ccggcaattg caacccggtg gtgcgacgag cgtgtaagac ttccaatagt aacagacgtg     180
acagggcgct ggcgatttca ctgcgccggg aaaatttaag ctggtggata agcggactta     240
acggcggcgc atagtcggca accgtgacca gtctttgcca gggcggcggt ttttgcaggc     300
agcgaccgca gggaagatgg gagtgtgtgg cgggtaatcc acattgtggg cataacgttt     360
tatctgtgcg ggtggcgcgt gaacagaccg aacaaatccc caatgacct aacgccagtg      420 gcattcggca tagccagcat aatcccggta ctgttagcat atgttcatcc ttgtaagtca     480
aaagagaaca atagcggatg cctcgagggc gttgaagcag agggtgtagg tggcttttga     540
aatggcgaga cagaacttta ctgactcgcc gcagccaact cttcttctga cagcccggta     600
aagcgcatga tgtctgcaag aggaactccg gattcaagca ttattttggc tatatgcagg     660
gctttggatt gttcccccctc ctgccgcaat cttttccgcaa tagtcattaa actctccttg     720
tgtttcggtg aacgttcggc aacgccgtcg ataaaatcgt taaaacgtac agcgtcgcca     780
gtttgcagta tgtaattaaa cagccctttg atttgtctgt cattagcgta tccactactt     840
aataagcagg ccatttgctc taccagcccc atcaggtcgc gttgacgaat atgttttga      900 attaactcca gcagcgccat acgtcggtgc tgcatgattt catcatcagg catgacggtg     960
acatcaatca gcggaaatgc ggaggcataa agctgccttg ccagtttg                 1008

<210> SEQ ID NO 11
<211> LENGTH: 12348
<212> TYPE: DNA

<213> ORGANISM: Artificial Sequence
<220> FEATURE:
<223> OTHER INFORMATION: vector

<400> SEQUENCE: 11

```
gggaagccct gcaaagtaaa ctggatggct ttcttgccgc caaggatctg atggcgcagg      60
ggatcaagat ctgatcaaga gacaggatga ggatcgtttc gcatgattga acaagatgga     120
ttgcacgcag gttctccggc cgcttgggtg gagaggctat tcggctatga ctgggcacaa     180
cagacaatcg gctgctctga tgccgccgtg ttccggctgt cagcgcaggg gcgcccggtt     240
cttttttgtca agaccgacct gtccggtgcc ctgaatgaac tgcaggacga ggcagcgcgg    300
ctatcgtggc tggccacgac gggcgttcct tgcgcagctg tgctcgacgt tgtcactgaa     360
gcgggaaggg actggctgct attgggcgaa gtgccgggc aggatctcct gtcatctcac      420
cttgctcctg ccgagaaagt atccatcatg gctgatgcaa tgcggcggct gcatacgctt     480
gatccggcta cctgcccatt cgaccaccaa gcgaaacatc gcatcgagcg agcacgtact     540
cggatgaag ccggtcttgt cgatcaggat gatctggacg aagagcatca ggggctcgcg      600
ccagccgaac tgttcgccag gctcaaggcg cgcatgcccg acggcgagga tctcgtcgtg     660
acccatggcg atgcctgctt gccgaatatc atggtgaaa atggccgctt tctggattc       720
atcgactgtg gccggctggg tgtggcggac cgctatcagg acatagcgtt ggctacccgt     780
gatattgctg aagagcttgg cggcgaatgg gctgaccgct tcctcgtgct ttacggtatc     840
gccgctcccg attcgcagcg catcgccttc tatcgccttc ttgacgagtt cttctgagcg     900
ggactctggg gttcgaaatg accgaccaat cgattggtaa ctgtcagacc aagtttactc     960
atatatactt tagattgatt taaaacttca ttttaattt aaaaggatct aggtgaagat     1020
ccttttttgat aatctcatga ccaaaatccc ttaacgtgag ttttcgttcc actgagcgtc    1080
agaccccgta gaaaagatca aaggatcttc ttgagatcct tttttctgc gcgtaatctg     1140
ctgcttgcaa acaaaaaaac caccgctacc agcggtggtt tgtttgccgg atcaagagct    1200
accaactctt tttccgaagg taactggctt cagcagagcg cagataccaa atactgtcct    1260
tctagtgtag ccgtagttag gccaccactt caagaactct gtagcaccgc ctacatacct    1320
cgctctgcta atcctgttac cagtggctgc tgccagtggc gataagtcgt gtcttaccgg    1380
gttggactca agacgatagt taccggataa ggcgcagcgg tcgggctgaa cgggggttc     1440
gtgcacacag cccagcttgg agcgaacgat ctacaccgaa ctgagatacc tacagcgtga    1500
gctatgagaa agcgccacgc ttcccgaagg gagaaaggcg acaggtatc cggtaagcgg      1560
cagagtcgga acaggagagc gcacgaggga gcttccaggg ggaaacgcct ggtatcttta    1620
tagtcctgtc gggtttcgcc acctctgact tgagcgtcga ttttgtgat gctcgtcagg     1680
ggggcggagc ctatggaaaa acgccagcaa cgcggccttt ttacggttcc tggccttttg    1740
ctggcctttt gctcacatgt tctttcctgc gttatcccct gattctgtgg ataaccgtat    1800
taccgccttt gagtgagctg ataccgctcg ccgcagccga cgaccgagc gcagcgagtc     1860
agtgagcgag gaagcggaag agcgcctgat gcggtatttt ctccttacgc atctgtgcgg    1920
tatttcacac cgcataggg atctccaatc gtgccttggc gcagcgacag ccctcggtcc     1980
cccagatagc cattgatctt ctctcgcctg tcccctcagt tcagtaattt cctgcatttg    2040
cctgtttcca gtcggtagat attccacaaa acagcaggga agcagcgctt ttccgctgca    2100
taaccctgct tcgggtcat tatagcgatt ttttcggtat atccatcctt tttcgcacga    2160
tatacaggat tttgccaaag ggttcgtgta gactttcctt ggtgtatcca acggcgtcag    2220
```

```
ccgggcagga taggtgaagt aggcccaccc gcgagcgggt gttccttctt cactgtccct    2280
tattcgcacc tggcggtgct caacgggaat cctgctctgc gaggctggcc ggctaccgcc    2340
ggcgtaacag atgagggcaa gcggatggct gatgaaacca agccaaccag gaagggcagc    2400
ccacctatca aggtgtactg ccttccagac gaacgaagag cgattgagga aaaggcggcg    2460
gcggccggca tgagcctgtc ggcctacctg ctggccgtcg gccagggcta caaaatcacg    2520
ggcgtcgtgg actatgagct cgagaacgct taccgccaac acagcagtgt atttgaataa    2580
gagctcgaac atgatcggat ctcccatttc agcaagggaa atcccaccat agccaccacc    2640
gatttatgtg gcgtagaaaa cggtcatcac caaatatggc aatacttccc cgcccaagcg    2700
ccacataaca gcctgggcca cattttacgc ggtagttccg cacgtacgga gtgcgggggg    2760
cggcaggtaa ctgccgtccc tatcgcgacc gttggttcga gtggctgagc atcattgcta    2820
atcaggtaat tttatactcc ctgcaagcgc accttgacgt ttaggcaaat ttattgtctc    2880
agttgcaatc agtcgctcct gcttgtacgc aaggacttct agttcaagag tttcgttatt    2940
aattgcaaca acgagtttat cgtagtcctt tagagcacca agtccttgca gcgccatccc    3000
tttaagatca gaccagaacc gtggtggggt tggtgctggt gttgatgtgc cacagatgct    3060
acttgcgaca atttgagcgt gtgtaaccgc attatgaatt gtctctaaac gtaccatcgt    3120
tccccaaaaa ggatttctag ccattgcgca gtcgccgatt gcatatatac ttgtatccga    3180
tgtacacatc tgatcatcga ccacaacacc attactcact tcaagggccg cctcagttgc    3240
cagctctagc tctgggatag caccgattcc aactacaatc agatccgcct gaatttcttc    3300
tccactttca agtacgcatt gttcaacatg gccattcctg ccctttatag acgttaattt    3360
cgcattcagc ttgaactcaa ttccttcagc ctccaggcgg gctctgacta agtttgctgc    3420
tgccggcgta accacgcgcg ccattacacg cggggcggct tctatcactg tgaccctctt    3480
ccctaagccc accgcagctg aggcgacttc aagcccgatt actccgccgc caacacaaac    3540
aacagacgca ctctccacaa gtttcctacg taaattttg gcgtcttcca tactgcgtaa    3600
atagcagacc ccagacagtt cagacccctc gcaggttaac ctacgtgcgc tagcacctgt    3660
tgcaagaatc aattttcat acgcgtattc ttttccatct ttagaagaaa ctatcttacg    3720
ccccacgtcg attgatacaa tcggtgtatt taacgaaatg gtaatattgt tattcgtata    3780
aaaaccttct ggctttaatg gcactgcgga ttctgcaatc tcacttgtca gaaaagcctt    3840
ggatagagga ggccgctgat aaggcgccac agactccctg ctaaaaatcc taatttcccc    3900
tttataacca tattgacgaa gccagaacgc agcatttact ccagctgtac cagcgccaac    3960
aacaacgatt gccataattc tctctccggt atacttttca ctatatcact taatgccgat    4020 tatttttagat aattccttga cgctcagctt caattgttgc ttgcgtgcga ttcactacat    4080
tcaaggtggc aaatattttc ctcatatgcc actttatagc atcttcggtg acatgcatat    4140
ttgttgctat ttgtttgttt gagcacccct cttttacaag cctcaagaca gcaatctgct    4200
tccgtgtcaa taaagcgtca gctttattct ctgcggactt tccaatctca actattcgcg    4260
gaagactaaa agccccaatc gcttgatcta aattaactgc tgtgaaggct tcacatgaag    4320
ccggtattat tcgctcaatt aaacatactt catcaagaac tgtttgaaag cattgaagct    4380
gttttgctat ctccactgca taaacaatgt taagctgagc cttttttaaa tcaccggcac    4440
ctgcctgcgc tccggccaaa cacaataatc cacggacttc cagctggccc gcgttaattt    4500
tacgggcttg ctgaatagcc aataacgctc tgtgcgcggc actatgaaag ttccgatctc    4560
```

```
gggaaagcac tagtgattga acaagcagca ggcgtgcttt tagggggggct gagtgctgtc    4620
cggagaaaat cttatgatct tcaagagttt ttaaattatt tatgcccgtt atgccttgac    4680
agactaagcg ctgatagatc tcaatttggc tcataacttc caatcttggt agattttttt    4740
caaccgcatg cgccttcgcc cactccaata tctcaatgga gccatttagg tcactccttc    4800
caagccgcca agctgacaca gcacggcata cggaaaaaaa cacgtctgtc accccgtgat    4860
tggaaatgaa ctctaaaatt ttggagagct tttcttctga ggtgtccaag cagcgcaatt    4920
cataatgtaa ctcaagctct agagcgtcaa acattttcga agtaaactcg gattccatca    4980
tctgcgcgcg actgtctgtg cgtgcttgag ttataatctg cctcgcccag cccattttc    5040
cgcttgctag ggcttgttga aacctcgcga catacagcca accaaaagca aaattttgtt    5100
ttgcaaattt attcacggct tgggcctgag ccagcacctt ctccaactct gcaaatctat    5160
actcactggc aaaaataaaa gccaaacagg ttagcgcggc ccctttttcca actgcgtttg    5220
aatccccaaa taaactaatc cacttattac agagctcctc actcgaaagc atttcatctt    5280
tcgttgcttt acctattgca agcacaagct gcagccattc cttttcttgc catttatttt    5340
ttttatcgga ttgtgaagat aggtctttaa ttaacttctc tgctcgcgcg ccttgctgac    5400
tgaaatacaa tacccacgcg taactaataa gcactatggg ttttttgtgc caggcctgct    5460
tcggcagctc taacagccac tgtctcagcg catctatttc gccctgacga aatgacaaat    5520
ctaaaattat tctctcagac atgctgactg cccagcgaca gtcattcgcc cgtagggata    5580
ttcgtattgc atactggtat tcacctctac gccaatgcca gaaagctgca cgcttaagca    5640
ggtaggatct tttagcagga ttttcagtcc aagtaatttc tcgtagaaaa ttacgcagta    5700
ctggatgcag tgtaaactgc gctggctcac cgctcacatg gcgaagcaac atgtaattag    5760
tgcttaaata cttaatacat gagacccat tgacgcattt gaatacataa ttgtattgat    5820
caggcgtcac gaaatcgagc aatgaagaat ttgcaagaaa acacgatag cgctcgggaa    5880
tcgcctcaaa tatttcatcc ctaaagtaat tgtctacttc aactactgct gaaatatgct    5940
tggccggcaa ctcacgcttt aacaaaaaaa ctacaagagc aggccacccc tcaacttctt    6000
gcaccaaggt ctctatctgt tcttcaggaa ctccaagaac agactctgcc tccgctaacg    6060
ccaccgcctc ttctgcgcta aaggccaagt cttttctcggt gtactcccgc atagcgcctg    6120
caagtttaag ctgcgagaac ccttttattg tattgcctgc aactgcaaac ctgatatttt    6180
ttggtgtatt taacataaac tccataagtg cgtgcaacaa cggcaagtct aagtcatgat    6240
taatattatc caaacaaact agcgtttcta tctcgttatt cgaggtgctc tgccaaagac    6300
tagatgcaag gtctcgcaag agcgcaggct tgctcacacc ctctctcaca cggctgaatt    6360
ttaccatttc gaaagtttca agctgctcaa taatctctgc gcagatatca aattcactgt    6420
aagaactggc tcttaaagaa agccacactg caggacgtcc ggctgttctg tggcgtagcc    6480
actcgaacgc aagagcaacg gttttcccat atccaggtgg ggctctgtaa aggcatactc    6540
tgggagcggc tccatccgcg atactcaatc ttggccgata tatgcaacta tgaactttgg    6600
cacttactag agtcgtaatt tgatccgctc cgaccttagc gaccgggaaa tcattattta    6660
ttattatttt cattatgcta ttctcgcgcc agctgactgg aaattttcac cataggttac    6720
ggtgttaaat attaaaacta cacttaagtg tagtcggcat gatcggtggt gcaaaatatt    6780
tactagggaa ggtctgaagt aggccgctat ttctggccga cttcggcctt cgccgatttt    6840
gaagacgggg accgggtcaa aatcgaccag atagctcgct catttcggtg ctttcagccg    6900
tcgcgagtag ctcgcggtac ctggcatgct tgcggccagc tcgtgttttt ccagcagacg    6960
```

```
acggagcaaa aactacccgt aggtgtagtt ggcgcaagcg tccgattagc tcaggtttaa    7020
gatgtcgaga gtgagagtgg gcggcttaac tttctcagtt aggcataaaa ttacgtctta    7080
aatctcgtag cgactaattt aataaaaatt ggagaattcc atatgcttga gaaacacaga    7140
gttctggatt ccgctccaga gtacgtagat aaaaagaaat atctctggat actatcaact    7200
ttgtggccgg ctactccgat gatcggaatc tggcttgcaa atgaaactgg ttgggggatt    7260
ttttatgggc tggtattgct cgtatggtac ggcgcacttc cattgcttga tgcgatgttt    7320
ggtgaggact taataatcc gcctgaagaa gtggtgccga actagagaa ggagcggtac      7380 tatcgagttt tgacatatct aacagttcct atgcattacg ctgcattaat tgtgtcagca    7440
tggtgggtcg gaactcagcc aatgtcttgg cttgaaattg gtgcgcttgc cttgtcactg    7500
ggtatcgtga acggactagc gctcaataca ggacacgaac tcggtcacaa gaaggagact    7560
tttgatcgtt ggatggccaa aattgtgttg ctgtcgtag ggtacggtca cttctttatt     7620
gagcataata agggtcatca ccgtgatgtc gctacaccga tggatcctgc aacatcccgg    7680
atgggagaaa gcatttataa gttttcaatc cgtgagatcc caggagcatt tattcgtgct    7740
tgggggcttg aggaacaacg ccttcgcgc cgtggccaaa gcgtttggag tttcgataat     7800
gaaatcctcc aaccaatgat catcacagtt attctttacg ccgttctcct tgccttgttt    7860
ggacctaaga tgctggtgtt cctgccgatt caaatggctt tcggttggtg gcagctgacc    7920
agtgcgaact atattgaaca ttacggcttg ctccgtcaaa aaatggagga cggtcgatat    7980
gagcatcaaa agccgcacca ttcttggaat agtaatcaca tcgtctctaa tctagtgctg    8040
ttccaccttc agcggcactc ggatcaccac gcgcatccaa cacgttctta tcagtcactt    8100
cgggattttc ccggcctgcc ggctcttccg acgggttacc ctggtgcatt tttgatggcg    8160
atgattcctc agtggtttag atcagttatg gatcccaagg tagtagattg ggctggtggt    8220
gaccttaata agatccaaat tgatgattcg atgcgagaaa cctatttgaa aaaatttggc    8280
actagtagtg ctggtcatag ttcgagtacc tctgcggtag catcgtagtt atgtgagcac    8340
gcagagcccg gcggtcgata tttacaataa gtgcttcaat tttatgtgcg gcgttgaaag    8400
ctctcacaaa gagtgcactt cgctaaagtg ctgagggttg attgcctctc tgtaattgct    8460
ttgaaggcga cctgctccga tagttacact ctgatgaagt tgtcggagca gcgactaacg    8520
ctgagttaat aggagagtgg gagaatgtca aggtaccagt gtccagattg tcagtatatc    8580
tatgatgaaa ataagggga gccgcacgaa ggtttccacc cgaacaccag ctggaatgat     8640
atccccaaag attgggcatg cccggactgc gcagttcgag acaaggtgga ctttatcttt    8700
ctcgcggatt ctccctcgaa agaaacacag ctaggggtga atagtcagct tgccaactcg    8760
gaaagtggta tttcagatgc tactccaact ggaatggcga ttttggccgc agaattagtg    8820
atcccactta atcaagaaaa taaaaatgag ggctgtgcgg ctaagactga agttcttgat    8880
caggcgagca cccacaggt tgtaagaaaa tcttccacaa ggaagaagat gagaaataaa     8940
taacgcaaat ttgccgcaac gcaaaataac aatttgacat ggtgatgagt atggctagct    9000
ataaatgccc ggattgtaat tatgtttatg atgagagtgc gggtaatgtg catgagggt     9060 tttctccagg tacgccttgg caccttattc ctgaggattg gtgctgcccc gattgcgccg    9120
ttcgagacaa gcttgacttc atgttaattg agagcggcgt aggtgaaaag ggcgtcacct    9180
caacccatac ttcgccaaat ttatccgagg ttagtgcac aagtttaact gctgaagcag     9240
tggttgcgcc gacaagctta gagaaattgc ctagtgccga cgttaaaggc caagatctat    9300
```

```
ataaaactca acctccaagg tctgatgccc aaggcgggaa agcatacttg aagtggatat    9360
gtattacttg tggccatata tatgatgagg cgttgggcga tgaggccgag ggttttactc    9420
caggtactcg ctttgaggat attcctgatg actggtgctg tccggattgc ggggctacga    9480
aagaagacta tgtgctctac gaggaaaagt gaagattaaa acttcaagtc attctaggta    9540
attcaggaca aaataaaaat gaccatacca attagcctag ccaagttaaa ctctagtgcc    9600
gatacccatt cagcgcttgt cgacctgtaa cgacaacaaa acgagggtag cacaatgagt    9660
ttttctaatt ataaagtaat cgcgatgccg gtgttggttg ctaattttgt tttgggggcg    9720
gccactgcat gggcgaatga aaattatccg gcgaaatctg ctggctataa tcagggtgac    9780
tgggtcgcta gcttcaattt ttctaaggtc tatgtgggtg aggagcttgg cgatctaaat    9840
gttggagggg gggctttgcc aaatgctgat gtaagtattg gtaatgatac aacacttacg    9900
tttgatatcg cctattttgt tagctcaaat atagcggtgg atttttttgt tggggtgcca    9960
gctagggcta aatttcaagg tgagaaatca atctcctcgc tgggaagagt cagtgaagtt   10020
gattacggcc ctgcaattct ttcgcttcaa tatcattacg atagctttga gcgactttat   10080
ccatatgttg gggttggtgt tggtcgggtg ctattttttg ataaaaccga cggtgctttg   10140
agttcgtttg atattaagga taaatgggcg cctgcttttc aggttggcct tagatatgac   10200
cttggtaact catggatgct aaattcagat gtgcgttata ttccttttcaa aacggacgtc   10260
acaggtactc ttggcccggt tcctgtttct actaaaattg aggttgatcc tttcattctc   10320
agtcttggtg cgtcatatgt tttctaagta atcaggtctg tcactgtcgc aggtcgacct   10380
gcagccaagc ttctgttttg gcggatgaga aagattttc agcctgatac agattaaatc   10440
agaacgcaga agcggtctga taaaacagaa tttgcctggc ggcagtagcg cggtggtccc   10500
acctgacccc atgccgaact cagaagtgaa acgccgtagc gccgatggta gtgtgggtc    10560
tccccatgcg agagtaggga actgccaggc atcaaataaa acgaaaggct cagtcgaaag   10620
actgggcctt tcgttttatc tgttgtttgt cggtgaacgc tctcctgagt aggacaaatc   10680
cgccgggagc ggatttgaac gttgcgaagc aacggcccgg agggtggcgg caggacgcc    10740
cgccataaac tgccaggcat caaattaagc agaaggccat cctgacggat ggcctttttg   10800
cgtttctaca aactcttttg tttattttc taaatacatt caaatatgta tccgctcatg   10860
agacaataac cctgataaat gcttcaataa tgcagcctga aaggcaggcc gggccgtggt   10920
ggccacggcc tctaggccag atccagcggc atctgggtta gtcgagcgcg gccgcttcc    10980
catgtctcac cagggcgagc ctgtttcgcg atctcagcat ctgaaatctt cccggccttg   11040
cgcttcgctg gggccttacc caccgccttg gcgggcttct tcggtccaaa actgaacaac   11100
agatgtgtga ccttgcgccc ggtctttcgc tgcgcccact ccacctgtag cgggctgtgc   11160
tcgttgatct gcgtcacggc tggatcaagc actcgcaact tgaagtcctt gatcgaggga   11220
taccggcctt ccagttgaaa ccactttcgc agctggtcaa tttctatttc gcgctggccg   11280
atgctgtccc attgcatgag cagctcgtaa agcctgatcg cgtgggtgct gtccatcttg   11340
gccacgtcag ccaaggcgta tttggtgaac tgtttggtga gttccgtcag gtacggcagc   11400
atgtctttgg tgaacctgag ttctacacgc cctcaccct cccggtagat gattgtttgc    11460
acccagccgg taatcatcac actcggtctt ttccccttgc cattgggctc ttgggttaac   11520
cggacttccc gccgtttcag gcgcagggcc gcttctttga gctggttgta ggaagattcg   11580
atagggacac ccgccatcgt cgctatgtcc tccgccgtca ctgaatacat cacttcatcg   11640
gtgacaggct cgctcctctt cacctggcta atacaggcca gaacgatccg ctgttcctga   11700
```

| | | | | | |
|---|---|---|---|---|---|
| acactgaggc | gatacgcggc | ctcgaccagg | gcattgcttt | tgtaaaccat | tgggggtgag | 11760
| gccacgttcg | acattccttg | tgtataaggg | gacactgtat | ctgcgtccca | caatacaaca | 11820
| aatccgtccc | tttacaacaa | caaatccgtc | ccttcttaac | aacaaatccg | tcccttaatg | 11880
| gcaacaaatc | cgtcccttt | taaactctac | aggccacgga | ttacgtggcc | tgtagacgtc | 11940
| ctaaaaggtt | taaagggaa | aggaagaaa | agggtggaaa | cgcaaaaaac | gcaccactac | 12000
| gtggccccgt | tggggccgca | tttgtgcccc | tgaaggggcg | gggaggcgt | ctgggcaatc | 12060
| cccgttttac | cagtccccta | tcgccgcctg | agagggcgca | ggaagcgagt | aatcagggta | 12120
| tcgaggcgga | ttcacccttg | gcgtccaacc | agcggcacca | gcggcgcctg | agaggcgaat | 12180
| tgacataagc | ctgttcggtt | cgtaaactgt | aatgcaagta | gcgtatgcgc | tcacgcaact | 12240
| ggtccagaac | cttgaccgaa | cgcagcggtg | gtaacgcgc | agtggcggtt | ttcatggctt | 12300
| gttatgactg | ttttttgta | cagtctatgc | ctcgggcatc | caatcgat | | 12348

<210> SEQ ID NO 12
<211> LENGTH: 6834
<212> TYPE: DNA
<213> ORGANISM: Artificial Sequence
<220> FEATURE:
<223> OTHER INFORMATION: vector

<400> SEQUENCE: 12

| | | | | | |
|---|---|---|---|---|---|
| accaatgctt | aatcagtgag | gcacctatct | cagcgatctg | tctatttcgt | tcatccatag | 60
| ttgcctgact | ccccgtcgtg | tagataacta | cgatacggga | gggcttacca | tctggcccca | 120
| gcgctgcgat | gataccgcga | gaaccacgct | caccggctcc | ggatttatca | gcaataaacc | 180
| agccagccgg | aagggccgag | cgcagaagtg | gtcctgcaac | tttatccgcc | tccatccagt | 240
| ctattaattg | ttgccgggaa | gctagagtaa | gtagttcgcc | agttaatagt | ttgcgcaacg | 300
| ttgttgccat | cgctacaggc | atcgtggtgt | cacgctcgtc | gtttggtatg | gcttcattca | 360
| gctccggttc | ccaacgatca | aggcgagtta | catgatcccc | catgttgtgc | aaaaaagcgg | 420
| ttagctcctt | cggtcctccg | atcgttgtca | gaagtaagtt | ggccgcagtg | ttatcactca | 480
| tggttatggc | agcactgcat | aattctctta | ctgtcatgcc | atccgtaaga | tgcttttctg | 540
| tgactggtga | gtactcaacc | aagtcattct | gagaatagtg | tatgcggcga | ccgagttgct | 600
| cttgcccggc | gtcaatacgg | gataataccg | cgccacatag | cagaacttta | aaagtgctca | 660
| tcattggaaa | acgttcttcg | gggcgaaaac | tctcaaggat | cttaccgctg | ttgagatcca | 720
| gttcgatgta | acccactcgt | gcacccaact | gatcttcagc | atcttttact | ttcaccagcg | 780
| tttctgggtg | agcaaaaaca | ggaaggcaaa | atgccgcaaa | aaagggaata | agggcgacac | 840
| ggaaatgttg | aatactcata | ttcttccttt | ttcaatatta | ttgaagcatt | tatcagggtt | 900
| attgtctcat | gagcggatac | atatttgaat | gtatttagaa | aaataaacaa | ataggggtca | 960
| gtgttacaac | caattaacca | attctgaaca | ttatcgcgag | cccatttata | cctgaatatg | 1020
| gctcataaca | ccccttgttt | gcctggcggc | agtagcgcgg | tggtcccacc | tgaccccatg | 1080
| ccgaactcag | aagtgaaacg | ccgtagcgcc | gatggtagtg | tggggactcc | ccatgcgaga | 1140
| gtagggaact | gccaggcatc | aaataaaacg | aaaggctcag | tcgaaagact | gggcctttcg | 1200
| cccgggctaa | ttatggggtg | tcgcccttat | tcgactctat | agtgaagttc | ctattctcta | 1260
| gaaagtatag | gaacttctga | agtggggatc | cggccgcct | gcagcccgc | agggcctgtc | 1320
| tcggtcgatc | attcagcccg | gctcatagat | atgcgggcag | tgagcgcaac | gcaattaatg | 1380

-continued

```
taagttagct cactcattag gcaccccagg cttgacactt tatgcttccg gctcgtataa    1440
tgtgtggaat tgtgagcgga taacaataac aatttcacac aggatctagg aaccaaggag    1500
agtggcatat gatcatcggc gtccctaaag aaatcaaaaa caacgaaaac cgcgtggcac    1560
tgaccccggg tggtgtgtcc caattgatca gcaacggcca ccgtgtcttg gtcgaaaccg    1620
gcgctggtct gggtagcggc tttgagaacg aggcatacga gtcggcaggt gcggagatta    1680
ttgccgatcc taagcaggtg tgggacgccg agatggttat gaaagtgaaa gaaccgctgc    1740
cggaagaata cgtttacttt cgcaaaggtc tggttctgtt cacctatctg cacttggccg    1800
ctgagccgga gctggcacaa gcgctgaagg ataagggcgt tacggcgatc gcgtatgaaa    1860
cggtgtctga gggccgtacc ctgccgctgc tgaccccgat gagcgaggtt gccggtcgta    1920
tggcagccca gatcggtgcg cagttcctgg agaaaccgaa aggtggcaag gcattctgc     1980
tggcgggtgt cccgggtgtt tctcgtggta aggtcactat cattggcggt ggcgtggtcg    2040
gtaccaacgc ggcgaagatg gcggttggcc tgggtgctga cgttacgatt atcgacttga    2100
acgctgatcg cctgcgtcaa ttggacgaca tctttggcca ccagatcaag accttgatct    2160
ccaatccggt gaatatcgcg gacgcggtgg cggaggcgga tctgctgatt tgcgcagttc    2220
tgattcctgg cgcgaaggcg ccgacccctgg tcacggaaga aatggtgaaa caaatgaaac    2280
cgggtagcgt gattgttgac gtagcgattg atcagggtgg tatcgtggaa actgttgacc    2340
acatcacgac tcatgatcag ccgacgtacg agaaacatgg tgttgttcac tatgcagttg    2400
caaatatgcc gggtgcggtc ccgcgtacta gcacgattgc cctgaccaat gtgaccgttc    2460
cgtatgcact gcaaattgca ataagggtg cggtgaaggc tttggcggac aacaccgcgc     2520
tgcgtgctgg tctgaatacc gcgaacggtc atgtgaccta tgaggcggtc gcacgtgacc    2580
tgggttatga gtacgtgcct gcagagaagg cactgcagga cgagagctcc gtggcaggtg    2640
cgtaataagc tttaaggaga tataatatgc agaaacagcg taccacctct cagtggcgtg    2700
aactggatgg ggcgcatcat ctgcatccgt ttaccgatac cgcgagcctg aatcaggcgg    2760
gtgcgcgtgt gatgacccgt ggcgaaggcg tgtatctgtg ggatagcgaa ggcaacaaaa    2820
ttattgatgg catggcgggc ctgtggtgcg tgaacgtggg ctatggccgt aaagattttg    2880
cggaagcggc gcgtcgtcag atggaagaac tgccgttttta taacaccttc tttaaaacca    2940
cccatccggc ggtggtggaa ctgagcagcc tgctggccga agttaccccg gcaggttttg    3000
atcgtgtgtt ttataccaac agcggcagcg aaagcgtgga taccatgatt cgtatggtgc    3060
gtcgttattg ggatgtgcag ggcaaaccgg aaaaaaaaac cctgattggc cgttggaacg    3120
gctatcacgg cagcaccatt ggcggtgcga gcctgggcgg catgaaatat atgcatgaac    3180
agggcgatct gccgattccg ggcatggcgc atattgaaca gccgtggtgg tataaacatg    3240
gcaaagatat gaccccggat gaatttggcg tggttgcggc gcgttggctg gaagaaaaaa    3300
ttctggaaat cggcgcggat aaagtggcgg cgtttgtggg cgaaccgatt cagggtgcgg    3360
gcggtgtgat tgttccgccg gcaacctatt ggccggaaat tgaacgtatt tgccgcaaat    3420
atgatgtgct gctggttgcg gatgaagtga tttgcggctt tggccgtacc ggcgaatggt    3480
ttggccatca gcattttggc tttcagccgg acctgtttac cgcggcgaaa ggcctgagca    3540
gcggctatct gccgattggc gcggtgtttg tgggcaaacg tgttgcggaa ggtctgattg    3600
cgggcggtga ttttaaccat ggctttacct atagcggcca tccggtgtgt gcggcggtgg    3660
cgcatgcgaa tgttgcggcg ctgcgtgatg aaggcattgt gcagcgtgtg aaagatgata    3720
ttggcccgta tatgcagaaa cgttggcgtg aaaccttag ccgttttgaa catgtggatg     3780
```

```
atgtgcgtgg cgtgggcatg gtgcaggcgt ttaccctggt gaaaaacaaa gcgaaacgtg    3840
aactgtttcc ggattttggc gaaattggca ccctgtgccg cgatatttt tttcgcaaca     3900 acctgattat gcgtgcgtgc ggcgatcaca ttgtgtctgc accgccgctg gttatgaccc    3960
gtgcggaagt ggatgaaatg ctggccgtgg cggaacgttg cctggaagaa tttgaacaga    4020
ccctgaaagc gcgtggcctg gcctaaacta gttcaacaac tctcctggcg caccatcgtc    4080
ggctacagcc tcgggaattg ctgcaagtcg acggatcgcc ggaattaatt ctcatgtttg    4140
acagcttatc actgatcagt gaattaatgg cgatgacgca tcctcacgat aatatccggg    4200
taggcgcaat cactttcgtc tctactccgt tacaaagcga ggctgggtat ttcccggcct    4260
ttttgggccg gccggatcca aaatgaaggg aagttcctat actttctaga aataggaac    4320 ttctataggg agtcgaataa gggcgacaca aaaggtattc taaatgcata ataaatactg    4380
ataacatctt atagttgta ttatattttg tattatcgtt gacatgtata attttgatat     4440
caaaaactga tttcccttt attatttcg agattttatt tcttaattct ctttaacaaa     4500
ctagaaatat tgtatataca aaaaatcata aataatagat gaatagttta attataggtg    4560
ttcatcaatc gaaaaagcaa cgtatcttat ttaaagtgcg ttgcttttt ctcatttata     4620 aggttaaata attctcatat atcaagcaaa gtgacaggcg cccttaaata ttctgacaaa    4680 tgctcttcc ctaaactccc cccataaaaa aaccgccga gcgggttt tacgttattt       4740 gcggattaac gattactcgt tatcagaacc gcccaggatg cctggcagtt ccctactctc    4800
gccgctgcgc tcggtcgttc ggctgcggga cctcagcgct agcggagtgt atactggctt    4860
actatgttgg cactgatgag ggtgtcagtg aagtgcttca tgtggcagga gaaaaaggc    4920 tgcaccggtg cgtcagcaga atatgtgata caggatatat tccgcttcct cgctcactga    4980
ctcgctacgc tcggtcgttc gactgcggcg agcggaaatg gcttacgaac ggggcggaga    5040 ttcctggaa gatgccagga agatacttaa cagggaagtg agagggccgc ggcaaagccg     5100 ttttccata ggctccgccc ccctgacaag catcacgaaa tctgacgctc aaatcagtgg     5160
tggcgaaacc cgacaggact ataaagatac caggcgtttc ccctggcgg ctccctcgtg     5220 cgctctcctg ttcctgcctt tcggttacc ggtgtcattc cgctgttatg gccgcgtttg     5280
tctcattcca cgcctgacac tcagttccgg gtaggcagtt cgctccaagc tggactgtat    5340
gcacgaaccc cccgttcagt ccgaccgctg cgccttatcc ggtaactatc gtcttgagtc    5400
caacccggaa agacatgcaa aagcaccact ggcagcagcc actggtaatt gatttagagg    5460
agttagtctt gaagtcatgc gccggttaag gctaaactga aaggacaagt tttggtgact    5520
gcgctcctcc aagccagtta cctcggttca aagagttggt agctcagaga accttcgaaa    5580
aaccgccctg caaggcggtt ttttcgtttt cagagcaaga gattacgcgc agaccaaaac    5640
gatctcaaga agatcatctt attaatcact gcccgctttc cagtcgggaa acctgtcgtg    5700
ccagctgcat taatgaatcg gccaacgcgc ggggagaggc ggtttgcgta ttgggcgcca    5760
gggtggtttt tcttttcacc agtgagactg gcaacagctg attgcccttc accgcctggc    5820
cctgagagag ttgcagcaag cggtccacgc tggtttgccc cagcaggcga aaatcctgtt    5880
tgatggtggt taacggcggg atataacatg agctatcttc ggtatcgtcg tatcccacta    5940
ccgagatatc cgcaccaacg cgcagcccgg actcggtaat ggcgcgcatt gcgcccagcg    6000
ccatctgatc gttggcaacc agcatcgcag tgggaacgat gccctcattc agcatttgca    6060
tggtttgttg aaaaccggac atggcactcc agtcgccttc ccgttccgct atcggctgaa    6120
```

| | |
|---|---|
| tttgattgcg agtgagatat ttatgccagc cagccagacg cagacgcgcc gagacagaac | 6180 |
| ttaatgggcc cgctaacagc gcgatttgct ggtgacccaa tgcgaccaga tgctccacgc | 6240 |
| ccagtcgcgt accgtcctca tgggagaaaa taatactgtt gatgggtgtc tggtcagaga | 6300 |
| catcaagaaa taacgccgga acattagtgc aggcagcttc cacagcaatg gcatcctggt | 6360 |
| catccagcgg atagttaatg atcagcccac tgacgcgttg cgcgagaaga ttgtgcaccg | 6420 |
| ccgctttaca ggcttcgacg ccgcttcgtt ctaccatcga caccaccacg ctggcaccca | 6480 |
| gttgatcggc gcgagattta atcgccgcga caatttgcga cggcgcgtgc agggccagac | 6540 |
| tggaggtggc aacgccaatc agcaacgact gtttgcccgc cagttgttgt gccacgcggt | 6600 |
| tgggaatgta attcagctcc gccatcgccg cttccacttt ttcccgcgtt ttcgcagaaa | 6660 |
| cgtggctggc ctggttcacc acgcgggaaa cggtctgata agagacaccg gcatactctg | 6720 |
| cgacatcgta taacgttact ggtttcatat tcaccaccct gaattgactc tcttccgggc | 6780 |
| gctatcatgc cataccgcga aaggttttgc gccattcgat ggcgcgccgc tttt | 6834 |

```
<210> SEQ ID NO 13
<211> LENGTH: 14403
<212> TYPE: DNA
<213> ORGANISM: Artificial Sequence
<220> FEATURE:
<223> OTHER INFORMATION: vector

<400> SEQUENCE: 13
```

| | |
|---|---|
| cggcccgggg ctaattaggg ggtgtcgccc ttcttagtcg ctgaaaacgt tgaattccct | 60 |
| tgggactcta gagatccgcg ggggcccccc gggggcgcgc caagtatagg aacttccctt | 120 |
| cattttggat ccggccggcc caaaaaggcc gggaaatacc cagcctcgct ttgtaacgga | 180 |
| gtagagacga aagtgattgc gcctacccgg atattatcgt gaggatgcgt catcgccatt | 240 |
| aattcactga tcagtgataa gctgtcaaac atgagaatta attccggcga tccgtcgact | 300 |
| tgcagcaatt cccgaggctg tagccgacga tggtgcgcca ggagagttgt tgaactagtt | 360 |
| agtataacag gcgtgagtac caacgctcta gattattagg cgaggccacg cgctttgagg | 420 |
| gtctgttcaa attcttcgag gcaacgttcc gccacggcga gcatttcatc cacttccgca | 480 |
| cgggtcataa cgagcggcgg tgcagacaca atgtgatcgc cgcacgcacg cataatgagg | 540 |
| ttgttgcgaa aaaaaatatc gcggcagagg gtgccaattt cgccaaaatc cggaaagagt | 600 |
| tcacgtttcg ctttgttttt cacgagggta acgcctgca ccatgcccac gccacgcaca | 660 |
| tcatccacat gttcaaaacg gctaaaggtt tcacgccaac gtttctgcat atacgggcca | 720 |
| atatcatctt tcacacgctg cacaatgcct tcatcacgga gcgccgcaac attcgcatgc | 780 |
| gccaccgccg cacacaccgg atggccgcta taggtaaagc catggttaaa atcaccgccc | 840 |
| gcaatgagac cttccgcaac acgtttgccc acaaacaccg cgccaatcgg gagatagccg | 900 |
| ctgctgaggc ctttcgccgc ggtaaagagg tccggctgaa agccaaaatg ctgatggcca | 960 |
| aaccattcgc cggtacggcc aaagccgcaa atcacttcat ccgcaacgag gagcacatca | 1020 |
| tatttgcggc aaatacgttc aatttccggc caataggttg ccggcggaac aatcacaccg | 1080 |
| cccgcaccct gaatcggttc gcccacaaac gccgccactt tatccgcgcc gatttcgaga | 1140 |
| attttttctt cgagccaacg cgccgcaacc acgccaaatt catccggggt catatctttg | 1200 |
| ccatgtttat accaccacgg ctgttcaata tgcgccatgc ccggaatcgg gagatcgccc | 1260 |
| tgttcatgca tatatttcat gccgccgagg ctcgcaccgc caatggtgct gccgtgatag | 1320 |
| ccgttccaac ggccaatgag ggttttttttt tccggtttgc cctgcacatc ccaataacga | 1380 |

```
cgcaccatac gaatcatggt atccacgctt tcgctgccgc tgttggtata aaacacacga   1440
tcaaaacctg ccggggtaac ttcggcgagg aggctgctga gttccaccac cgccggatgg   1500
gtggttttaa agaaggtgtt ataaaacggg agttcttcca tctgacgacg cgccgcttcc   1560
gcaaaatctt tacggccata gcccacgttc acgcaccaga ggcccgccat gccatcaata   1620
attttgttgc cttcgctatc ccagagatac acgccttcgc cacgggtcat cacacgcgca   1680
cccgcctgat tgaggctcgc ggtatcggta acggatgga gatgatgcgc cgcatcgagt    1740
tcacgccact gagaggtggt acgctgtttc tgcatattat atctccttaa ctcgagttat   1800
tacgcacctg ccacggagct ctcgtcctgc agtgccttct ctgcaggcac gtactcataa   1860
cccaggtcac gtgcgaccgc ctcataggtc acatgaccgt tcgcggtatt cagaccagca   1920
cgcagcgcgg tgttgtccgc caaagccttc accgcaccct tatttgcaat ttgcagtgca   1980
tacggaacgg tcacattggt cagggcaatc gtgctagtac gcgggaccgc acccggcata   2040
tttgcaactg catagtgaac aacaccatgt ttctcgtacg tcggctgatc atgagtcgtg   2100
atgtggtcaa cagtttccac gataccaccc tgatcaatcg ctacgtcaac aatcacgcta   2160
cccggtttca tttgtttcac catttcttcc gtgaccaggg tcggcgcctt cgcgccagga   2220
atcagaactg cgcaaatcag cagatccgcc tccgccaccg cgtccgcgat attcaccgga   2280
ttggagatca aggtcttgat ctggtggcca aagatgtcgt ccaattgacg caggcgatca   2340
gcgttcaagt cgataatcgt aacgtcagca cccaggccaa ccgccatctt cgccgcgttg   2400
gtaccgacca cgccaccgcc aatgatagtg accttaccac gagaaacacc cgggacaccc   2460
gccagcagaa tgcccttgcc acctttcggt ttctccagga actgcgcacc gatctgggct   2520
gccatacgac cggcaacctc gctcatcggg gtcagcagcg gcagggtacg ccctcagac    2580 accgtttcat acgcgatcgc cgtaacgccc ttatccttca gcgcttgtgc cagctccggc   2640
tcagcggcca agtgcagata ggtgaacaga accagacctt tgcgaaagta acgtattct    2700 tccggcagcg gttctttcac tttcataacc atctcggcgt cccacacctg cttaggatcg   2760
gcaataatct ccgcacctgc cgactcgtat gcctcgttct caaagccgct acccagacca   2820
gcgccggttt cgaccaagac acggtggccg ttgctgatca attgggacac accacccggg   2880
gtcagtgcca cgcggttttc gttgttttg atttctttag gacgccgat gatcatatgc     2940 cactctcctt ggttcctaga tcctgtgtga aattgttatt gttatccgct cacaattcca   3000
cacattatac gagccggaag cataaagtgt caagcctggg gtgcctaatg agtgagctaa   3060
cttacattaa ttgcgttgcg ctcactgccc ctgcaggggc cggccgttta aacaccaggt    3120
gcgatcgcgc ggccgcgctc gagaacgctt accgccaaca cagcagtgta tttgaataag   3180
agctcgaaca tgatcggatc tcccatttca gcaaggaaa tcccaccata gccaccaccg    3240
atttatgtgg cgtagaaaac ggtcatcacc aaatatggca atacttcccc gcccaagcgc   3300
cacataacag cctgggccac attttacgcg gtagttccgc acgtacggag tgcgggggc    3360 ggcaggtaac tgccgtccct atcgcgaccg ttggttcgag tggctgagca tcattgctaa   3420
tcaggtaatt ttatactccc tgcaagcgca ccttgacgtt taggcaaatt tattgtctca   3480
gttgcaatca gtcgctcctg cttgtacgca aggacttcta gttcaagagt ttcgttatta   3540 attcaacaa cgagtttatc gtagtccttt agagcaccaa gtccttgcag cgccatccct   3600
ttaagatcag accagaaccg tggtgggtt ggtgctggtg ttgatgtgcc acagatgcta    3660
cttgcgacaa tttgagcgtg tgtaaccgca ttatgaattg tctctaaacg taccatcgtt   3720
```

```
ccccaaaaag gatttctagc cattgcgcag tcgccgattg catatatact tgtatccgat    3780
gtacacatct gatcatcgac cacaacacca ttactcactt caagggccgc ctcagttgcc    3840
agctctagct ctgggatagc accgattcca actacaatca gatccgcctg aatttcttct    3900
ccactttcaa gtacgcattg ttcaacatgg ccattcctgc cctttataga cgttaatttc    3960
gcattcagct tgaactcaat tccttcagcc tccaggcggg ctctgactaa gtttgctgct    4020
gccggcgtaa ccacgcgcgc cattacacgc ggggtggctt ctatcactgt gaccctcttc    4080
cctaagccca ccgcagctga ggcgacttca agcccgatta ctccgccgcc aacacaaca    4140
acagacgcac tctccacaag tttcctacgt aaattttggg cgtcttccat actgcgtaaa    4200
tagcagaccc cagacagttc agacccctcg caggttaacc tacgtgcgct agcaggtgtt    4260
gcaagaatca attttcata cgcgtattct tttccatctt tagaagaaac tatcttacgc     4320
cccacgtcga ttgatacaat cggtgtattt aacgaaatgg taatattgtt attcgtataa    4380
aaaccttctg gctttaatgg cactgcggat tctgcaatct cacttgtcag aaaagccttg    4440
gatagaggag gccgctgata aggcgccaca gactccctgc taaaaatcct aatttccct     4500
ttataaccat attgacgaag ccagaacgca gcatttactc cagctgtacc agcgccaaca    4560
acaacgattg ccataattct ctctccggta tactttcac tatatcactt aatgccgatt     4620
attttagata attccttgac gctcagcttc aattgttgct tgcgtgcgat tcactacatt    4680
caaggtggca aatattttcc tcatatgcca ctttatagca tcttcggtga catgcatatt    4740
tgttgctatt tgtttgtttg agcaccctc ttttacaagc ctcaagacag caatctgctt     4800
ccgtgtcaat aaagcgtcag ctttattctc tgcggacttt ccaatctcaa ctattcgcgg    4860
aagactaaaa gccccaatcg cttgatctaa attaactgct gtgaaggctt cacatgaagc    4920
cggtattatt cgctcaatta acatacttc atcaagaact gtttgaaagc attgaagctg     4980
ttttgctatc tccactgcat aaacaatgtt aagctgagcc ttttttaaat caccggcacc    5040
tgcctgcgct ccggccaaac acaataatcc acggacttcc agctggcccg cgttaatttt    5100
acgggcttgc tgaatagcca ataacgctct gtgcgcggca ctatgaaagt tccgatctcg    5160
ggaaagcact agtgattgaa caagcagcag gcgtgctttt aggggggctg agtgctgtcc    5220
ggagaaaatc ttatgatctt caagagtttt taaattattt atgcccgtta tgccttgaca    5280
gactaagcgc tgatagatct caatttggct cataacttcc aatcttggta gattttttc     5340
aaccgcatgc gccttcgccc actccaatat ctcaatggag ccatttaggt cactccttcc    5400
aagccgccaa gctgacacag cacggcatac ggaaaaaaac acgtctgtca ccccgtgatt    5460
ggaaatgaac tctaaaattt tggagagctt ttcttctgag gtgtccaagc agcgcaattc    5520
ataatgtaac tcaagctcta gagcgtcaaa catttcgaa gtaaactcgg attccatcat     5580
ctgcgcgcga ctgtctgtgc gtgcttgagt tataatctgc ctcgcccagc ccattttcc     5640
gcttgctagg gcttgttgaa acctcgcgac atacagccaa ccaaaagcaa attttgttt     5700
tgcaaattta ttcacggctt gggcctgagc cagcaccttc tccaactctg caaatctata    5760
ctcactggca aaaataaaag ccaaacaggt tagcgcggcc ccttttccaa ctgcgtttga    5820
atccccaaat aaactaatcc acttattaca gagctcctca ctcgaaagca tttcatcttt    5880
ggttgcttta cctattgcaa gcacaagctg cagccattcc ttttcttgcc atttatttt     5940
tttatcggat tgtgaagata ggtctttaat taacttctct gctcgcgcgc cttgctgact    6000
gaaatacaat acccacgcgt aactaataag cactatgggt ttttggtgcc aggcctgctt    6060
cggcagctct aacagccact gtctcagcgc atctatttcg ccctgacgaa atgacaaatc    6120
```

```
taaaattatt ctctcagaca tgctgactgc ccagcgacag tcattcgccc gtagggatat    6180
tcgtattgca tactggtatt cacctctacg ccaatgccaa aaagctgcac gcttaagcag    6240
gtaggatctt ttagcaggat tttcagtcca agtaatttct cgtagaaaat tacgcagtac    6300
tggatgcagt gtaaactgcg ctggctcacc gctcacatgg cgaagcaaca tgtaattagt    6360
gcttaaatac ttaatacatg agacccatt gacgcatttg aatacataat tgtattgatc     6420
aggcgtcacg aaatcgagca atgaagaatt tgcaagaaaa acacgatagc gctcgggaat    6480
cgcctcaaat atttcatccc taaagtaatt gtctacttca actactgctg aaatatgctt    6540
ggccggcaac tcacgcttta acaaaaaaac tacaagagca ggccacccct caacttcttg    6600
caccaaggtc tctatctgtt cttcaggaac tccaagaaca gactctgcct ccgctaacgc    6660
caccgcctct tctgcgctaa aggccaagtc tttctcggtg tactcccgca tagcgcctgc    6720
aagtttaagc tgcgagaacc ctttttattgt attgcctgca actgcaaacc tgatatttt    6780 tggtgtattt aacataaact ccataagtgc gtgcaacaac ggcaagtcta agtcatgatt    6840
aatattatcc aaacaaacta gcgtttctat ctcgttattc gaggtgctct gccaaagact    6900
agatgcaagg tctcgcaaga gcgcaggctt gctcacaccc tctctcacac ggctgaattt    6960
taccatttcg aaagtttcaa gctgctcaat aatctctgcg cagatatcaa attcactgta    7020
agaactggct cttaaagaaa gccacactgc aggacgtccg gctgttctgt ggcgtagcca    7080
ctcgaacgca agagcaacgg ttttcccata tccaggtggg gctctgtaaa ggcatactct    7140
gggagcggct ccatccgcga tactcaatct tggccgatat atgcaactat gaactttggc    7200
acttactaga gtcgtaattt gatccgctcc gaccttagcg accgggaaat cattatttat    7260
tattattttc attatgctat tctcgcgcca gctgactgga aattttcacc ataggttacg    7320
gtgttaaata ttaaaactac acttaagtgt agtcggcatg atcggtggtg caaaatattt    7380
actagggaag gtctgaagta ggccgctatt tctggccgac ttcggccttc gccgattttg    7440
aagacgggca ccgggtcaaa atcgaccaga tagctcgctc atttcggtgc tttcagccgt    7500
cgcgagtagc tcgcggtacc tggcatgctt gcggccagct cgtgtttttc cagcagacga    7560
cggagcaaaa actacccgta ggtgtagttg gcgcaagcgt ccgattagct caggtttaag    7620
atgtcgagag tgagagtggg cggcttaact ttctcagtta ggcataaaat tacgtcttaa    7680
atctcgtagc gactaattta ataaaaattg gagaattcca tatgcttgag aaacacagag    7740
ttctggattc cgctccagag tacgtagata aaaagaaata tctctggata ctatcaactt    7800
tgtggccggc tactccgatg atcggaatct ggcttgcaaa tgaaactggt tggggattt     7860 tttatgggct ggtattgctc gtatggtacg gcgcacttcc attgcttgat gcgatgtttg    7920
gtgaggactt taataatccg cctgaagaag tggtgccgaa actagagaag gagcggtact    7980
atcgagtttt gacatatcta acagttccta tgcattacgc tgcattaatt gtgtcagcat    8040
ggtgggtcgg aactcagcca atgtcttggc ttgaaattgg tgcgcttgcc ttgtcactgg    8100
gtatcgtgaa cggactagcg ctcaatacag gacacgaact cggtcacaag aaggagactt    8160
ttgatcgttg gatggccaaa attgtgttgg ctgtcgtagg gtacggtcac ttctttattg    8220
agcataataa gggtcatcac cgtgatgtcg ctacaccgat ggatcctgca acatcccgga    8280
tgggagaaag catttataag ttttcaatcc gtgagatccc aggagcattt attcgtgctt    8340
gggggcttga ggaacaacgc ctttcgcgcc gtggccaaag cgtttggagt ttcgataatg    8400
aaatcctcca accaatgatc atcacagtta ttctttacgc cgttctcctt gccttgtttg    8460
```

```
gacctaagat gctggtgttc ctgccgattc aaatggcttt cggttggtgg cagctgacca   8520
gtgcgaacta tattgaacat tacggcttgc tccgtcaaaa aatggaggac ggtcgatatg   8580
agcatcaaaa gccgcaccat tcttggaata gtaatcacat cgtctctaat ctagtgctgt   8640
tccaccttca gcggcactcg gatcaccacg cgcatccaac acgttcttat cagtcacttc   8700
gggattttcc cggcctgccg gctcttccga cgggttaccc tggtgcattt ttgatggcga   8760
tgattcctca gtggtttaga tcagttatgg atcccaaggt agtagattgg gctggtggtg   8820
accttaataa gatccaaatt gatgattcga tgcgagaaac ctatttgaaa aaatttggca   8880
ctagtagtgc tggtcatagt tcgagtacct ctgcggtagc atcgtagtta tgtgagcacg   8940
cagagcccgg cggtcgatat ttacaataag tgcttcaatt ttatgtgcgg cgttgaaagc   9000
tctcacaaag agtgcacttc gctaaagtgc tgagggttga ttgcctctct gtaattgctt   9060
tgaaggcgac ctgctccgat agttacactc tgatgaagtt gtcggagcag cgactaacgc   9120
tgagttaata ggagagtggg agaatgtcaa ggtaccagtg tccagattgt cagtatatct   9180
atgatgaaaa taaggggag ccgcacgaag gtttccaccc gaacaccagc tggaatgata   9240
tccccaaaga ttgggcatgc ccggactgcg cagttcgaga caaggtggac tttatctttc   9300
tcgcggattc ccctcgaaa gaaacacagc taggggtgaa tagtcagctt gccaactcgg   9360
aaagtggtat ttcagatgct actccaactg gaatggcagt tttggccgca gaattagtga   9420
tcccacttaa tcaagaaaat aaaaatgagg gctgtgcggc taagactgaa gttcttgatc   9480
aggcgagcac cccacaggtt gtaagaaaat cttccacaag gaagaagatg agaaataaat   9540
aacgcaaatt tgccgcaacg caaaataaca atttgacatg gtgatgagta tggctagcta   9600
taaatgcccg gattgtaatt atgtttatga tgagagtgcg ggtaatgtgc atgaggggtt   9660
ttctccaggt acgccttggc acctattcc tgaggattgg tgctgccccg attgcgccgt   9720
tcgagacaag cttgacttca tgttaattga gagcggcgta ggtgaaaagg gcgtcacctc   9780
aacccatact tcgccaaatt tatccgaggt tagtggcaca agtttaactg ctgaagcagt   9840
ggttgcgccg acaagcttag agaaattgcc tagtgccgac gttaaaggcc aagatctata   9900
taaaactcaa cctccaaggt ctgatgccca aggcgggaaa gcatacttga agtggatatg   9960
tattacttgt ggccatatat atgatgaggc gttgggcgat gaggccgagg gtttactcc   10020 aggtactcgc tttgaggata ttcctgatga ctggtgctgt ccggattgcg gggctacgaa   10080
agaagactat gtgctctacg aggaaaagtg aagattaaaa cttcaagtca ttctaggtaa   10140
ttcaggacaa aataaaaatg accataccaa ttagcctagc caagttaaaac tctagtgccg   10200 atacccattc agcgcttgtc gacctgtaac gacaacaaaa cgagggtagc acaatgagtt   10260
tttctaatta taaagtaatc gcgatgccgg tgttggttgc taattttgtt ttggggggcgg   10320 ccactgcatg ggcgaatgaa aattatccgg cgaaatctgc tggctataat cagggtgact   10380
gggtcgctag cttcaatttt tctaaggtct atgtgggtga ggagcttggc gatctaaatg   10440 ttggagggg ggctttgcca aatgctgatg taagtattgg taatgataca acacttacgt   10500
ttgatatcgc ctattttgtt agctcaaata tagcggtgga ttttttttgtt ggggtgccag   10560 ctagggctaa atttcaaggt gagaaatcaa tctcctcgct gggaagagtc agtgaagttg   10620
attacggccc tgcaattctt tcgcttcaat atcattacga tagctttgag cgactttatc   10680
catatgttgg ggttggtgtt ggtcgggtgc tatttttttga taaaaccgac ggtgctttga   10740
gttcgtttga tattaaggat aaatgggcgc ctgcttttca ggttggcctt agatatgacc   10800
ttggtaactc atggatgcta aattcagatg tgcgttatat tcctttcaaa acggacgtca   10860
```

```
caggtactct tggcccggtt cctgtttcta ctaaaattga ggttgatcct ttcattctca    10920
gtcttggtgc gtcatatgtt ttctaagtaa tcaggtctgt cactgtcgca ggtcgacctg    10980
cagccaagct tctgttttgg cggatgagag aagattttca gcctgataca gattaaatca    11040
gaacgcagaa gcggtctgat aaaacagaat ttgcctggcg gcagtagcgc ggtggtccca    11100
cctgacccca tgccgaactc agaagtgaaa cgccgtagcg ccgatggtag tgtggggtct    11160
ccccatgcga gagtagggaa ctgccaggca tcaaataaaa cgaaaggctc agtcgaaaga    11220
ctgggccttt cgttttatct gttgtttgtc ggtgaacgct ctcctgagta ggacaaatcc    11280
gccgggagcg gatttgaacg atgataagct gtcaaacatg agaattacaa cttatatcgt    11340
atggggctga cttcaggtgc tacatttgaa gagataaatt gcactgaaat ctagaaatat    11400
tttatctgat taataagatg atcttcttga gatcgttttg gtctgcgcgt aatctcttgc    11460
tctgaaaacg aaaaaaccgc cttgcagggc ggttttttcga aggttctctg agctaccaac    11520
tctttgaacc gaggtaactg gcttggagga gcgcagtcac caaaacttgt cctttcagtt    11580
tagccttaac cggcgcatga cttcaagact aactcctcta aatcaattac cagtggctgc    11640
tgccagtggt gcttttgcat gtcttttccgg gttggactca agacgatagt taccggataa    11700
ggcgcagcgg tcggactgaa cggggggttc gtgcatacag tccagcttgg agcgaactgc    11760
ctacccggaa ctgagtgtca ggcgtggaat gagacaaacg cggccataac agcggaatga    11820
caccggtaaa ccgaaaggca ggaacaggag agcgcacgag ggagccgcca gggggaaacg    11880
cctggtatct ttatagtcct gtcgggtttc gccaccactg atttgagcgt cagatttcgt    11940
gatgcttgtc agggggcgg agcctatgga aaaacggctt tgccgcggcc ctctcacttc    12000
cctgttaagt atcttcctgg catcttccag gaaatctccg ccccgttcgt aagccatttc    12060
cgctcgccgc agtcgaacga ccgagcgtag cgagtcagtg agcgaggaag cggaatatat    12120
cctgtatcac atattctgct gacgcaccgg tgcagccttt tttctcctgc cacatgaagc    12180
acttcactga caccctcatc agtgccaaca tagtaagcca gtatacactc cgctagcgct    12240
gatgtccggc ggtgcttttg ccgttacgca ccacccccgtc agtagctgaa caggagggac    12300
agctgataga aacagaagcc actggagcac ctcaaaaaca ccatcataca ctaaatcagt    12360
aagttggcag catcacccga cgcactttgc gccgaataaa tacctgtgac ggaagatcac    12420
ttcgcagaat aaataaatcc tggtgtccct gttgataccg ggaagccctg gccaactttt    12480 tgcgaaaat gagacgttga tcggcacgta agaggttcca actttcacca taatgaaata    12540
agatcactac cgggcgtatt ttttgagtta tcgagatttt caggagctaa ggaagctaaa    12600
atggagaaaa aaatcactgg atataccacc gttgatatat cccaatggca tcgtaaagaa    12660
cattttgagg catttcagtc agttgctcaa tgtacctata accagaccgt tcagctggat    12720
attacggcct ttttaaagac cgtaaagaaa aataagcaca gtttatcc ggcctttatt    12780 cacattcttg cccgcctgat gaatgctcat ccggaattcc gtatggcaat gaaagacggt    12840
gagctggtga tatgggatag tgttcaccct tgttacaccg ttttccatga gcaaactgaa    12900
acgttttcat cgctctggag tgaataccac gacgatttcc ggcagtttct acacatatat    12960
tcgcaagatg tggcgtgtta cggtgaaaac ctggcctatt tccctaaagg gtttattgag    13020
aatatgtttt tcgtctcagc caatccctgg gtgagtttca ccagttttga tttaaacgtg    13080
gccaatatgg acaacttctt cgcccccgtt ttcaccatgg gcaaatatta tacgcaaggc    13140
gacaaggtgc tgatgccgct ggcgattcag gttcatcatg ccgtctgtga tggcttccat    13200
```

```
gtcggcagaa tgcttaatga attacaacag tactgcgatg agtggcaggg cggggcgtaa    13260 ttttttttaag gcagttattg gtgcccttaa acgcctggtg ctacgcctga ataagtgata    13320
ataagcggat gaatggcaga aattcgaaag caaattcgac ccggtcgtcg gttcagggca    13380
gggtcgttaa atagccgctt atgtctattg ctggtttacc ggtttattga ctaccggaag    13440
cagtgtgacc gtgtgcttct caaatgcctg aggccagttt gctcaggctc tccccgtgga    13500
ggtaataatt gacgatatga tcatttattc tgcctcccag agcctgataa aaacggttag    13560
cgcttcgtta atacagatgt aggtgttcca cagggtagcc agcagcatcc tgcgatgcag    13620
atccggaaca taatggtgca gggcgcttgt ttcggcgtgg gtatggtggc aggccccgtg    13680 gccggggggac tgttgggcgc tgccggcacc tgtcctacga gttgcatgat aaagaagaca    13740
gtcataagtg cggcgacgat agtcatgccc cgcgcccacc ggaaggagct accggacagc    13800
ggtgcggact gttgtaactc agaataagaa atgaggccgc tcatggcgtt gactctcagt    13860
catagtatcg tggtatcacc ggttggttcc actctctgtt gcgggcaact tcagcagcac    13920
gtaggggact tccgcgtttc cagactttac gaaacacgga aaccgaagac cattcatgtt    13980
gttgctcagg tcgcagacgt tttgcagcag cagtcgcttc acgttcgctc gcgtatcggt    14040
gattcattct gctaaccagt aaggcaaccc cgccagccta gccgggtcct caacgacagg    14100
agcacgatca tgcgcacccg tggccaggac ccaacgctgc ccgagatgcg ccgcgtgcgg    14160
ctgctggaga tggcggacgc gatggatatg ttctgccaag ggttggtttg cgcattcaca    14220
gttctccgca agaattgatt ggctccaatt cttggagtgg tgaatccgtt agcgaggtgc    14280
cgccggcttc cattcaggtc gaggtggccc ggctccatgc accgcgacgc aacgcgggga    14340
ggcagacaag gtatagggcg cgcctacaa tccatgccaa cccgttccat gtgctcgccg    14400
agg                                                                 14403
```

<210> SEQ ID NO 14
<211> LENGTH: 5664
<212> TYPE: DNA
<213> ORGANISM: Artificial Sequence
<220> FEATURE:
<223> OTHER INFORMATION: vector

<400> SEQUENCE: 14

```
ccctttcgtc ttcgaataaa tacctgtgac ggaagatcac ttcgcagaat aaataaatcc      60
tggtgtccct gttgataccg ggaagccctg ggccaacttt tggcgaaaat gagacgttga     120
tcggcacgta agaggttcca actttcacca taatgaaata agatcactac cgggcgtatt     180
ttttgagtta tcgagatttt caggagctaa ggaagctaaa atggagaaaa aaatcactgg     240
atataccacc gttgatatat cccaatggca tcgtaaagaa catttgagg catttcagtc     300 agttgctcaa tgtacctata accagaccgt tcagctggat attacggcct ttttaaagac     360
cgtaaagaaa aataagcaca gttttatcc ggcctttatt cacattcttg cccgcctgat     420
gaatgctcat ccggaattcc gtatggcaat gaaagacggt gagctggtga tatgggatag     480
tgttcaccct tgttacaccg ttttccatga gcaaactgaa acgttttcat cgctctggag     540
tgaataccac gacgatttcc ggcagtttct acacatatat tcgcaagatg tggcgtgtta     600
cggtgaaaac ctggcctatt tccctaaagg gtttattgag aatatgtttt tcgtctcagc     660
caatccctgg gtgagtttca ccagttttga tttaaacgtg gccaatatgg acaacttctt     720 cgccccgtt tcaccatgg gcaaatatta tacgcaaggc gacaaggtgc tgatgccgct     780
ggcgattcag gttcatcatg ccgtttgtga tggcttccat gtcggcagaa tgcttaatga     840
```

```
attacaacag tactgcgatg agtggcaggg cggggcgtaa ttttttttaag gcagttattg      900
gtgcccttaa acgcctggtg ctacgcctga ataagtgata ataagcggat gaatggcaga      960
aattcgaaag caaattcgac ccggtcgtcg gttcagggca gggtcgttaa atagccgctt     1020
atgtctattg ctggtttatc ggtacccggg gatcgcggcc gcggaccgga tcctctagag     1080
cggccgcgat cctctagagt cgaccggtgg cgaatgggac gcgccctgta gcggcgcatt     1140
aagcgcggcg ggtgtggtgg ttacgcgcag cgtgaccgct acacttgcca gcgccctagc     1200
gcccgctcct ttcgctttct tcccttcctt tctcgccacg ttcgccggct ttccccgtca     1260
agctctaaat cggggggctcc ctttaggggtt ccgatttagt gctttacggc acctcgaccc     1320
caaaaaactt gattagggtg atggttcacg tagtgggcca tcgccctgat agacggtttt     1380
tcgccctttg acgttggagt ccacgttctt aatagtgga ctcttgttcc aaactggaac      1440
aacactcaac cctatctcgg tctattcttt tgatttataa gggattttgc cgatttcggc     1500
ctattggtta aaaaatgagc tgatttaaca aaaatttaac gcgaatttta acaaaatatt     1560
aacgcttaca atttaggtgg cacttttcgg ggaaatgtgc gcggaacccc tatttgttta     1620
tttttctaaa tacattcaaa tatgtatccg ctcatcagat ccttttttaac ccatcacata     1680
tacctgccgt tcactattat ttagtgaaat gagatattat gatattttct gaattgtgat     1740
taaaaaggca actttatgcc catgcaacag aaactataaa aaatacagag aatgaaagaa     1800
aacagataga ttttttagtt ctttaggccc gtagtctgca aatccttttta tgattttcta     1860
tcaaacaaaa gaggaaaata gaccagttgc aatccaaacg agagtctaat agaatgaggt     1920
cgaaaagtaa atcgcgcggg tttgttactg ataaagcagg caagacctaa aatgtgtaaa     1980
gggcaaagtg tatactttgg cgtcaccct tacatatttt aggtcttttt ttattgtgcg     2040
taactaactt gccatcttca aacaggaggg ctggaagaag cagaccgcta acacagtaca     2100
taaaaaagga gacatgaacg atgaacatca aaaagtttgc aaaacaagca acagtattaa     2160
cctttactac cgcactgctg gcaggaggcg caactcaagc gtttgcgaaa gaaacgaacc     2220
aaaagccata taaggaaaca tacggcattt cccatattac acgccatgat atgctgcaaa     2280
tccctgaaca gcaaaaaaat gaaaaatatc aagttcctga ttcgtccaca attaaaaata     2340
tctcttctgc aaaaggcctg gacgtttggg acagctggcc attacaaaac gctgacggca     2400
ctgtcgcaaa ctatcacggc taccacatcg tctttgcatt agccggagat cctaaaaatg     2460
cggatgacac atcgatttac atgttctatc aaaaagtcgg cgaaacttct attgacagct     2520
ggaaaaacgc tggccgcgtc tttaaagaca gcgacaaatt cgatgcaaat gattctatcc     2580
taaaagacca aacacaagaa tggtcaggtt cagccacatt tacatctgac ggaaaaatcc     2640
gtttattcta cactgatttc tccggtaaac attacgcaa acaaacactg acaactgcac     2700
aagttaacgt atcagcatca gacagctctt tgaacatcaa cggtgtagag gattataaat     2760
caatctttga cggtgacgga aaaacgtatc aaaatgtaca gcagttcatc gatgaaggca     2820
actacagctc aggcgacaac catacgctga gagatcctca ctacgtagaa gataaaggcc     2880
acaaatactt agtatttgaa gcaaacactg gaactgaaga tggctaccaa ggcgaagaat     2940
ctttatttaa caaagcatac tatggcaaaa gcacatcatt cttccgtcaa gaaagtcaaa     3000
aacttctgca aagcgataaa aaacgcacgg ctgagttagc aaacggcgct ctcggtatga     3060
ttgagctaaa cgatgattac acactgaaaa agtgatgaa accgctgatt gcatctaaca     3120
cagtaacaga tgaaattgaa cgcgcgaacg tctttaaaat gaacggcaaa tggtacctgt     3180
```

```
tcactgactc ccgcggatca aaaatgacga ttgacggcat tacgtctaac gatatttaca   3240
tgcttggtta tgtttctaat tctttaactg gcccatacaa gccgctgaac aaaactggcc   3300
ttgtgttaaa aatggatctt gatcctaacg atgtaacctt tacttactca cacttcgctg   3360
tacctcaagc gaaaggaaac aatgtcgtga ttacaagcta tatgacaaac agaggattct   3420
acgcagacaa acaatcaacg tttgcgccaa gcttcctgct gaacatcaaa ggcaagaaaa   3480
catctgttgt caaagacagc atccttgaac aaggacaatt aacagttaac aaataaaaac   3540
gcaaaagaaa atgccgatcc ggtttattga ctaccggaag cagtgtgacc gtgtgcttct   3600
caaatgcctc aggctgtcta tgtgtgactg ttgagctgta acaagttgtc tcaggtgttc   3660
aatttcatgt tctagttgct ttgttttact ggtttcacct gttctattag gtgttacatg   3720
ctgttcatct gttacattgt cgatctgttc atggtgaaca gctttaaatg caccaaaaac   3780
tcgtaaaagc tctgatgtat ctatctttt tacaccgttt tcatctgtgc atatggacag   3840
tttttccttt gatatctaac ggtgaacagt tgttctactt ttgtttgtta gtcttgatgc   3900
ttcactgata gatacaagag ccataagaac ctcagatcct tccgtattta gccagtatgt   3960
tctctagtgt ggttcgttgt ttttgcgtga gccatgagaa cgaaccattg agatcatgct   4020
tactttgcat gtcactcaaa aattttgcct caaaactggt gagctgaatt tttgcagtta   4080
aagcatcgtg tagtgttttt cttagtccgt tacgtaggta ggaatctgat gtaatggttg   4140
ttggtatttt gtcaccattc attttatct ggttgttctc aagttcggtt acgagatcca   4200
tttgtctatc tagttcaact tggaaaatca acgtatcagt cgggcggcct cgcttatcaa   4260
ccaccaattt catattgctg taagtgttta aatcttact tattggtttc aaaacccatt   4320
ggttaagcct tttaaactca tggtagttat tttcaagcat taacatgaac ttaaattcat   4380
caaggctaat ctctatattt gccttgtgag ttttcttttg tgttagttct tttaataacc   4440
actcataaat cctcatagag tatttgttt caaaagactt aacatgttcc agattatatt   4500
ttatgaattt ttttaactgg aaaagataag gcaatatctc ttcactaaaa actaattcta   4560
atttttcgct tgagaacttg gcatagtttg tccactggaa aatctcaaag cctttaacca   4620
aaggattcct gatttccaca gttctcgtca tcagctctct ggttgcttta gctaatacac   4680
cataagcatt ttccctactg atgttcatca tctgagcgta ttggttataa gtgaacgata   4740
ccgtccgttc tttccttgta gggttttcaa tcgtggggtt gagtagtgcc acacagcata   4800
aaattagctt ggtttcatgc tccgttaagt catagcgact aatcgctagt tcatttgctt   4860
tgaaaacaac taattcagac atacatctca attggtctag gtgattttaa tcactatacc   4920
aattgagatg ggctagtcaa tgataattac tagtcctttt cctttgagtt gtgggtatct   4980
gtaaattctg ctagaccttt gctggaaaac ttgtaaattc tgctagaccc tctgtaaatt   5040
ccgctagacc tttgtgtgtt ttttttgttt atattcaagt ggttataatt tatagaataa   5100
agaaagaata aaaaaagata aaagaatag atcccagccc tgtgtataac tcactacttt   5160
agtcagttcc gcagtattac aaaaggatgt cgcaaacgct gtttgctcct ctacaaaaca   5220
gaccttaaaa ccctaaaggc ttaagtagca ccctcgcaag ctcgggcaaa tcgctgaata   5280
ttccttttgt ctccgaccat caggcacctg agtcgctgtc tttttcgtga cattcagttc   5340
gctgcgctca cggctctggc agtgaatggg ggtaaatggc actacaggcg cctttttatgg   5400 attcatgcaa ggaaactacc cataatacaa gaaaagcccg tcagggcttt ctcagggcgt   5460
tttatggcgg gtctgctatg tggtgctatc tgacttttg ctgttcagca gttcctgccc   5520
tctgattttc cagtctgacc acttcggatt atcccgtgac aggtcattca gactggctaa   5580
```

```
tgcacccagt aaggcagcgg tatcatcaac aggcttaccc gtcttactgt cggatcgacg    5640
ctctcccttc tgcgactcct gcat                                           5664
```

```
<210> SEQ ID NO 15
<211> LENGTH: 230
<212> TYPE: PRT
<213> ORGANISM: Pseudomonas putida

<400> SEQUENCE: 15

Met Asn Pro Pro Ile Leu Lys Lys Leu Ala Met Ser Ile Leu Ala Thr
1               5                   10                  15

Ser Phe Val Leu Gly Gly Ala Ser Ala Trp Ser Gly Glu Ile Tyr Ser
                20                  25                  30

Thr Glu Thr Ala Gly Tyr Asn Gln Gly Asp Trp Val Ala Ser Phe Asn
            35                  40                  45

Met Ser Lys Val Tyr Val Asp Glu Thr Leu Gly Ser Leu Asn Val Gly
    50                  55                  60

Gly Ala Thr Val Pro Asn Ala Ala Val Ser Ile Gly Asn Asp Thr Thr
65                  70                  75                  80

Val Ser Phe Asp Ile Ser Tyr Phe Ile Ser Asn Asn Val Ala Leu Asp
                85                  90                  95

Phe Phe Val Gly Ile Pro Ala Lys Ala Lys Phe Gln Gly Glu Lys Ser
                100                 105                 110

Ile Ser Ala Leu Gly Arg Val Ser Glu Val Asp Tyr Gly Pro Ala Ile
            115                 120                 125

Leu Ser Leu Gln Tyr His Phe Asp Asn Phe Glu Arg Leu Tyr Pro Tyr
130                 135                 140

Val Gly Leu Gly Val Gly Arg Val Phe Phe Phe Asp Lys Thr Asp Gly
145                 150                 155                 160

Ala Leu Thr Ser Phe Asp Ile Lys Asp Lys Trp Ala Pro Ala Val Gln
                165                 170                 175

Val Gly Leu Arg Tyr Asp Phe Gly Asn Ser Trp Met Leu Asn Ser Asp
            180                 185                 190

Val Arg Tyr Ile Pro Phe Lys Thr Asp Val Ser Gly Thr Leu Gly Ala
        195                 200                 205

Ala Pro Val Ser Thr Lys Ile Glu Ile Asp Pro Phe Ile Leu Ser Leu
    210                 215                 220

Gly Ala Ser Tyr Lys Phe
225                 230
```